United States Patent [19]

Krause et al.

[11] Patent Number: 5,089,168
[45] Date of Patent: Feb. 18, 1992

[54] NITROGEN-CONTAINING HETEROCYCLES

[75] Inventors: Joachim Krause, Dieburg; Rudolf Eidenschink, Münster; Klaus Bofinger, Mühltal; Reinhard Hopf, Berlin; Volker Reiffenrath, Darmstadt; Eike Poetsch, Mühltal, all of Fed. Rep. of Germany; Bernhard Scheuble, Yokohama, Japan; Thomas Geelhaar, Mainz, Fed. Rep. of Germany

[73] Assignee: Merck Patent Gesellschaft mit beschrankter Haftung, Darmstadt, Fed. Rep. of Germany

[21] Appl. No.: 352,308

[22] Filed: May 16, 1989

Related U.S. Application Data

[62] Division of Ser. No. 34,182, Dec. 24, 1986, Pat. No. 4,834,904.

[30] Foreign Application Priority Data

Apr. 27, 1985 [DE] Fed. Rep. of Germany ....... 3515373

[51] Int. Cl.$^5$ ................ C09K 19/34; C09K 19/52; C07D 239/02; C07D 239/26; C07D 241/12; C07D 213/79; C07D 521/00

[52] U.S. Cl. .................. 252/299.61; 252/299.01; 544/224; 544/242; 544/294; 544/315; 544/335; 544/408; 544/409; 546/255; 546/257; 546/258; 546/261; 546/263; 546/267; 546/285; 546/288; 546/290; 546/298; 546/299; 546/300; 546/301; 546/302; 546/303; 546/314; 546/318; 546/321; 546/322; 546/339; 546/340; 546/341; 546/345

[58] Field of Search .......... 252/299.01, 299.1, 299.61, 252/299.65, 299.66; 350/355, 350 R; 544/242, 294, 315, 335, 408, 409, 224; 546/255, 257, 258, 261, 263, 267, 285, 288, 290, 298, 299, 300, 301, 302, 303, 314, 315, 318

[56] References Cited

U.S. PATENT DOCUMENTS

| 4,581,155 | 4/1986 | Goto et al. | 252/299.61 |
| 4,623,477 | 11/1986 | Ogawa et al. | 252/299.5 |
| 4,657,695 | 4/1987 | Saito et al. | 252/299.61 |
| 4,684,477 | 8/1987 | Sugimori et al. | 252/299.61 |
| 4,725,688 | 2/1988 | Taguchi et al. | 544/298 |

FOREIGN PATENT DOCUMENTS

| 0175591 | 9/1985 | European Pat. Off. . |
| 0225195 | 6/1987 | European Pat. Off. . |
| 0248335 | 12/1987 | European Pat. Off. . |
| 3500909 | 7/1986 | Fed. Rep. of Germany . |
| 3506446 | 8/1986 | Fed. Rep. of Germany . |
| 240385 | 10/1986 | German Democratic Rep. . |
| 61-215374 | 11/1986 | Japan . |
| 61-246168 | 11/1986 | Japan . |
| 62-71 | 1/1987 | Japan . |
| 62-155257 | 7/1987 | Japan . |

Primary Examiner—John S. Maples
Assistant Examiner—Shean C. Wu
Attorney, Agent, or Firm—Millen, White & Zelano

[57] ABSTRACT

Optically active nitrogen-containing heterocycles of the formula I according to claim 1 are suitable as components for ferroelectric liquid crystalline materials.

9 Claims, No Drawings

NITROGEN-CONTAINING HETEROCYCLES

This is a division of application Ser. No. 07/034,182 filed Dec. 24, 1986, now U.S. Pat. No. 4,834,904.

The invention relates to nitrogen-containing heterocycles of the formula I $$R^1-A^1-Z^1-A^2-R^2 \qquad \text{I}$$

in which
one of the radicals $R^1$ and $R^2$ is H, an unsubstituted or substituted alkyl group of 1-15 carbon atoms in which one or two non-adjacent $CH_2$ groups can also be replaced by at least one member of the group —O—, —CO—, —O—CO—, —CO—O— and —CH=CH—; F, Cl, Br, —Cn, —NCS or $R^3-(A^3)_p-Z^2$—, the other radical $R^1$ or $R^2$ is an optically active organic radical with an asymmetric carbon atom, $A^1$ is —A—, —$A^4-Z^3$—A— or —A—$Z^3-A^4$—, A is a 1,4-phenylene group in which at lest one CH group is replaced by N, $A^2$, $A^3$ and $R^4$ each are 1,4-phenylene which is unsubstituted or substituted by one or two F atoms and/or Cl atoms and/or $CH_3$ groups and/or CN groups, in which one or two CH groups can also be replaced by N atoms; 1,4-cyclohexylene in which one or two non-adjacent $CH_2$ groups can also be replaced by O atoms and/or S atoms; piperidine-1,4-diyl, 1,4-bicyclo(2,2,2)octylene; decanydronaphthalene-2,6-diyl which is unsubstituted or substituted by CN; or 1,2,3,4-tetrahydronaphthalene-2,3-diyl, $Z^1$, $Z^2$ and $Z^3$ each are —CO—O, —O—CO—, —OCH$_2$—, —CH$_2$O—, —CH$_2$CH$_2$—, substituted ethylene or a single bond, $R^3$ is H; an unsubstituted or substituted alkyl group of 1-15 carbon atoms in which one or two non-adjacent $CH_2$ groups can also be replaced by a member of the group —O—, —CO—, —O—CO—, —CO—O and —CH=CH—; F, Cl, Br, —NCS or —CN, and p is 1 or 2, in which the groups $A^3$ can be the same or can differ from each other, when p=2, with the proviso that when A=pyrimidine-2,5-diyl, one of the radicals $R^1$ and $R^2$ is an optically active organic radical and the other radical $R^1$ or $R^2$ is an unsubstituted or substituted alkyl group of 1-15 carbon atoms, in which one or two non-adjacent $CH_2$ groups can also be replaced by at least one member of the group —O—, —CO—, —O—CO—, —CO—O— and —CH=CH—.

For the sake of simplicity, in the following text Cy is a 1,4-cyclohexylene group, Dio is a 1,3-dioxane-2,5-diyl group, Dit is a 1,3-dithiane-2,5-diyl group, Bi is a 1,4-bicyclo(2,2,2)octylene group, Phe is a 1,4-phenylene group and Pyr is a 1,4-phenylene group in which at least one CH group is replaced by N, in which these groups, in particular Cy and Phe can be unsubstituted or substituted by one or two F and/or Cl atoms and/or $CH_3$ groups and/or CN groups.

Similar compounds are known from, for example, EP-OS 0 131 373. However, in contrast to the above, the compounds disclosed therein do not contain in nitrogen-containing heterocyclic rings.

The compounds of the formula I can be used, like similar compounds, as chiral dopants for liquid crystalline phases, in particular as components of ferroelectric liquid crystalline phases. These phases are suitable for displays, which are based on the principle of the twisted cell (TN displays), the guest-host effect, the effect of the deformation of aligned phases or the effect of dynamic scattering, in particular, however, for ferroelectric displays, for example in accordance with N. A. Clark and S. T. Lagerwall, Applied Phys. Lett. 36,899 (1980).

The invention was based on the object of finding new stable liquid crystalline or mesogenic compounds that would be suitable as components of such phases.

It has been found that the compounds of the formula I are highly suitable as components of liquid crystalline phases. In particular, they can be used for preparing stable chiral $S_c$ phases in a temperature range favourable for electrooptical applications.

On adding compounds of the formula I to non-polar liquid crystalline phases, it was found, surprisingly, that even relatively small additions can significantly increase spontaneous polarization.

In addition, by providing the compounds of the formula I the range of liquid crystalline substances that are suitable for the preparation of ferroelectric mixtures from various points of view relating to application, has in general been substantially broadened.

The compounds of the formula I have a wide range of applications. Depending on the choice of substituents, these compounds can serve as base materials which form the predominant part of liquid crystalline phases; however, compounds of the formula I can be treated with liquid crystalline base materials from other compound classes in order to vary, for example, the dielectric and/or optical anisotropy and/or the spontaneous polarization of such a phase. Furthermore, the compounds of the formula I are suitable as intermediate products for the preparation of other substances that can be utilized as components of liquid crystalline phases.

When pure, the comopunds of formula I are colourless and form liquid crystalline mesophases in a temperature range favourable for electro-optical applications. They are very stable against the action of chemicals, heat and light.

The invention thus relates to the compounds of the formula I as well as the use of the compounds of the formula I as components of liquid crystalline phases. In addition, the invention relates to liquid crystalline phases, in particular ferro-electric liquid crystalline phases, containing at least one compound of the formula I as well as liquid crystal display elements, in particular electro-optical display elements, comprising such phases.

In the preceding and in the following, $R^1$, $R^2$, $R^3$, A, $A^1$, $A^2$, $A^3$, $A^4$, $Z^1$, $Z^2$, $Z^3$ and p have the meaning given, unless expressly indicated otherwise.

Accordingly, the compounds of the formula I comprise in particular compounds of the partial formulae I1 and I2 (with two rings), I3-I20 (with 3 rings), I21-I71 (with 4 rings), as well as I72-I94 (with 5 rings):

| | |
|---|---|
| $R^1-A-A^2-R^2$ | I1 |
| $R^1-A-Z^1-A^2-R^2$ | I2 |
| $R^1-A^4-A-A^2-R^2$ | I3 |
| $R^1-A-A^4-A^2-R^2$ | I4 |
| $R^3-A^3-A-A^2-R^2$ | I5 |
| $R^1-A-A^2-A^3-R^3$ | I6 |

| | |
|---|---|
| $R^1-A^4-Z^3-A-A^2-R^2$ | I7 |
| $R^1-A-Z^3-A^4-A^2-R^2$ | I8 |
| $R^1-A-Z^1-A^2-A^3-R^3$ | I9 |
| $R^1-A^4-Z^3-A-A^2-R^2$ | I10 |
| $R^1-A-Z^3-A^4-A^2-R^2$ | I11 |
| $R^1-A^4-A-Z^1-A^2-R^2$ | I12 |
| $R^1-A-A^4-Z^1-A^2-R^2$ | I13 |
| $R^3-A^3-A-Z^1-A^2-R^2$ | I14 |
| $R^1-A-A^2-Z^2-A^3-R^3$ | I15 |
| $R^3-A^3-Z^2-A-A^2-R^2$ | I16 |
| $R^3-A^3-Z^2-A-Z^1-Z^2-R^2$ | I17 |
| $R^1-A-Z^1-A^2-Z^2-A^3-R^3$ | I18 |
| $R^1-A^4-Z^3-A-Z^1-A^2-R^2$ | I19 |
| $R^1-A-Z^3-A^4-Z^1-A^2-R^2$ | I20 |
| $R^3-A^3-A^4-A-A^2-R^2$ | I21 |
| $R^3-A^3-A-A^4-A^2-R^2$ | I22 |
| $R^1-A^4-A-A^2-A^3-R^3$ | I23 |
| $R^1-A-A^4-A^2-A^3-R^3$ | I24 |
| $R^3-A^3-A-A^2-A^3-R^3$ | I25 |
| $R^3-A^3-A^3-A-A^2-R^3$ | I26 |
| $R^1-A-A^2-A^3-A^3-R^3$ | I27 |
| $R^3-A^3-Z^2-A-A^2-A^3-R^3$ | I28 |
| $R^3-A^3-A-Z^1-A^2-A^3-R^3$ | I29 |
| $R^3-A^3-A-Z^1-A^2-A^3-R^3$ | I30 |
| $R^3-A^3-A-A^2-Z^2-A^3-R^3$ | I31 |
| $R^1-A-A^4-Z^1-A^2-A^3-R^3$ | I32 |
| $R^1-A^4-A-Z^1-Z^2-A^3-R^3$ | I33 |
| $R^3-A^3-A^4-A-Z^1-A^2-R^2$ | I34 |
| $R^3-A^3-A-A^4-Z^1-A^2-R^2$ | I35 |
| $R^1-A^4-A-A^2-Z^2-A^3-R^3$ | I36 |
| $R^1-A-A^4-A^2-Z^2-A^3-R^3$ | I37 |
| $R^3-A^3-Z^2-A^4-A-A^2-R^2$ | I38 |
| $R^3-A^3-Z^2-A-A^4-A^2-R^2$ | I39 |
| $R^3-A^3-A-A^2-Z^2-A^3-R^3$ | I40 |
| $R^3-A^3-Z^2-A-A^2-A^3-R^3$ | I41 |
| $R^3-A^3-A-A-Z^1-A^2-R^2$ | I42 |
| $R^3-A^3-A^4-Z^3-A-A^2-R^2$ | I43 |
| $R^3-A^3-A-Z^3-A^4-A^2-R^2$ | I44 |
| $R^1-A-A^2-Z^2-A^3-A^3-R^3$ | I45 |
| $R^1-A^4-Z^3-A-A^2-A^3-R^3$ | I46 |
| $R^1-A-Z^3-A^4-A^2-A^3-R^3$ | I47 |
| $R^3-A^3-A^3-Z^2-A-A^2-R^2$ | I48 |
| $R^1-A-Z^1-A^2-A^3-A^3-R^3$ | I49 |
| $R^3-A^3-Z^2-A^4-A-Z^1-A^2-R^2$ | I50 |
| $R^3-A^3-Z^2-A-A^4-Z^1-A^2-R^2$ | I51 |
| $R^1-A^4-A-Z^1-A^2-Z^2-A^3-R^3$ | I52 |
| $R^1-A-A^4-Z^1-A^2-Z^2-A^3-R^3$ | I53 |
| $R^3-A^3-A-Z^1-A^2-Z^2-A^3-R^3$ | I54 |
| $R^3-A^3-Z^2-A-A^2-Z^2-A^3-R^3$ | I55 |
| $R^3-A^3-Z^2-A-Z^1-A^2-A^3-R^3$ | I56 |
| $R^3-A^3-A^4-Z^3-A-Z^1-A^2-R^2$ | I57 |
| $R^3-A^3-A-Z^3-A^4-Z^1-A^2-R^2$ | I58 |
| $R^1-A^4-Z^3-A-A^2-Z^2-A^3-R^3$ | I59 |
| $R^1-A-Z^3-A^4-A^2-Z^2-A^3-R^3$ | I60 |
| $R^3-A^3-Z^2-A^4-Z^3-A-A^2-R^2$ | I61 |
| $R^3-A^3-Z^2-A-Z^3-A^4-A^2-R^2$ | I62 |
| $R^1-A^4-Z^3-A-Z^1-A^2-A^3-R^3$ | I63 |
| $R^1-A-Z^3-A^4-Z^1-A^2-A^3-R^3$ | I64 |
| $R^3-A^3-A^3-Z^2-A-Z^1-A^2-R^2$ | I65 |
| $R^1-A-Z^1-A^2-Z^2-A^3-A^3-R^3$ | I66 |
| $R^3-A^3-Z^2-A-Z^1-A^2-Z^2-R^3$ | I67 |
| $R^3-A^3-Z^2-A^4-Z^3-A-Z^1-A^2-R^2$ | I68 |
| $R^3-A^3-Z^2-A-Z^3-A^4-Z^1-A^2-R^2$ | I69 |
| $R^1-A^4-Z^3-A-Z^1-A^2-Z^2-A^3-R^3$ | I70 |
| $R^1-A-Z^3-A^4-Z^1-A^2-Z^2-A^3-R^3$ | I71 |
| $R^3-A^3-A^4-A-A^2-A^3-R^3$ | I72 |
| $R^3-A^3-A-A^4-A^2-A^3-R^3$ | I73 |
| $R^3-A^3-A^4-A-A^2-A^3-R^3$ | I74 |
| $R^3-A^3-A-A^4-A^2-A^3-R^3$ | I75 |
| $R^1-A-A^4-A^2-A^3-A^3-R^3$ | I76 |
| $R^3-A^3-A^4-A-A^2-Z^2-A^3-R^3$ | I77 |
| $R^3-A^3-A-A^4-A^2-Z^2-A^3-A^3$ | I78 |
| $R^3-A^3-A^4-A-Z^1-A^2-A^3-R^3$ | I79 |
| $R^3-A^3-A-A^4-Z^1-A^2-A^3-R^3$ | I80 |
| $R^3-A^3-Z^2-A^4-A-A^2-A^3-R^3$ | I81 |

$R^3-A^3-Z^2-A-A^4-A^2-A^3-R^3$    I82

$R^3-A^3-A^4-A-Z^1-A^2-Z^2-A^3-R^3$   I83

$R^3-A^3-A-A^4-Z^1-A^2-Z^2-A^3-R^3$   I84

$R^3-A^3-Z^2-A^4-A-A^2-Z^2-A^3-R^3$   I85

$R^3-A^3-Z^2-A-A^4-A^2-Z^2-A^3-R^3$   I86

$R^3-A^3-Z^2-A^4-A-Z^1-A^2-A^3-R^3$   I87

$R^3-A^3-Z^2-A-A^4-Z^1-A^2-A^3-R^3$   I88

$R^3-A^3-Z^2-A^4-A-Z^1-A^2-Z^2-A^3-R^3$  I89

$R^3-A^3-Z^2-A-A^4-Z^1-A^2-Z^2-A^3-R^3$  I90

$R^1-A^3-Z^2-A-Z^1-A^2-Z^2-A^3-A^3-R^3$  I91

$R^1-A-Z^3-A^4-Z^1-A^2-Z^2-A^3-A^3-R^3$  I92

$R^3-A^3-A^3-Z^2-A-Z^1-A^2-Z^2-A^3-R^3$  I93

$R^3-A^3-Z^2-A-Z^1-A^2-Z^2-A^3-A^3-R^3$  I94

Particularly preferred, relatively small groups of compounds are those of the formulae I001 to I022:

$R^1-Phe-Z^1-A-R^2$    I001

$R^1-Cy-Z^1-A-R^2$    I002

$R^1-Dio-Z^1-A-R^2$    I003

$R^1-Pip-Z^1-A-R^2$    I004

$R^1-Bi-Z^1-A-R^2$    I005

$R^1-Bi-Z^1-A-R^2$    I006

$R^1-Phe-Z^1-A-R^2$    I007

$R^1-Dio-Z^1-A-Z^2-Cy-R^2$  I008

$R^1-Cy-Z^1-A-Z^2-Phe-R^2$  I009

$R^1-Cy-Z^1-A-Z^2-Cy-R^2$  I010

$R^1-Phe-Phe-Z^1-A-R^2$   I011

$R^1-Phe-Cy-Z^1-A-R^2$   I012

$R^1-Cy-Phe-Z^1-A-R^2$   I013

$R^1-Cy-Cy-Z^1-A-R^2$   I014

$R^1-Phe-Phe-Z^1-A-Z^2-Phe-R^2$  I015

$R^1-Phe-Phe-Z^1-A-Z^2-Cy-R^2$  I016

$R^1-Phe-Cy-Z^1-A-Z^2-Phe-R^2$  I017

$R^1-Phe-Cy-Z^1-A-Z^2-Cy-R^2$  I018

$R^1-Cy-Phe-Z^1-A-Z^2-Phe-R^2$  I019

$R^1-Cy-Phe-Z^1-A-Z^2-Cy-R^2$  I020

$R^1-Cy-Cy-Z^1-A-Z^2-Phe-R^2$  I021

$R^1-Cy-Cy-Z^1-A-Z^2-Cy-R^2$  I022

In the compounds of the above partial formulae I001 to I022, $Z^1$ and $Z^2$ are each, preferably, a single bond.

The partial formulae I001, I009 and I013 are especially preferred.

In the compounds of the preceding and following formulae, a substituted alkyl group or substituted ethylene represents an alkyl group or —CH$_2$CH$_2$— (ethylene) group which is monosubstituted or polysubstituted on different carbon atoms by halogen, preferably fluorine or chlorine, or by CN. Preferably, the alkyl group is only monosubstituted by halogen or CN. The carbon atom linked to halogen or CN is preferably an asymmetric carbon atom.

One of the radicals $R^1$ and $R^2$ is, preferably, alkyl, —O— alkyl or oxaalkyl, —COO—alkyl, —OCO—alkyl, —CO—alkyl or alkenyl.

The alkenyl groups in the compounds of the formula I are preferably straight-chain trans-alkenyl groups of the formula

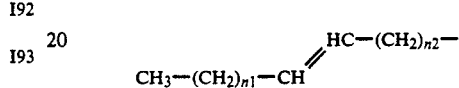

in which
n2 is 0 to 10, preferably 2 to 10, and
n1 is 0 to 5, preferably 0.

The alkyl radicals in which one ("alkoxy" or "oxaalkyl") or two ("alkoxyalkoxy" or "dioxaalkyl") nonadjacent CH$_2$ groups can be replaced by 0 atoms, can be straight-chain or branched. They are preferably straight-chain, have 2, 3, 4, 5, 6, 7, 8, 9, 10, 11, 12, 13, 14 or 15 carbon atoms and therefore represent preferably 2-oxapropyl (=methoxymethyl), 2- (=ethoxymethyl) or 3-oxabutyl (=2-methoxymethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 8-oxaoctyl, 2-, 3-, 4-, 5-, 6- or 9-oxanonyl, 2-, 3-, 4-, 5-, 6- or 10-oxadecyl, 2-, 3-, 4-, 5-, 6- or 11-oxaundecyl, 2-, 3-, 4-, 5-, 6- or 12-oxadodecyl 2-, 3-, 4-, 5-, 6- or 13-oxatridecyl, 2-, 3-, 4-, 5-, 6- or 14-oxatetradecyl, 2-, 3-, 4-, 5-, 6- or 15-oxapentadecyl, 1,3-dioxabutyl (=methoxymethoxy), 1,3-, 1,4- or 2,4-dioxahexyl, 1,3-, 1,4-, 1,5-, 1,6-, 2,4-, 2,5-, 2,6-, 3,5-, 3,6- or 4,6-dioxaheptyl.

The alyl radical in the groups $R^1$ and/or $R^2$ can be straight-chain or branched. They are preferably straight-chain, possess 2, 3, 4, 5, 6, 7, 8, 9, 10, 11 or 12, 13, 14 or ob 15 carbon atoms and are therefore preferably ethyl, propyl, butyl, pentyl, hexyl, heptyl, octyl, nonyl, decyl, undecyl, dodecyl, tridecyl, tetradecyl or pentadecyl, as well as methyl.

The other radical $R^1$ or $R^2$ is an optically active organic radical with an asymmetric carbon atom. The asymmetric carbon atom is preferably linked to two differently substituted carbon atoms, a hydrogen atom and a substituent selected from the group halogen (preferably F, Cl or Br), alkyl or alkoxy with 1 to 5 carbon atoms in each case, and CN. The optically active organic radical has preferably the formula

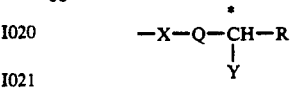

wherein
X is —CO—O—, —O—CO—, —O—CO—O—, —CO—, —O—, —S—, —CH=CH—, —CH=CH—COO— or a single bond, Q is alkylene with 1 to 5 carbon atoms, in which a $CH_2$ group not linked with X can also be replaced by —O—, —CO—, —O—CO—, —CO—O— or —CH=CH—, or a single bond, Y is CN, halogen, methyl or methoxy and R is an alkyl group of 1 to 18 carbon atoms that is different from Y, in which one or two non-adjacent $CH_2$ groups can also be replaced by —O—, —CO—, —O—CO—, —CO—O— and/or —CH=CH—.

X is preferably —CO—O—, —O—CO—, —O—, —CH=CH—COO— (trans) or a single bond. —O—, —CO—O— and —O—CO— are particularly preferred.

Q is preferably alkylene of 1 to 5 carbon atoms or a single bond, —$CH_2$—, —$CH_2CH_2$— or a single bond being particularly preferred.

Y is preferably $CH_3$, —CN or Cl, —CN or Cl being particularly preferred.

R is preferably straight-chain alkyl of 1 to 10, in particular of 1 to 7, carbon atoms, in which, if desired, the $CH_2$ group linked to the asymmetric carbon atom can be replaced by —O—, —O—CO— or —CO—O—.

$R^2$ in formula I is preferably the optically active radical.

$A^2$, $A^3$ and $A^4$ are preferably, independently of one another, Cy, Dio or Phe, furthermore, preferably, Dit, Pyr or Pip; the compound of the formula I does not contain, preferably, more than one of the radicals Dio, Dit, Pip, Bi, Pyn or Pyr.

$A^1$ is preferably —A— or —$A^4$—$Z^3$—A—.

A is preferably pyrimidine-2,5-diyl, pyridine-2,5-diyl, pyridazine-3,6-diyl or pyrazine-2,5-diyl, pyrimidine-2,5-diyl or pyridine-2,5-diyl being particularly preferred.

$Z^1$, $Z^2$ and $Z^3$ are preferably, independently of one another, —O—CO—, —CO—O— groups or single bonds.

—$A^1$—$Z^1$—$A^2$— is preferably a structural element selected from the group of the formulae 1 to 4:

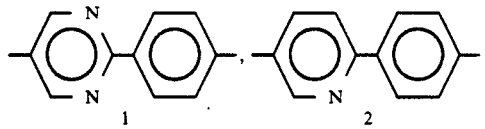
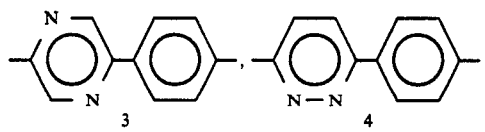

Groups of the formulae 1 and 2 are particularly preferred.

Among the compounds of the formula I as well as among the preceding and following partial formulae, those are preferred in which at least one of the radicals contained therein possesses one of the given preferred meanings. Relatively small groups of compounds which are particularly preferred are those of the formulae I023 to I031:

| | |
|---|---|
| R°—Pyr—Phe—R* | I023 |
| R°—Pyr—Cy—R* | I024 |
| R°—Pyr—CH₂CH₂—Cy—R* | I025 |
| R°—Pyr—COO—Phe—R* | I026 |
| R°—Pyr—OCO—Phe—R* | I027 |
| R°—Pyr—COO—Cy—R* | I028 |
| R°—Pyr—Phe—CH₂CH₂—Cy—R* | I029 |
| R°—Pyr—Phe—O—CH₂—Cy—R* | I030 |
| R°—Pyr—Phe—O—Ch₂—Phe—R* | I031 | in which R° is preferably straight-chain alkyl or alkoxy of, in each case, 2 to 12 carbon atoms, Pyr is preferably pyrimidine-2,5-diyl and R* preferably has one of the preferred meanings indicated for the optically active organic radical.

Further relatively small groups of compounds which are preferred are those of the formulae I032 to I096:

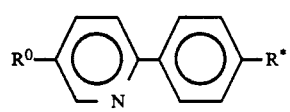 I032

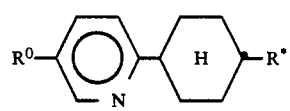 I033

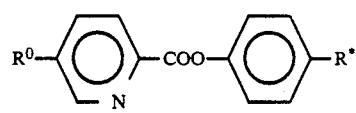 I034a

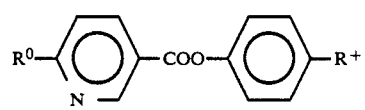 I034b

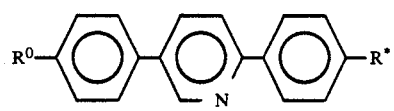 I035

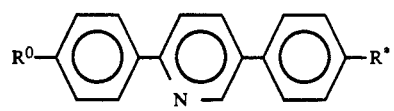 I036

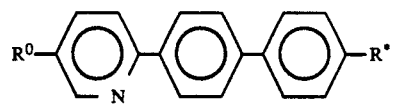 I037

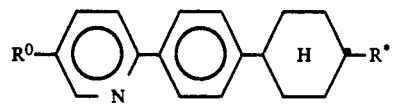 I038

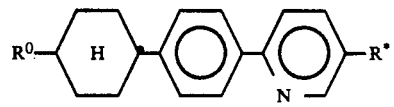 I039

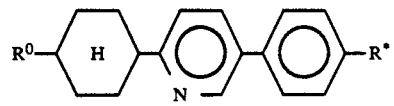 I040

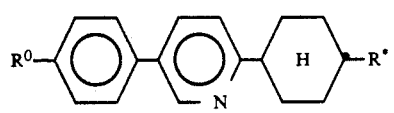 I041
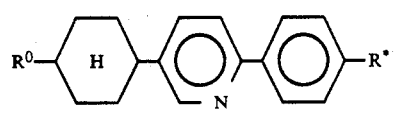 I042
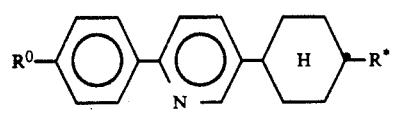 I043
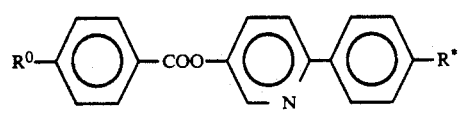 I044
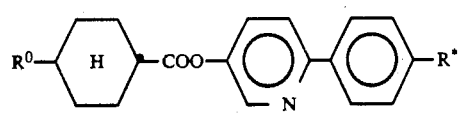 I045
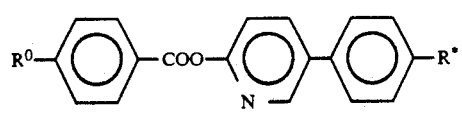 I046
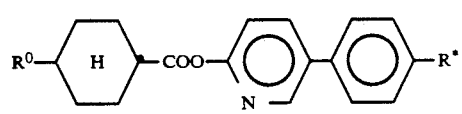 I047
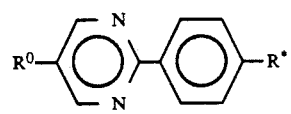 I048
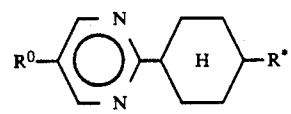 I049
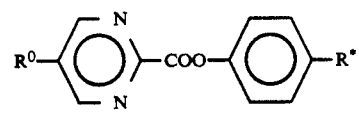 I050
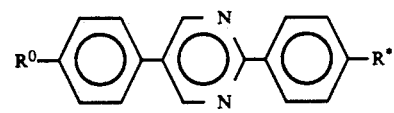 I051
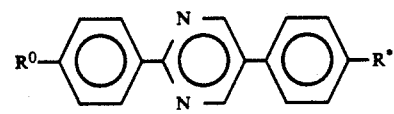 I052
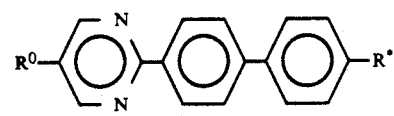 I053
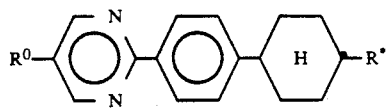 I054
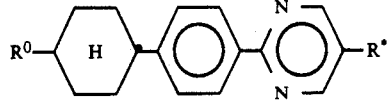 I055
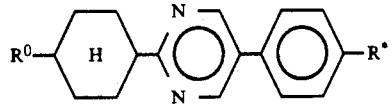 I056
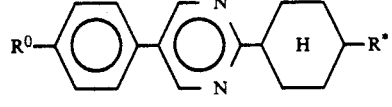 I057
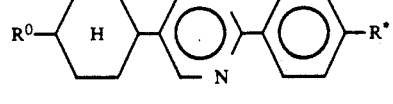 I058
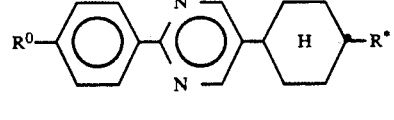 I059
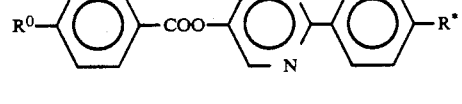 I060
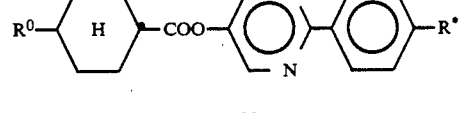 I061
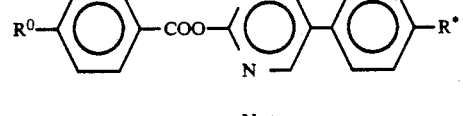 I062
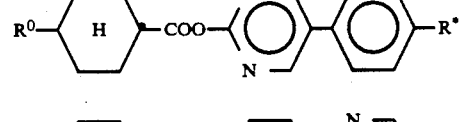 I063
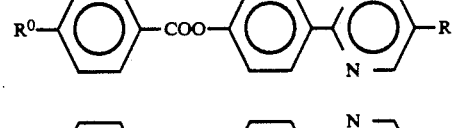 I064
 I065
 I066

11
-continued
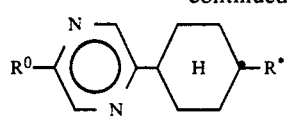 I067
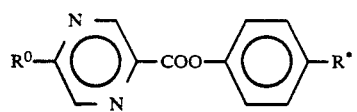 I068
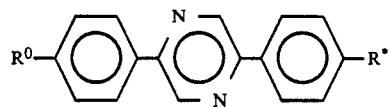 I069
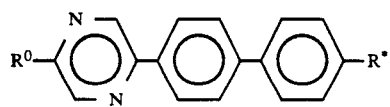 I070
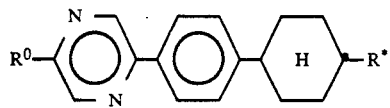 I071
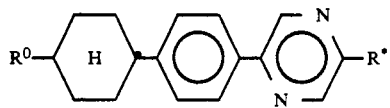 I072
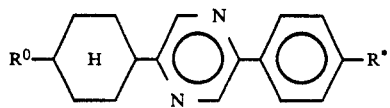 I073
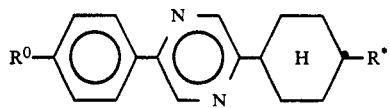 I074
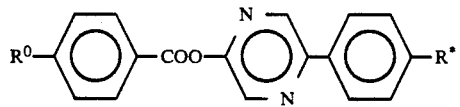 I075
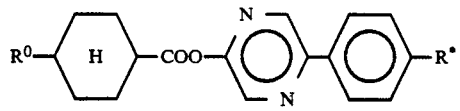 I078
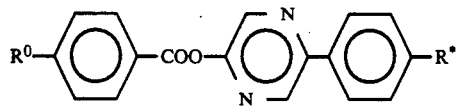 I079
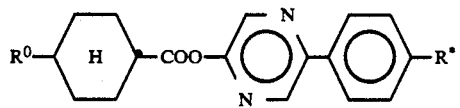 I080
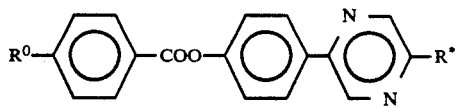 I081
12
-continued
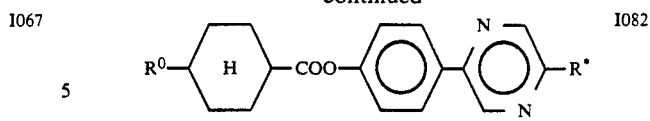 I082
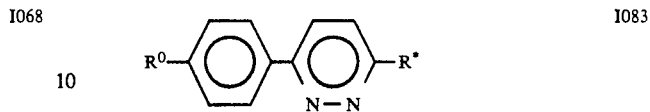 I083
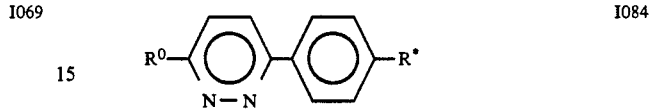 I084
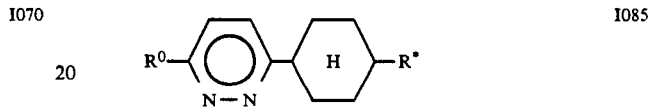 I085
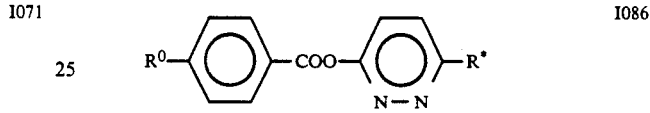 I086
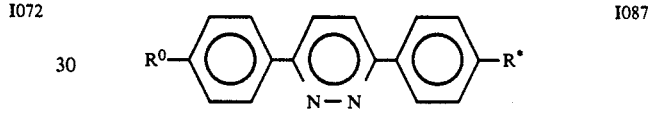 I087
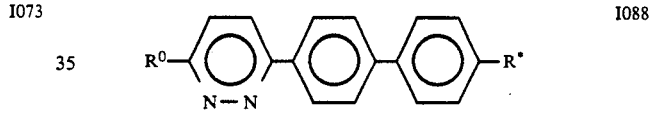 I088
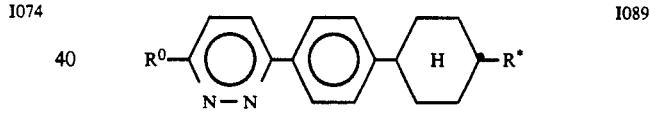 I089
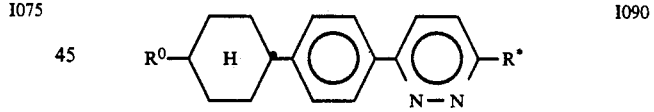 I090
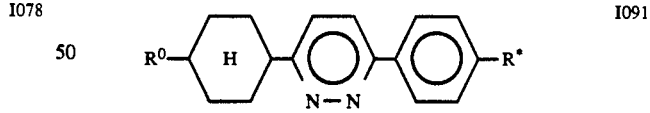 I091
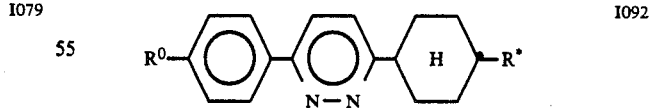 I092
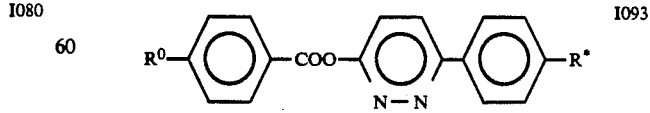 I093
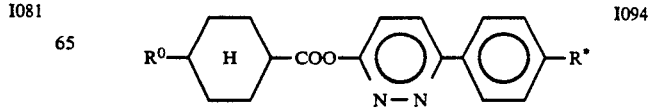 I094

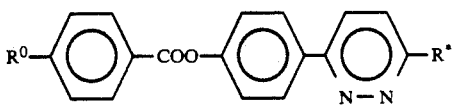

1095

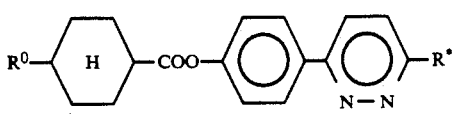

1096

Other particularly preferred pyridine compounds are those of the formulae I097 to I117:

| | |
|---|---|
| R*—Pyr—Bi—R* | I097 |
| R*—Bi—Pyr—R* | I098 |
| R*—Pyr—OCO—Phe—R* | I099 |
| R*—Phe—COO—Pyr—R* | I100 |
| R*—Pyr—Phe—Cy—R* | I101 |
| R*—Cy—Phe—Pyr—R* | I102 |
| R*—Pyr—Phe—Phe—R* | I103 |
| R*—Phe—Phe—Pyr—R* | I104 |
| R*—Pyr—Phe—Bi—R* | I105 |
| R*—Bi—Phe—Pyr—R* | I106 |
| R*—Pyr—Bi—Phe—R* | I107 |
| R*—Phe—Bi—Pyr—R* | I108 |
| R*—Pyr—Cy—Cy—R* | I109 |
| R*—Cy—Cy—Pyr—R* | I110 |
| R*—Cy—Pyr—Cy—R* | I111 |
| R*—Pyr—Phe—CH$_2$CH$_2$—Cy—R* | I112 |
| R*—Cy—CH$_2$CH$_2$—Phe—Pyr—R* | I113 |
| R*—Pyr—Cy—CH$_2$CH$_2$—Cy—R* | I114 |
| R*—Cy—CH$_2$CH$_2$—Cy—Pyr—R* | I115 |
| R*—Phe—Pyr—Cy—R* | I116 |
| R*—Cy—Pyr—Phe—R* | I117 |

In the formulae I097 to I117, Pyr denotes pyridine-2,5-diyl.

Particularly preferred are optically active pyridine compounds of the formula I'

$$R^1—A^1—Z^1—A^2—R^2 \quad I'$$

in which
one of the radical $R^1$ and $R^2$ is H; an unsubstituted or substituted alkyl group of 1-15 carbon atoms in which one or two non-adjacent CH$_2$ groups can also be replaced by at least one member of the groups —O—, —CO—, —O—CO—, —CO—O— and —CH=CH—; F, Cl, Br, —CH, —NCS or $R^3$—$(A^3)_p$—$Z^2$—, the other radical $R^1$ or $R^2$ is an optically active organic radical with an asymmetric carbon atom,
$A^1$ is —A—, —A$^4$—Z$^3$—A— or —A—Z$^3$—A$^4$—,
A is 2,5-pyridinediyl,
$A^2$, $A^3$ and $A^4$ each are 1,4-phenylene which is unsubstituted or substituted by one or two F atoms and/or Cl atoms and/or CH$_3$ group and/or CN groups, in which one or two CH groups can also be replaced by N atoms; 1,4-cyclohexylene in which one or two non-adjacent CH$_2$ groups can also be replaced by O atoms and/or S atoms; piperidine-1,4-diyl, 1,4-bicyclo(2,2,2)octylene, decahydronaphthalene-2,6-diyl which is unsubstituted or substituted by CN; or 1,2,3,4-tetrahydronaphthalene-2,6-diyl,
$Z^1$, $Z^2$ and $Z^3$ each are —CO—O, —O—CO—, —OCH$_2$—, —CH$_2$O—, —CH$_2$CH$_2$—, substituted ethylene or a single bond,
$R^3$ is H; an unsubstituted or substituted alkyl group of 1-15 carbon atoms in which one or two non-adjacent CH$_2$ groups can also be replaced by one member of the group —O—, —CO—, —O—CO—, —CO—O— and —CH=CH—; F, Cl, Br, —NCS or —CN, and
p is 1 or 2,
in which the groups $A^3$ can be the same or different from each other, when p=2, as well as liquid crystalline ferroelectric phases containing at lest one compound of the formula I' and electro-optical display elements comprising these phases. The preferred meanings given for formula I for $R^1$, $R^2$, $R^3$, $A^1$, $A^2$, $A^3$, $A^4$, $Z^1$, $Z^2$, $Z^3$ and p are also valid by analogy for compounds of the formula I'.

Of the compounds of the formula I, those stereoisomers are preferred in which the saturated rings (for example Cy, Dio, Dit) are trans-1,4-disubstituted.

When $R^1—A^1—Z^1—A^2—R^2 =$

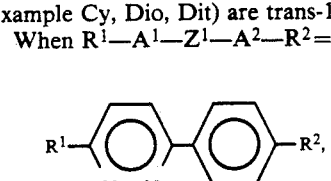

wherein
$R^1$ is an optically active alkoxy group with an asymmetric carbon atom, $R^2$ preferably denotes an unsubstituted or substituted alkyl group of 1-15 carbon atoms in which one or two non-adjacent CH$_2$ groups can also be replaced by at least one member of the group —CO—, —O—CO—, —CO—O and —CH=CH—; F, Cl, Br, —CN—, —NCS or $R^3$—$(A^3)_p$—$Z^2$—.

When $R^1—A^1—Z^1—A^2—R^2 =$

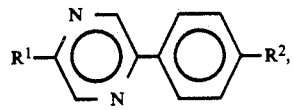

wherein
$R^2$ is an optically active alkoxy group with an asymmetric carbon atom, $R^1$ preferably denotes an unsubstituted or substituted alkyl group of 1-15 carbon atoms in which one or two non-adjacent CH$_2$ groups can also be replaced by —O— or —CH=CH—. An especially preferred meaning of $R^1$ is a straight-chain alkyl or alkoxy, in particular straight-chain alkyl, each of 5-12 carbon atoms.

When $R^1—A^1—Z^1—A^2—R^2 =$

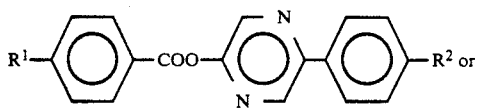

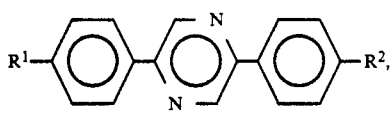

wherein $R^2$ is an optically active alkoxy group with an asymmetric carbon atom, $R^1$ preferably denotes an unsubstituted or substituted alkyl group of 1–15 carbon atoms in which two non-adjacent $CH_2$ groups are replaced by —O—, —CO—, —O—CO—, —CO—O— and/or —CH=CH—.

When A=

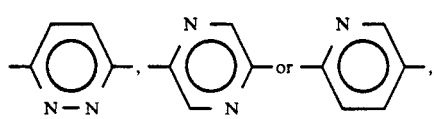

particularly when A=

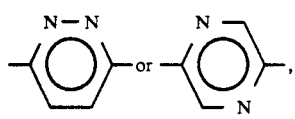

the optically active radical $R^1$ or $R^2$ preferably denotes an alkyl group in which two non-adjacent $CH_2$ groups are replaced by at least one member of the group —O—, —CO—, —O—CO—, —CO—O and —CH=CH—. Especially preferred optically active radicals correspond to the formula

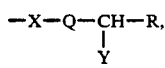

in which X denotes —O—, —CO—O— or —O—CO—, Q denotes —$CH_2$— or a single bond, Y denotes $CH_3$ and R denotes a straight-chain alkyl of 1 to 7 carbon atoms, in which the $CH_2$ group linked to the asymmetric carbon atoms is replaced by —O—, —CO—O— or —O—CO—.

The compounds of the formula I are prepared by methods known per se. These are described in the literature (for example in standard works such as Houben-Weyl, Methoden der Organischen Chemie, Georg-Thieme-Verlag, Stuttgart), under reaction conditions which are known and suitable for the named reactions. In this context, use can also be made of variants which are known per se and not referred to here in further detail.

The person skilled in the art can infer the corresponding synthesis methods, via routine methods, from the state of the art (for example German Offenlegungsschriften 2,344,732; 2,450,088; 2,429,093; 2,502,904; 2,636,684; 2,701,591 and 2,752,975 in respect of compounds with 1,4-cyclohexylene and 1,4-phenylene groups; German Patent 2,641,724 in respect of compounds with pyrimidine-2,5 diyl groups; German Offenlegungsschriften 2,944,905 and 3,227,916 in respect of compounds with 1,3-dioxane-2,5-diyl groups; East German Patent 160,061 in respect of compounds with 1,3-dithiane-2,5-diyl groups; U.S. Pat. Nos. 4,261,652 and 4,219,256 in respect of compounds with 1,4-bicyclo(2,2,2)-octylene groups; and German Offenlegungsschrift 3,201,721 in respect of compounds with —$CH_2$—$CH_2$ bridge members).

If desired, the starting materials can also be formed in situ, in such a way that they are not isolated from the reaction mixture, but immediately reacted further to form compounds of the formula I.

In general, two corresponding partial compounds (for example (1) and (2) (Scheme 1) or (3) and (4) (Scheme 2)) are condensed to give compounds of the formula I:

Scheme 1:

(1)        (2)

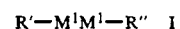

($M^1M^2 = A$)

Scheme 2:

(3)        (4)

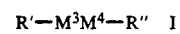

($M^3M^4 = Z$)

—$M^1L^1$ and —$M^2L^2$ are condensable building blocks, which corresponds to, for example, malonic acid derivatives (for example malonic dialdehyde), amidines, aldehydes, 1,3-propanediols and/or 1,3-propanedithiols. $L^1L^2$ are one or more split-off groups.

—$M^3L^3$ and —$M^4L^4$ are condensable building blocks, for example selected from the group —COOH, —COhalogen, —OH, —Ometal, —$CH_2$—halogen, —$CH_2$—metal, —$CH_2$—OH, —$CH_2$—O— metal, -metal and -halogen.

$L^3$ and $L^4$ are leaving groups. $L^3L^4$ is a split-off group, for example $H_2O$, H-halogen, metal-halogen.

In addition, to synthesize compounds of the formula I, appropriate intramolecular condensations can be carried out (for example condensation of 1,4-diketones with hydrazine (for example German Offenlegungsschrift 3,238,350) or reaction of a butadiene derivative with, for example, acetylene dicarboxylic acid derivatives (for example Japanese Published Applications 58-144,327 and 58-146,543)).

The starting materials are known or are obtainable by methods analogous to those used for the known compounds. The person skilled in the art can infer, via routine methods, the corresponding starting materials and/or methods for their synthesis from the state of the art.

In addition, the compounds of the formula I can be prepared by reducing a compound which otherwise corresponds to the formula I, but comprises one or more reducible groups and/or C—C bonds in place of hydrogen atoms.

Such reducible groups are preferably carbonyl groups, in particular keto groups, as well as, for example, free or esterified groups or aromatically bound halogen atoms. Preferred starting materials for the reduction correspond to the formula I, but can comprise, in place of a cyclohexane ring, a cyclohexene ring or a cyclohexanone ring, and/or in place of a —$CH_2CH_2$— group a —CH=CH—group, and/or in place of a —$CH_2$—group a —CO—group, and/or in place of an H atom a free or functionally (for example in the form of its p-toluenesulfonate) transformed OH group.

The reduction can take place by, for example, catalytic hydrogenation at temperatures between about 0° and about 200° and pressures between about 1 and 200 bar in an inert solvent, for example an alcohol such as methanol, ethanol or isopropranol (sic), an ether such as tetrahydrofuran (THF) or dioxane, an ester such as ethyl acetate, a carboxylic acid such as acetic acid, or a hydrocarbon such as cyclohexane. Suitable catalysts are, advantageously, noble metals such as Pt or Pd which can be used in the form of oxides (for example $PtO_2$, PdO), either on a carrier (for example Pd on carbon, calcium carbonate or strontium carbonate) or in finely divided form.

Ketones can also be reduced to the corresponding compounds of the formula I, which contain alkyl groups and/or —$CH_2CH_2$—bridges, by the method of Clemmensen (with zinc, zinc amalgam or tin and hydrochloric acid, conveniently in an aqueous alcoholic solution or in a heterogeneous phase with water/toluene at temperatures between about 80° and 120°) or that of Wolff-Kishner (with hydrazine, conveniently in the presence of an alkali such as KOH or NaOH in a high boiling solvent such as diethylene glycol or triethylene glycol at temperatures between about 100° and 200°).

Furthermore, reductions are possible with complex hydrides. For example, arylsulfonyloxy groups can be reductively removed with $LiAlH_4$, in particular p-toluenesulfonyloxymethyl groups can be reduced to methyl groups, conveniently in an inert solvent such as diethyl ether or THF at temperatures between about 0° and 100°. Double bonds can be hydrogenated with $NaBH_4$ or tributyl tin hydride in methanol (even in the presence of CN groups!); in this way, for example 1-cyano-cyclohexene derivatives give rise to the corresponding cyclohexane derivatives.

Esters of the formula I ($R^1$ and/or $R^2$=alkyl, in which one or two $CH_2$ groups are replaced by —O—CO— and/or —CO—O— groups, or $Z^1$ and/or $Z^2$=—CO—O— or —O—CO—) can also be obtained by esterification of the corresponding carboxylic acids (or their reactive derivatives) with alcohols or phenols (or their reactive derivatives).

Suitable reactive derivatives of the named carboxylic acids are in particular the acid halides, especially the chlorides and bromides, as well as the anhydrides, azides or esters, in particular alkyl esters with 1–4 carbon atoms in the alkyl group.

Suitable reactive derivatives of the named alcohols or phenols are in particular the corresponding metal alcoholates or phenolates, in particular those of an alkali metal such as Na or K.

The esterification is preferably carried out in the presence of an inert solvent. Suitable solvents are especially ethers such as diethyl ether, di-n-butyl ether, THF, dioxane or anisole; ketones such as acetone, butanone or cyclohexanone; amides such as DMF or phosphoric acid hexamethyltriamide; hydrocarbons such as DMF or phosphoric acid hexamethyltriamide; hydrocarbons such as benzene, toluene or xylene; halogenated hydrocarbons such as carbon tetrachloride or tetrachloroethylene, and Sulfoxides such as dimethyl sulfoxide or sulfolane. Solvents not miscible with water can at the same time be advantageously used for distilling off azeotropically water formed in the esterification. In some cases, an excess of an organic base, for example pyridine, quinoline or triethylamine, can be used as solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are usually terminated after 15 minutes to 48 hours.

Individually, the reaction conditions for the esterification depend to a large extent on the type of the starting materials used. Thus, a free carboxylic acid is reacted with a free alcohol or phenol usually in the presence of a strong acid, for example a mineral acid such as hydrochloric acid or sulfuric acid. A preferred reaction method is the reaction of an acid anhydride and especially an acid chloride with an alcohol, preferably in an alkaline medium, using as the bases especially alkali metal hydroxides, such as sodium or potassium hydroxide, alkali metal carbonates or bicarbonates such as sodium carbonate, sodium bicarbonate, potassium carbonate or potassium bicarbonate; alkali metal acetates such as sodium or potassium acetate; alkaline earth metal hydroxides such as calcium hydroxide; or organic bases such as triethylamine, pyridine, lutidine, collidine or quinoline. Another preferred embodiment of the esterification consists in first converting the alcohol or phenol to the sodium or potassium alcoholate or phenolate, for example by treatment with ethanolic sodium or potassium hydroxide solution, isolating the alcoholate or phenolate, suspending it together with sodium bicarbonate or potassium carbonate in acetone or diethyl ether with stirring, and treating this suspension with a solution of the acid chloride or anhydride in diethyl ether, acetone or DMF, conveniently at temperatures between about −25° and +20°.

Dioxane or dithiane derivatives of the formula I (in which one of the groups $A^1$ and/or $A^2$ and/or $A^3$ represents a 1,3-dioxane-2,5-diyl group or a 1,3-dithiane-2,5-diyl group) are conveniently prepared by reacting a corresponding aldehyde with a corresponding 1,3-diol or a corresponding 1,3-dithiol (or one of its reactive derivatives), preferably in the presence of an inert solvent such as benzene or toluene, and/or a catalyst, for example a strong acids such as sulfuric acid, benzenesulfonic or p-toluenesulfonic acid, at temperatures between about 20° and about 150°, preferably between 80° and 120°. The most suitable reactive derivatives of the starting materials are the acetals.

The aldehydes, 1,3-diols and 1,3-dithiols mentioned as well as their reactive derivatives are partly known, and partly can be prepared without difficulties by standard procedures of organic chemistry on the basis of compounds known in the literature. For example, aldehydes are obtainable by oxidation of the corresponding carboxylic acids or their derivatives, the diols by reduction of the corresponding diesters, and dithiols by reacting the corresponding dihalides with NaSH.

To prepare nitriles of the formula I (in which $R^1$ and/or $R^2$ are CN), the corresponding acid amides can be dehydrated. For example, the amides are obtainable from the corresponding esters or acid halides by reaction with ammonia. Suitable dehydrating agents are, for example, inorganic acid chloride such as $SOCl_2$, $PCl_3$, $PCl_5$, $POCl_3$, $SO_2Cl_2$, $COCl_2$, as well as $P_2O_5$, $P_2S_5$, $AlCl_3$ (for example as a double bond (sic) with NaCl), aromatic sulfonic acids and sulfonic acid halides. The reaction can take place in the presence or absence of an inert solvent at temperatures between about 0° and 150°; suitable solvents are, for example, bases such as pyridine or triethylamine, aromatic hydrocarbons such as benzene, toluene or xylene, or amides such as DMF.

To prepare the nitriles of the formula I mentioned above, the corresponding acid halides, preferably the chlorides, can be reacted with sulfamide, conveniently in an inert solvent such as tetramethylenesulfone, at temperatures between about 80° and 150°, preferably at 120°. The nitriles can be isolated direct after the usual working up.

Ethers of the formula I (in which $R^1$ and/or $R^2$ are an alkyl group in which one or two $CH_2$ groups are replaced by O atoms, and/or in which $Z^1$ and/or $Z^2$ is an $—OCH_2$ or a $—CH_2O—$ group) are obtainable by an etherification of the corresponding phenols, in which the hydroxy compound is conveniently first converted to a corresponding metal derivative, for example to the corresponding alkali metal alcoholate or alkali metal phenolate, by treatment with NaH, $NaNH_2$, NaOH, KOH, $Na_2CO_3$ or $K_2CO_3$. The alcoholate or phenolate can be reacted with the corresponding alkyl halide, alkylsulfonate or dialkylsulfate, conveniently in an inert solvent such as acetone, 1,2-dimethoxyethane, DMF or dimethyl sulfoxide or an excess of aqueous or aqueous-alcoholic NaOH or KOH at temperatures between about 20° and 100°.

The ferroelectric liquid crystalline phases according to the invention consist of 2 to 15, preferably 3 to 12 components, of which at least one is a compound of the formula I. The other components are preferably selected from compounds of the formulae II to IV,

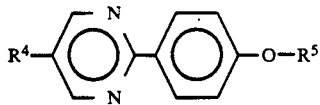   II

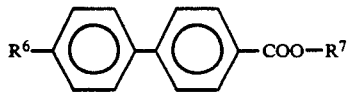   III

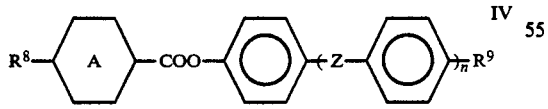   IV in which $R^4$ and $R^5$ each independently of one another are n-alkyl of 5 to 12 carbon atoms, and $R^6$, $R^7$, $R^8$ and $R^9$, each independently of one another, are straight-chain or branched, if desired chiral, alkyl, alkoxy, alkoxycarbonyl or alkanoyloxy groups of 5 to 12, especially of 6 to 10 carbon atoms. Ring A is 1,4-phenylene or trans-1,4-cyclohexylene. n is 0 or 1.

All these substances can be prepared in accordance with methods known from the literature.

In addition, the preferred ferroelectric phases according to the invention contain at least one compound of the formula V

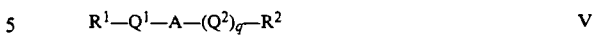   V in which $R^1$ and $R^2$ each independently of one another are straightchain alkyl group of 1 to 15 carbon atoms, in which one or more non-adjacent $CH_2$ groups can also be replaced by $—O—$, $—S—$, $—CO—$, $CHCH_3—O—$, $—CHCH_3—$, $—CH—$ halogen-, $CHCN—$, $—O—CO—$, $—O—COO—$, $—CO—O—$ and/or $—CH=CH—$, A is

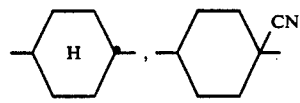

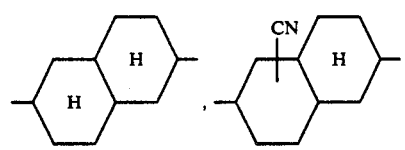

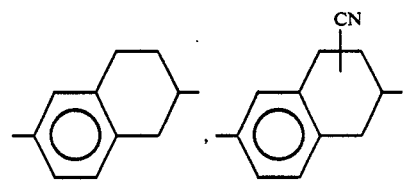

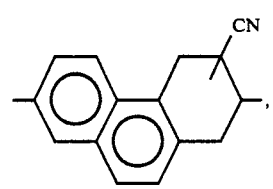

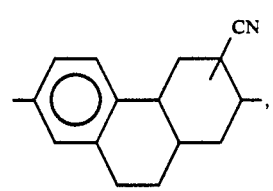

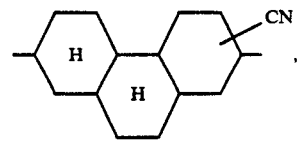

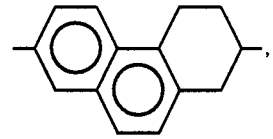

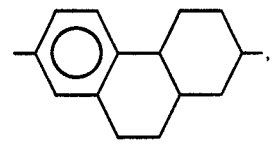

-continued

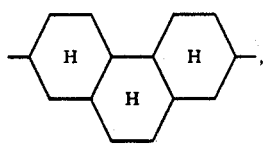

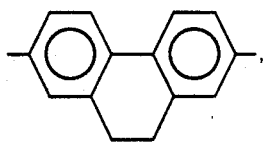

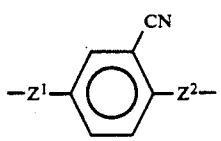

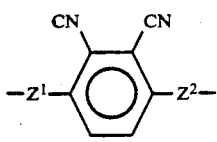

q is 0 or 1, $Q^1$ and $Q^2$ each independently of one another are —$(A^o$—$Z^o)_p$—, in which $A^o$ is 1,4-cyclohexylene which is unsubstituted or mono- or polysubstituted by halogen atoms, $CH_3$— and/or nitrile groups, in which one or two non-adjacent $CH_2$— groups can also be replaced by —O— and/or —S— and/or a

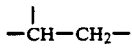

grouping can be replaced by

or is, 1,4-phenylene which is unsubstituted or mono- or polysubstituted by halogen atoms, $CH_3$— and/or nitrile groups, in which one or more CH— groups can also be replaced by N (Ph), one of the radicals $A^o$ also being 2,6-naphthylene (Na) or tetrahydro-2,6-naphthylene (4H—Na), if desired substituted by halogen or CN, $Z^o$, $Z^1$ and $Z^2$ each independently of one another are —CO—O—, —O—CO—, —$CH_2O$—, $OCH_2$—, —$CH_2CH_2$—, —$CHCNCH_2$—, —$CH_2$—CHCN— or a single bond, and p is 1, 2 or 3, or is 0 if A denotes tetra- or octaphenanthrene, and if A=

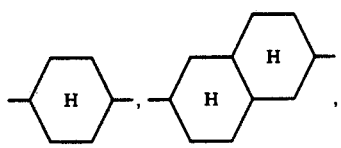

-continued

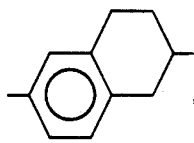

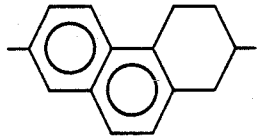

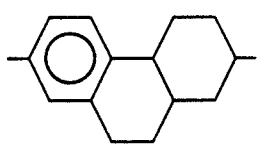

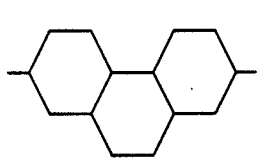

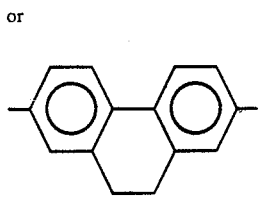

or

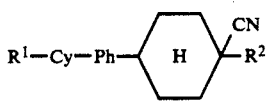

at least one group $Z^o$ is —$CHCNCH_2$— or —$CH_2CH$-CN— and/or in at least one of the groups $R^1$ and $R^2$, at least one $CH_2$ group is substituted by —CHCN—.

The compounds of the formula V can possess straight-chain on branched wing groups $R^1$ and/or $R^2$. Compounds with branched wing groups can be used in the form of the racemate or as optically active compounds. Achiral base mixtures of compounds of the formula V and, if desired, further achiral components, can be doped with chiral compounds of the formula I or, additionally, with other chiral compounds, in order to obtain chirally tilted smectic phases.

Smaller groups of compounds which are especially preferred are those of the formulae V1 to V18:

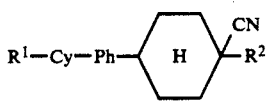  V1

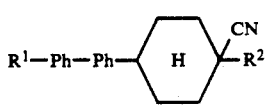  V2

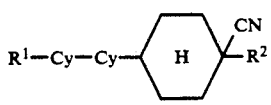  V3

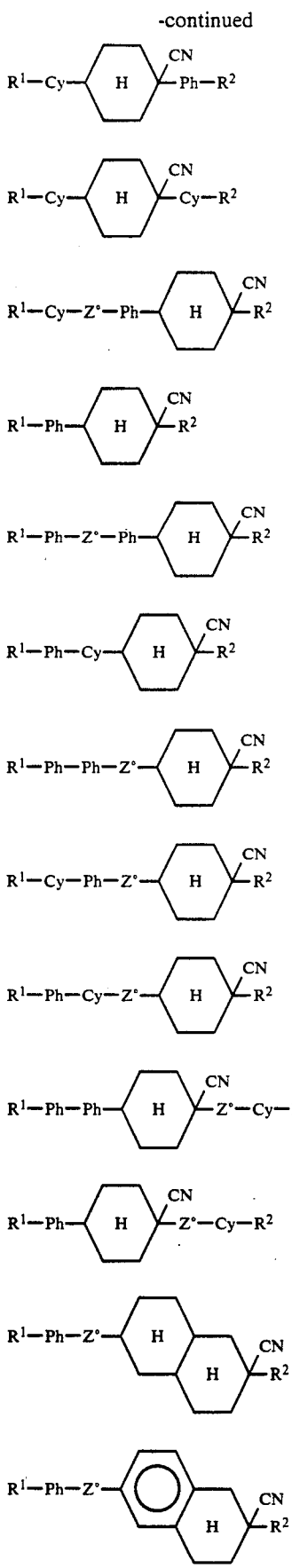

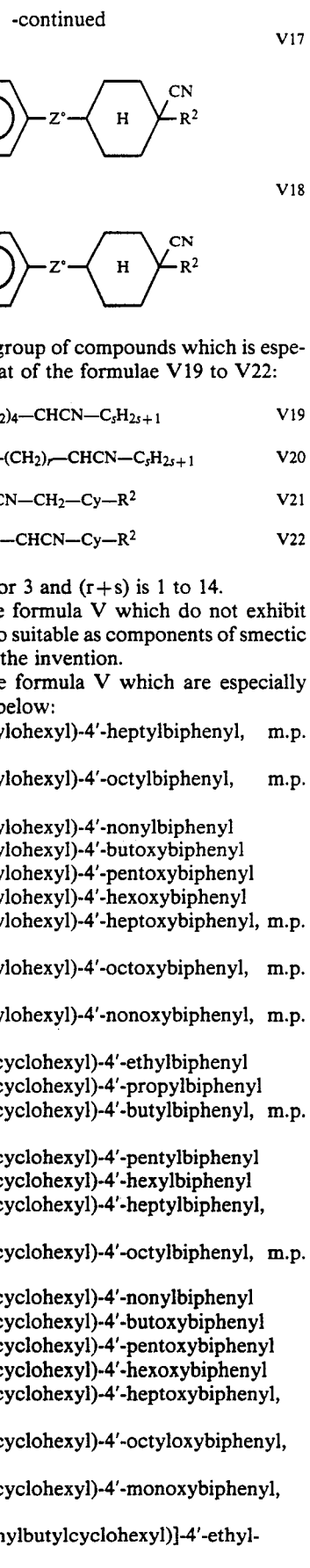

A further smaller group of compounds which is especially preferred is that of the formulae V19 to V22:

$R^1-A^o-Cy-(CH_2)_4-CHCN-C_sH_{2s+1}$   V19

$R^1-A^o-A^o-Cy-(CH_2)_r-CHCN-C_sH_{2s+1}$   V20

$R^1-A^o-A^o-CHCN-CH_2-Cy-R^2$   V21

$R^1-A^o-A^o-CH_2-CHCN-Cy-R^2$   V22 in which r is 0, 1, 2 or 3 and (r+s) is 1 to 14.

Compounds of the formula V which do not exhibit any $S_C$ phases, are also suitable as components of smectic phases according to the invention.

Compounds of the formula V which are especially preferred are given below:

4-(4-Cyano-4-butylcylohexyl)-4'-heptylbiphenyl, m.p. 56°, c.p. 122°
4-(4-Cyano-4-butylcylohexyl)-4'-octylbiphenyl, m.p. 42°, c.p. 118°
4-(4-Cyano-4-butylcylohexyl)-4'-nonylbiphenyl
4-(4-Cyano-4-butylcylohexyl)-4'-butoxybiphenyl
4-(4-Cyano-4-butylcylohexyl)-4'-pentoxybiphenyl
4-(4-Cyano-4-butylcylohexyl)-4'-hexoxybiphenyl
4-(4-Cyano-4-butylcylohexyl)-4'-heptoxybiphenyl, m.p. 93°. c.p. 156°
4-(4-Cyano-4-butylcylohexyl)-4'-octoxybiphenyl, m.p. 30°, c.p. 154°
4-(4-Cyano-4-butylcylohexyl)-4'-nonoxybiphenyl, m.p. 89°, c.p. 150°
4-(4-Cyano-4-pentylcyclohexyl)-4'-ethylbiphenyl
4-(4-Cyano-4-pentylcyclohexyl)-4'-propylbiphenyl
4-(4-Cyano-4-pentylcyclohexyl)-4'-butylbiphenyl, m.p. 75°, c.p. 128°
4-(4-Cyano-4-pentylcyclohexyl)-4'-pentylbiphenyl
4-(4-Cyano-4-pentylcyclohexyl)-4'-hexylbiphenyl
4-(4-Cyano-4-pentylcyclohexyl)-4'-heptylbiphenyl, m.p. 54°, c.p. 127°
4-(4-Cyano-4-pentylcyclohexyl)-4'-octylbiphenyl, m.p. 43°, c.p. 115°
4-(4-Cyano-4-pentylcyclohexyl)-4'-nonylbiphenyl
4-(4-Cyano-4-pentylcyclohexyl)-4'-butoxybiphenyl
4-(4-Cyano-4-pentylcyclohexyl)-4'-pentoxybiphenyl
4-(4-Cyano-4-pentylcyclohexyl)-4'-hexoxybiphenyl
4-(4-Cyano-4-pentylcyclohexyl)-4'-heptoxybiphenyl, m.p. 91°, c.p. 161°
4-(4-Cyano-4-pentylcyclohexyl)-4'-octyloxybiphenyl, m.p. 93°, c.p. 160°
4-(4-Cyano-4-pentylcyclohexyl)-4'-monoxybiphenyl, m.p. 83°, c.p. 156°
4-[4-Cyano-4-(2-methylbutylcyclohexyl)]-4'-ethylbiphenyl 4-[4-Cyano-4-(2-methylbutylcyclohexyl)]-4'-propylbiphenyl
4-[4-Cyano-4-(2-methylbutylcyclohexyl)]-4'-butylbiphenyl
4-[4-Cyano-4-(2-methylbutylcyclohexyl)]-4'-pentylbiphenyl
4-[4-Cyano-4-(2-methylbutylcyclohexyl)]-4'-hexylbiphenyl
4-[4-Cyano-4-(2-methylbutylcyclohexyl)]-4'-heptylbiphenyl
4-[4-Cyano-4-(2-methylbutylcyclohexyl)]-4'-octylbiphenyl
4-[4-Cyano-4-(2-methylbutylcyclohexyl)]-4'-nonylbiphenyl
4-[4-Cyano-4-(2-methylbutylcyclohexyl)]-4'-butoxybiphenyl
4-[4-Cyano-4-(2-methylbutylcyclohexyl)]-4'-pentoxybiphenyl
4-[4-Cyano-4-(2-methylbutylcyclohexyl)]-4'-hexoxybiphenyl
4-[4-Cyano-4-(2-methylbutylcyclohexyl)]-4'-heptoxybiphenyl, m.p. 66°, c.p. 131.4°, c.p. 131.0° Ch/Bp
4-[4-Cyano-4-(2-methylbutylcyclohexyl)]-4'-octyloxybiphenyl,
4-[4-Cyano-4-(2-methylbutylcyclohexyl)]-4'-monoxybiphenyl,
4-(4-Cyano-4-hexylcyclohexyl)-4'-propylbiphenyl
4-(4-Cyano-4-hexylcyclohexyl)-4'-butylbiphenyl
4-(4-Cyano-4-hexylcyclohexyl)-4'-pentylbiphenyl
4-(4-Cyano-4-hexylcyclohexyl)-4'-hexylbiphenyl
4-(4-Cyano-4-hexylcyclohexyl)-4'-heptylbiphenyl, m.p. 66°, c.p. 125°
4-(4-Cyano-4-hexylcyclohexyl)-4'-octylbiphenyl
4-(4-Cyano-4-hexylcyclohexyl)-4'-nonylbiphenyl
4-(4-Cyano-4-hexylcyclohexyl)-4'-butoxybiphenyl
4-(4-Cyano-4-hexylcyclohexyl)-4'-pentoxybiphenyl
4-(4-Cyano-4-hexylcyclohexyl)-4'-hexoxybiphenyl
4-(4-Cyano-4-hexylcyclohexyl)-4'-heptoxybiphenyl, m.p. 88°, c.p. 156°
4-(4-Cyano-4-hexylcyclohexyl)-4'-octoxybiphenyl, m.p. 90°, c.p. 155°
4-(4-Cyano-4-hexylcyclohexyl)-4'-nonoxybiphenyl, m.p. 87°, c.p. 152°
4-(4-Cyano-4-heptylcyclohexyl)-4'-ethylbiphenyl
4-(4-Cyano-4-heptylcyclohexyl)-4'-propylbiphenyl
4-(4-Cyano-4-heptylcyclohexyl)-4'-butylbiphenyl
4-(4-Cyano-4-heptylcyclohexyl)-4'-pentylbiphenyl
4-(4-Cyano-4-heptylcyclohexyl)-4'-hexylbiphenyl
4-(4-Cyano-4-heptylcyclohexyl)-4'-heptylbiphenyl, m.p. 61°, c.p. 124°
4-(4-Cyano-4-heptylcyclohexyl)-4'-octylbiphenyl, m.p. 64°, c.p. 125°
4-(4-Cyano-4-heptylcyclohexyl)-4'-nonylbiphenyl
4-(4-Cyano-4-heptylcyclohexyl)-4'-butoxybiphenyl
4-(4-Cyano-4-heptylcyclohexyl)-4'-pentoxybiphenyl
4-(4-Cyano-4-heptylcyclohexyl)-4'-hexoxybiphenyl
4-(4-Cyano-4-heptylcyclohexyl)-4'-heptoxybiphenyl, m.p. 87°, c.p. 155°
4-(4-Cyano-4-heptylcyclohexyl)-4'-octoxybiphenyl, m.p. 83°, c.p. 154°
4-(4-Cyano-4-heptylcyclohexyl)-4'-nonoxybiphenyl, m.p. 81°, c.p. 152°
4-(4-Cyano-4-octylcyclohexyl)-4'-ethylbiphenyl
4-(4-Cyano-4-octylcyclohexyl)-4'-propylbiphenyl
4-(4-Cyano-4-octylcyclohexyl)-4'-butylbiphenyl
4-(4-Cyano-4-octylcyclohexyl)-4'-pentylbiphenyl, m.p. 52°, c.p. 124°
4-(4-Cyano-4-octylcyclohexyl)-4'-hexylbiphenyl
4-(4-Cyano-4-octylcyclohexyl)-4'-heptylbiphenyl, m.p. 61°, c.p. 122°
4-(4-Cyano-4-octylcyclohexyl)-4'-octylbiphenyl, m.p. 65°, c.p. 125°
4-(4-Cyano-4-octylcyclohexyl)-4'-nonylbiphenyl
4-(4-Cyano-4-octylcyclohexyl)-4'-butoxybiphenyl
4-(4-Cyano-4-octylcyclohexyl)-4'-pentoxybiphenyl
4-(4-Cyano-4-octylcyclohexyl)-4'-hexoxybiphenyl
4-(4-Cyano-4-octylcyclohexyl)-4'-heptoxybiphenyl, m.p. 85°, c.p. 151°
4-(4-Cyano-4-octylcyclohexyl)-4'-octoxybiphenyl, m.p. 81°, c.p. 150°
4-(4-Cyano-4-octylcyclohexyl)-4'-nonoxybiphenyl, m.p. 72°, c.p. 149°
4-(4-Cyano-4-nonylcyclohexyl)-4'-ethylbiphenyl
4-(4-Cyano-4-octylcyclohexyl)-4'-propylbiphenyl
4-(4-Cyano-4-octylcyclohexyl)-4'-butylbiphenyl
4-(4-Cyano-4-octylcyclohexyl)-4'-pentylbiphenyl
4-(4-Cyano-4-octylcyclohexyl)-4'-heptylbiphenyl
4-(4-Cyano-4-octylcyclohexyl)-4'-octylbiphenyl
4-(4-Cyano-4-octylcyclohexyl)-4'-nonylbiphenyl
4-(4-Cyano-4-octylcyclohexyl)-4'-butoxybiphenyl
4-(4-Cyano-4-octylcyclohexyl)-4'-pentoxybiphenyl
4-(4-Cyano-4-octylcyclohexyl)-4'-hexoxybiphenyl
4-(4-Cyano-4-octylcyclohexyl)-4'-heptoxybiphenyl
4-(4-Cyano-4-octylcyclohexyl)-4'-octoxybiphenyl
4-(4-Cyano-4-octylcyclohexyl)-4'-nonoxybiphenyl All compounds of the formula V are prepared by methods known per se, as described in the literature (for example in standard works such as Houben-Weyl, Methoden der Organischen Chemie, (Methods of Organic Chemistry), Georg-Thieme-Verlag, Stuttgart), under reaction conditions which are known and suitable for the reactions mentioned. In this context, use can also be made of variants which are known per se and are not referred to here in further detail.

For the most part, formula V comprises known compounds, for example the preferred compounds described in German Offenlegungsschrift 3,231,707, 3,319,781, 3,320,024, 3,407,013, 3,443,029, 3,332,690, 3,332,691, 3,332,692, 2,933,563, 2,853,728, 2,613,293, 3,401,320, 3,134,624, 3,040,632, 3,205,766, 2,240,864, 2,937,700, 3,410,734, 3,324,686, EP-OS 0,085,995, EP-OS 0,084,194, East German Patent 116,732, French Patent Specifications 2,425,469 and 2,419,966, U.S. Pat. Nos. 4,237,026, 3,953,491 and 4,225,454 and in H. J. Deutscher et al., J. prakt. Chemie, 321,569 (1979) and J. C. Dubois et al. Mol Cryst. Liq. Cryst. 47, 193 (1978).

Further components of the phases according to the invention may be compounds of the formula

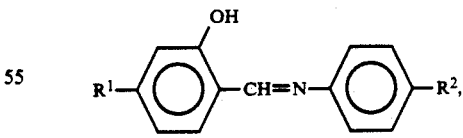

in which $R^1$ and $R^2$ have the meaning given in Formula V.

Chirally tilted smectic liquid crystalline phases according to the invention, the achiral base mixture of which contains, in addition to compounds of the formula I, at least one other component with negative or small positive dielectric anisotropy, are especially preferred. Other suitable components with small positive or negative dielectric anisotropy, are compounds of the partial formulae Va to Vp:

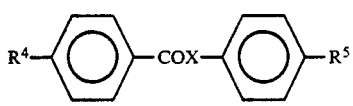 Va

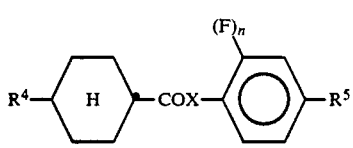 Vb

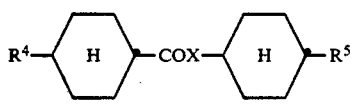 Vc

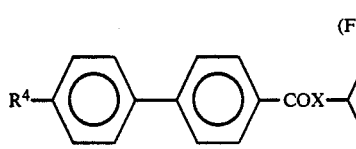 Vd

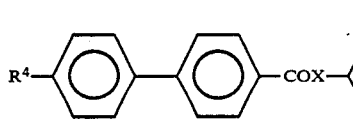 Ve

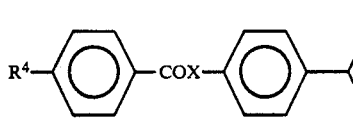 Vf

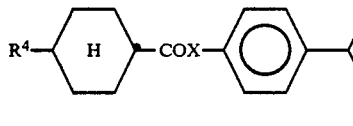 Vg

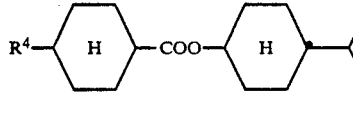 Vh

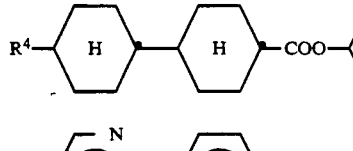 Vi

 Vj

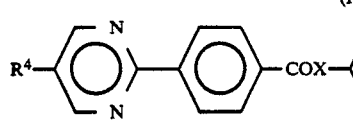 Vk

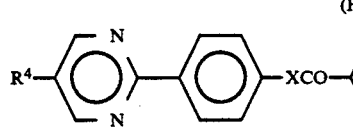 Vl

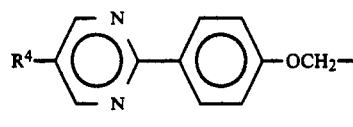 Vm

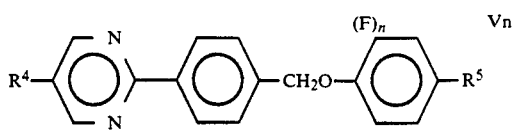 Vn

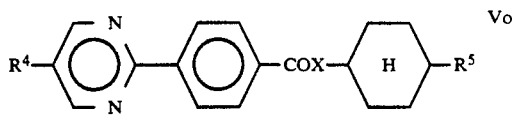 Vo

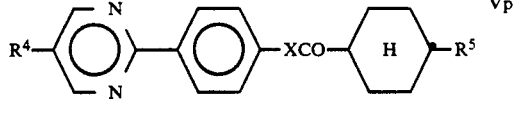 Vp $R^4$ and $R^5$ each are preferably straight-chain alkyl, alkoxy, alkanoyloxy or alkoxycarbonyl of, in each case, 3 to 12 carbon atoms. X is preferably O. n is 0 or 1.

The compounds of the partial formulae Va, Vb, Vd and Vf, in which $R^4$ and $R^5$ each are straight-chain alkyl or alkoxy of, in each case, 5 to 10 carbon atoms, are particularly preferred.

The compounds of the partial formulae Vc, Vh and Vi are suitable as melting point-depressing additives and they are normally added to the basic mixtures in amounts not greater than 5%, preferably 1 to 3%. $R^4$ and $R^5$ in the compounds of the partial formulae Vc, Vh and Vi are, preferably, straight-chain alkyl or 2 to 7, preferably 3 to 5, carbon atoms. Another class of compounds suitable as melting point depressants in the phases according to the invention, is that of the formula

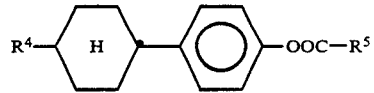

in which $R^4$ and $R^5$ have the preferred meaning indicated for Vc, Vh and Vi.

Other suitable components with a negative dielectric anisotropy are compounds comprising the structural element B or C.

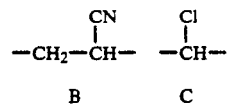

Preferred compounds of this type correspond to the formulae VIb and VIc:

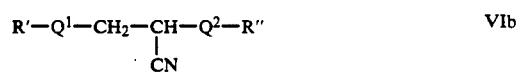 VIb

 VIc

R' and R" each are preferably straight-chain alkyl or alkoxy groups of, in each case, 2 to 10 carbon atoms. $Q^1$ and $Q^2$ each are 1,4-phenylene, trans-1,4-cyclohexylene 4,4'-biphenylyl, 4-(trans-4-cyclohexyl)phenyl, trans, trans-4,4'-bicyclohexyl, or one of the groups $Q^1$ and $Q^2$ is also a single bond.

$Q^3$ and $Q^4$ each are 1,4-phenylene, 4,4'-biphenylyl or trans-1,4-cyclohexylene. One of the groups $Q^3$ and $Q^4$ can also be 1,4-phenylene, in which at least one CH group is replaced by N. R''' is an optically active radical with an asymmetric carbon atom of the structure

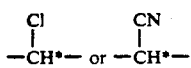

Particularly preferred compounds of the formula VIc are those of the formula VIc':

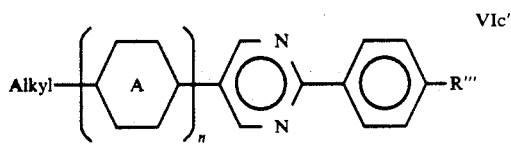

in which A is 1,4-phenylene or trans-1,4-cyclohexylene, and n is 0 or 1.

The phases according to the invention contain about 0.5–40%, preferably 5–10%, of one or more compounds of the formula I.

Phases according to the invention, containing 0.3–5%, preferably 1–4%, of one or more compounds of the formula I, are furthermore preferred.

The preparation of the dielectrics according to the invention is carried out in the usual manner. The components are usually dissolved in one another, conveniently at elevated temperature.

The liquid crystalline phases according to the invention can be modified by suitable additions in such a manner that they can be utilized in all types of liquid crystal display elements known so far.

The examples below are intended to illustrate the invention without limiting it. M.p.=melting point, c.p.=clear point. All percentages, whether those above or those below, are percentages by weight; all temperatures are given in degrees Celsius. The values for the spontaneous polarization are valid at room temperature. Other meaning are: K: crystalline-solid state, S: smectic phase (the suffix indicates the type of phase), N: nematic state, Ch: cholesteric phase, I: isotropic phase. The number situated between two symbols indicates the transition temperatures in degrees Celsius. "Usual working up" means the following: the mixture is treated with water and extracted with methylene chloride, the phases are separated, the organic phase is dried, evaporated and the product is purified by crystallization and/or chromatography.

EXAMPLE 1

A solution of 15.2 g of 4-(5-n-nonylpyrimid-2-yl)-phenol, 5.5 g of R-2-chloropropionic acid and 0.62 g of 4-N,N-dimethylaminopyridine in 100 ml of dichloromethane is slowly treated at 0° with a solution of 11.6 g of dicyclohexylcarbodiimide in 6 ml of dichloromethane; the mixture is warmed to room temperature and stirred for a further 2 hours. After filtering off the separated urea derivative, the filtrate is washed with dilute hydrochloric acid and water, and the organic phase is worked up in the usual way. R-4-(5-n-nonyl-pyrimid-2-yl)-phenyl 2-chloropropionate, m.p. 69°, is obtained.

The optically active compounds listed below are prepared in an analogous manner by esterification or etherification in accordance with a method known from the literature:

2-p-(2-Methylbutoxyphenyl)-5-butylpyrimidine
2-p-(2-Methylbutoxyphenyl)-5-pentylpyrimidine
2-p-(2-Methylbutoxyphenyl)-5-hexylpyrimidine
2-p-(2-Methylbutoxyphenyl)-5-heptylpyrimidine
2-p-(2-Methylbutoxyphenyl)-5-octylpyrimidine
2-p-(2-Methylbutoxyphenyl)-5-nonylpyrimidine
2-p-(2-Methylbutoxyphenyl)-5-decylpyrimidine
2-p-(2-Methylbutoxyphenyl)-5-undecylpyrimidine, m.p. 40°, c.p. 47°, $S_C^*/S_A^*$ 41°
2-p-(2-Methylbutoxyphenyl)-5-dodecylpyrimidine
2-p-(2-Methylbutoxyphenyl)-5-heptoxymethylpyrimidine
2-p-(2-Methylbutoxyphenyl)-5-hexoxyethylpyrimidine
2-p-(2-Methylbutoxyphenyl)-5-pentoxypropylpyrimidine
2-p-(3-Methylpentoxyphenyl)-5-butylpyrimidine
2-p-(3-Methylpentoxyphenyl)-5-pentylpyrimidine
2-p-(3-Methylpentoxyphenyl)-5-hexylpyrimidine, m.p. 13°, c.p. 32°
2-p-(3-Methylpentoxyphenyl)-5-heptylpyrimidine, m.p. 39°
2-p-(3-Methylpentoxyphenyl)-5-octylpyrimidine, m.p. 36°
2-p-(3-Methylpentoxyphenyl)-5-nonylpyrimidine, m.p. 23°, c.p. 46°, $S_C^*/S_A^*$ 39°
2-p-(3-Methylpentoxyphenyl)-5-decylpyrimidine, m.p. 22°, c.p. 41°
2-p-(3-Methylpentoxyphenyl)-5-undecylpyrimidine, m.p. 25°, c.p. 50°, $S_C^*/S_A^*$ 45°
2-p-(3-Methylpentoxyphenyl)-5-dodecylpyrimidine, m.p. 28°, c.p. 51°, $S_C^*/S_A^*$ 47°
2-p-(3-Methylpentoxyphenyl)-5-heptoxymethylpyrimidine
2-p-(3-Methylpentoxyphenyl)-5-hexoxyethylpyrimidine
2-p-(3-Methylpentoxyphenyl)-5-pentoxypropylpyrimidine
2-p-(4-Methylhexoxyphenyl)-5-butylpyrimidine
2-p-(4-Methylhexoxyphenyl)-5-pentylpyrimidine
2-p-(4-Methylhexoxyphenyl)-5-hexylpyrimidine, m.p. 25°, c.p. 42°
2-p-(4-Methylhexoxyphenyl)-5-heptylpyrimidine, m.p. 28.5°, c.p. 60°, $S_C^*/S_A^*$ 54°
2-p-(4-Methylhexoxyphenyl)-5octylpyrimidine, m.p. 31°, c.p. 51°, $S_C^*/S_A^*$ 47°
2-p-(4-Methylhexoxyphenyl)-5-nonylpyrimidine, m.p. 23°, c.p. 52°, $S_C^*/S_A^*$ 30°
2-p-(4-Methylhexoxyphenyl)-5-decylpyrimidine, m.p. 33°, c.p. 58°
2-p-(4-Methylhexoxyphenyl)-5-undecylpyrimidine, m.p. 36°, c.p. 60°
2-p-(4-Methylhexoxyphenyl)-5-dodecylpyrimidine, m.p. 41°, c.p. 52°
2-p-(4-Methylhexoxyphenyl)-5-heptoxymethylpyrimidine
2-p-(4-Methylhexoxyphenyl)-5-hexoxyethylpyrimidine
2-p-(4-Methylhexoxyphenyl)-5-pentoxypropylpyrimidine
2-p-(5-Methylheptoxyphenyl)-5-butylpyrimidine
2-p-(5-Methylheptoxyphenyl)-5-pentylpyrimidine
2-p-(5-Methylheptoxyphenyl)-5-hexylpyrimidine, m.p. −5° c.p. 42°
2-p-(5-Methylheptoxyphenyl)-5-heptylpyrimidine, m.p. −6°, c.p. 49°
2-p-(5-Methylheptoxyphenyl)-5-octylpyrimidine, m.p. 12°, c.p. 50°, $S_C^*/S_A^*$ 35°
2-p-(5-Methylheptoxyphenyl)-5-nonylpyrimidine, m.p. 10°, c.p. 59°, $S_C^*/S_A^*$ 46°

2-p-(5-Methylheptoxyphenyl)-5-decylpyrimidine, m.p. 17°, c.p. 63°, S$_C$*/S$_A$* 54°
2-p-(5-Methylheptoxyphenyl)-5-undecylpyrimidine, m.p. 20°, c.p. 59°
2-p-(5-Methylheptoxyphenyl)-5-dodecylpyrimidine, m.p. 23°, c.p. 61°
2-p-(5-Methylheptoxyphenyl)-5-heptoxymethylpyrimidine
2-p-(5-Methylheptoxyphenyl)-5-hexoxyethylpyrimidine
2-p-(5-Methylheptoxyphenyl)-5-pentoxypropylpyrimidine
2-p-(6-Methyloctoxyphenyl)-5-butylpyrimidine
2-p-(6-Methyloctoxyphenyl)-5-pentylpyrimidine
2-p-(6-Methyloctoxyphenyl)-5-hexylpyrimidine, m.p. 12°, c.p. 46°
2-p-(6-Methyloctoxyphenyl)-5-heptylpyrimidine, m.p. 10°, c.p. 61, S$_C$*/S$_A$* 39°
2-p-(6-Methyloctoxyphenyl)-5-octylpyrimidine, m.p. 3°, c.p. 56°, S$_C$*/S$_A$* 49°
2-p-(6-Methyloctoxyphenyl)-5-nonylpyrimidine, m.p. 16°, c.p. 61°, S$_C$*/S$_A$* 49°
2-p-(6-Methyloctoxyphenyl)-5-decylpyrimidine, m.p. 41°, c.p. 61°
2-p-(6-Methyloctoxyphenyl)-5-undecylpyrimidine
2-p-(6-Methyloctoxyphenyl)-5-dodecylpyrimidine, m.p. 40°, c.p. 70°
2-p-(6-Methyloctoxyphenyl)-5-heptoxymethylpyrimidine
2-p-(6-Methyloctoxyphenyl)-5-hexoxyethylpyrimidine
2-p-(6-Methyloctoxyphenyl)-5-pentoxypropylpyrimidine
2-p-(2-Methylbutyryloxyphenyl)-5-butylpyrimidine
2-p-(2-Methylbutyryloxyphenyl)-5-pentylpyrimidine
2-p-(2-Methylbutyryloxyphenyl)-5-hexylpyrimidine
2-p-(2-Methylbutyryloxyphenyl)-5-heptylpyrimidine
2-p-(2-Methylbutyryloxyphenyl)-5-octylpyrimidine
2-p-(2-Methylbutyryloxyphenyl)-5-nonylpyrimidine
2-p-(2-Methylbutyryloxyphenyl)-5-decylpyrimidine
2-p-(2-Methylbutyryloxyphenyl)-5-undecylpyrimidine, m.p. 52°
2-p-(2-Methylbutyryloxyphenyl)-5-dodecylpyrimidine
2-p-(2-Methylbutyryloxyphenyl)-5-heptoxymethylpyrimidine
2-p-(2-Methylbutyryloxyphenyl)-5-hexoxyethylpyrimidine
2-p-(2-Methylbutyryloxyphenyl)-5-pentoxypropylpyrimidine
2-p-(4-Methylhexanoyloxyphenyl)-5-butylpyrimidine
2-p-(4-Methylhexanoyloxyphenyl)-5-pentylpyrimidine
2-p-(4-Methylhexanoyloxyphenyl)-5-hexylpyrimidine
2-p-(4-Methylhexanoyloxyphenyl)-5-heptylpyrimidine
2-p-(4-Methylhexanoyloxyphenyl)-5-octylpyrimidine, m.p. 54°
2-p-(4-Methylhexanoyloxyphenyl)-5-nonylpyrimidine
2-p-(4-Methylhexanoyloxyphenyl)-5-decylpyrimidine
2-p-(4-Methylhexanoyloxyphenyl)-5-undecylpyrimidine, m.p. 38°, c.p. 50°
2-p-(4-Methylhexanoyloxyphenyl)-5-dodecylpyrimidine
2-p-(4-Methylhexanoyloxyphenyl)-5-heptoxymethylpyrimidine
2-p-(4-Methylhexanoyloxyphenyl)-5-hexoxyethylpyrimidine
2-p-(4-Methylhexanoyloxyphenyl)-5-pentoxypropylpyrimidine
2-p-(6-Methyloctanoyloxyphenyl)-5-butylpyrimidine
2-p-(6-Methyloctanoyloxyphenyl)-5-pentylpyrimidine
2-p-(6-Methyloctanoyloxyphenyl)-5-hexylpyrimidine
2-p-(6-Methyloctanoyloxyphenyl)-5-heptylpyrimidine
2-p-(6-Methyloctanoyloxyphenyl)-5-octylpyrimidine, m.p. 38°, c.p. 45°
2-p-(6-Methyloctanoyloxyphenyl)-5-nonylpyrimidine
2-p-(6-Methyloctanoyloxyphenyl)-5-decylpyrimidine
2-p-(6-Methyloctanoyloxyphenyl)-5-undecylpyrimidine, m.p. 62°
2-p-(6-Methyloctanoyloxyphenyl)-5-dodecylpyrimidine
2-p-(6-Methyloctanoyloxyphenyl)-5-heptoxymethylpyrimidine
2-p-(6-Methyloctanoyloxyphenyl)-5-hexoxyethylpyrimidine
2-p-(6-Methyloctanoyloxyphenyl)-5-pentoxypropylpyrimidine
2-p-(6-Methyloctanoylphenyl)-5-butylpyrimidine
2-p-(6-Methyloctanoylphenyl)-5-pentylpyrimidine
2-p-(6-Methyloctanoylphenyl)-5-hexylpyrimidine
2-p-(6-Methyloctanoylphenyl)-5-heptylpyrimidine
2-p-(6-Methyloctanoylphenyl)-5-octylpyrimidine, m.p. 67°, c.p. 79°
2-p-(6-Methyloctanoylphenyl)-5-nonylpyrimidine
2-p-(6-Methyloctanoylphenyl)-5-decylpyrimidine
2-p-(6-Methyloctanoylphenyl)-5-undecylpyrimidine
2-p-(6-Methyloctanoylphenyl)-5-dodecylpyrimidine
2-p-(6-Methyloctanoylphenyl)-5-heptoxymethylpyrimidine
2-p-(6-Methyloctanoylphenyl)-5-hexoxyethylpyrimidine
2-p-(6-Methyloctanoylphenyl)-5-pentoxypropylpyrimidine
2-p-(3-Chloropentoxyphenyl)-5-butylpyrimidine
2-p-(3-Chloropentoxyphenyl)-5-pentylpyrimidine
2-p-(3-Chloropentoxyphenyl)-5-hexylpyrimidine
2-p-(3-Chloropentoxyphenyl)-5-heptylpyrimidine
2-p-(3-Chloropentoxyphenyl)-5-octylpyrimidine, m.p. 15°, c.p. 43°
2-p-(3-Chloropentoxyphenyl)-5-nonylpyrimidine
2-p-(3-Chloropentoxyphenyl)-5-decylpyrimidine
2-p-(3-Chloropentoxyphenyl)-5-undecylpyrimidine
2-p-(3-Chloropentoxyphenyl)-5-dodecylpyrimidine
2-p-(3-Chloropentoxyphenyl)-5-heptoxymethylpyrimidine
2-p-(3-Chloropentoxyphenyl)-5-hexoxyethylpyrimidine
2-p-(3-Chloropentoxyphenyl)-5-pentoxypropylpyrimidine
2-p-(3-Cyanopentoxyphenyl)-5-butylpyrimidine
2-p-(3-Cyanopentoxyphenyl)-5-pentylpyrimidine
2-p-(3-Cyanopentoxyphenyl)-5-hexylpyrimidine
2-p-(3-Cyanopentoxyphenyl)-5-heptylpyrimidine
2-p-(3-Cyanopentoxyphenyl)-5-octylpyrimidine
2-p-(3-Cyanopentoxyphenyl)-5-nonylpyrimidine
2-p-(3-Cyanopentoxyphenyl)-5-decylpyrimidine
2-p-(3-Cyanopentoxyphenyl)-5-undecylpyrimidine, m.p. 60°
2-p-(3-Cyanopentoxyphenyl)-5-dodecylpyrimidine
2-p-(3-Cyanopentoxyphenyl)-5-heptoxymethylpyrimidine
2-p-(3-Cyanopentoxyphenyl)-5-hexoxyethylpyrimidine
2-p-(3-Cyanopentoxyphenyl)-5-pentoxypropylpyrimidine
2-p-(1,6-Dioxa-8-methyldecylphenyl)-5-butylpyrimidine
2-p-(1,6-Dioxa-8-methyldecylphenyl)-5-pentylpyrimidine
2-p-(1,6-Dioxa-8-methyldecylphenyl)-5-hexylpyrimidine, m.p. −8°, c.p. −28°

2-p-(1,6-Dioxa-8-methyldecylphenyl)-5-heptylpyrimidine
2-p-(1,6-Dioxa-8-methyldecylphenyl)-5-octylpyrimidine, m.p. 1°, c.p. 42°
2-p-(1,6-Dioxa-8-methyldecylphenyl)-5-nonylpyrimidine
2-p-(1,6-Dioxa-8-methyldecylphenyl)-5-decylpyrimidine m.p. 16°, c.p. 52°
2-p-(1,6-Dioxa-8-methyldecylphenyl)-5-undecylpyrimidine
2-p-(1,6-Dioxa-8-methyldecylphenyl)-5-dodecylpyrimidine
2-p-(1,6-Dioxa-8-methyldecylphenyl)-5-heptoxymethylpyrimidine
2-p-(1,6-Dioxa-8-methyldecylphenyl)-5-hexoxyethylpyrimidine
2-p-(1,6-Dioxa-8-methyldecylphenyl)-5-pentoxypropylpyrimidine
2-p-Octyloxyphenyl-5-(2-methyloctyl)-pyrimidine
2-p-Octyloxyphenyl-5-(3-methyloctyl)-pyrimidine
2-p-Octyloxyphenyl-5-(4-methyloctyl)-pyrimidine
2-p-Octyloxyphenyl-5-(5-methyloctyl)-pyrimidine
2-p-Octyloxyphenyl-5-(6-methyloctyl)-pyrimidine, m.p. 14°c.p. 44°
2-p-Octyloxyphenyl-5-(2-methyloctyloxy)-pyrimidine
2-p-Octyloxyphenyl-5-(3-methyloctyloxy)-pyrimidine
2-p-Octyloxyphenyl-5-(4-methyloctyloxy)-pyrimidine
2-p-Octyloxyphenyl-5-(5-methyloctyloxy)-pyrimidine
2-p-Octyloxyphenyl-5-(6-methyloctyloxy)-pyrimidine m.p. 13°, c.p. 51°
2-p-(2-Methylbutoxy)-phenyl-5-butyloxypyrimidine
2-p-(2-Methylbutoxy)-phenyl-5-pentyloxypyrimidine
2-p-(2-Methylbutoxy)-phenyl-5-hexyloxypyrimidine
2-p-(2-Methylbutoxy)-phenyl-5-heptyloxypyrimidine
2-p-(2-Methylbutoxy)-phenyl-5-octyloxypyrimidine
2-p-(2-Methylbutoxy)-phenyl-5-nonyloxypyrimidine
2-p-(2-Methylbutoxy)-phenyl-5-decyloxypyrimidine
2-p-(2-Methylbutoxy)-phenyl-5-undecyloxypyrimidine, m.p. 58° c.p. 77°
2-p-(2-Methylbutoxy)-phenyl-5-dodecyloxypyrimidine
2-p-(2-Methylbutoxy)-phenyl-5-heptoxymethyloxypyrimidine
2-p-(2-Methylbutoxy)-phenyl-5-hexoxyethyloxypyrimidine
2-p-(2-Methylbutoxy)-phenyl-5-pentoxypropyloxypyrimidine
2-p-(3-Methylpentoxy)-phenyl-5-butyloxypyrimidine
2-p-(3-Methylpentoxy)-phenyl-5-pentyloxypyrimidine
2-p-(3-Methylpentoxy)-phenyl-5-hexyloxypyrimidine
2-p-(3-Methylpentoxy)-phenyl-5-heptyloxypyrimidine
2-p-(3-Methylpentoxy)-phenyl-5-octyloxypyrimidine, m.p. 52°, c.p. 76°
2-p-(3-Methylpentoxy)-phenyl-5-nonyloxypyrimidine
2-p-(3-Methylpentoxy)-phenyl-5-decyloxypyrimidine
2-p-(3-Methylpentoxy)-phenyl-5-undecyloxypyrimidine, m.p. 48° c.p. 78°
2-p-(3-Methylpentoxy)-phenyl-5-dodecyloxypyrimidine
2-p-(3-Methylpentoxy)-phenyl-5-heptoxymethyloxypyrimidine
2-p-(3-Methylpentoxy)-phenyl-5-hexoxyethyloxypyrimidine
2-p-(3-Methylpentoxy)-phenyl-5-pentoxypropyloxypyrimidine
2-p-(6-Methyloctoxy)-phenyl-5-butyloxypyrimidine
2-p-(6-Methyloctoxy)-phenyl-5-pentyloxypyrimidine
2-p-(6-Methyloctoxy)-phenyl-5-hexyloxypyrimidine
2-p-(6-Methyloctoxy)-phenyl-5-heptyloxypyrimidine
2-p-(6-Methyloctoxy)-phenyl-5-octyloxypyrimidine
2-p-(6-Methyloctoxy)-phenyl-5-nonyloxypyrimidine
2-p-(6-Methyloctoxy)-phenyl-5-decyloxypyrimidine
2-p-(6-Methyloctoxy)-phenyl-5-undecyloxypyrimidine, m.p. 41°c.p. 89°
2-p-(6-Methyloctoxy)-phenyl-5-dodecyloxypyrimidine
2-p-(6-Methyloctoxy)-phenyl-5-heptoxymethyloxypyrimidine
2-p-(6-Methyloctoxy)-phenyl-5-hexoxyethyloxypyrimidine
2-p-(6-Methyloctoxy)-phenyl-5-pentoxypropyloxypyrimidine
2-p-(2-Methyloctoxy)-phenyl-5-butyloxypyrimidine
2-p-(2-Methyloctoxy)-phenyl-5-pentyloxypyrimidine
2-p-(2-Methyloctoxy)-phenyl-5-hexyloxypyrimidine
2-p-(2-Methyloctoxy)-phenyl-5-heptyloxypyrimidine
2-p-(2-Methyloctoxy)-phenyl-5-octyloxypyrimidine, m.p. 36°, c.p. 62°, $S_C^*/S_A^*$ 41°
2-p-(2-Methyloctoxy)-phenyl-5-nonyloxypyrimidine
2-p-(2-Methyloctoxy)-phenyl-5-decyloxypyrimidine
2-p-(2-Methyloctoxy)-phenyl-5-undecyloxypyrimidine
2-p-(2-Methyloctoxy)-phenyl-5-dodecyloxypyrimidine
2-p-(2-Methyloctoxy)-phenyl-5-heptoxymethyloxypyrimidine
2-p-(2-Methyloctoxy)-phenyl-5-hexoxyethyloxypyrimidine
2-p-(2-Methyloctoxy)-phenyl-5-pentoxypropyloxypyrimidine
2-p-(2-Methylbutyryloxy)-phenyl-5-butyloxypyrimidine
2-p-(2-Methylbutyryloxy)-phenyl-5-pentyloxypyrimidine
2-p-(2-Methylbutyryloxy)-phenyl-5-hexyloxypyrimidine
2-p-(2-Methylbutyryloxy)-phenyl-5-heptyloxypyrimidine
2-p-(2-Methylbutyryloxy)-phenyl-5-octyloxypyrimidine, m.p. 66°
2-p-(2-Methylbutyryloxy)-phenyl-5-nonyloxypyrimidine
2-p-(2-Methylbutyryloxy)-phenyl-5-decyloxypyrimidine
2-p-(2-Methylbutyryloxy)-phenyl-5-undecyloxypyrimidine, m.p. 43°, c.p. 67°, $S_C^*/S_A^*$ 64°
2-p-(2-Methylbutyryloxy)-phenyl-5-dodecyloxypyrimidine
2-p-(2-Methylbutyryloxy)-phenyl-5-heptoxymethyloxypyrimidine
2-p-(2-Methylbutyryloxy)-phenyl-5-hexoxyethyloxypyrimidine
2-p-(2-Methylbutyryloxy)-phenyl-5-pentoxypropyloxypyrimidine
2-p-(3-Methylpentanoyloxy)-phenyl-5-butyloxypyrimidine
2-p-(3-Methylpentanoyloxy)-phenyl-5-pentyloxypyrimidine
2-p-(3-Methylpentanoyloxy)-phenyl-5-hexyloxypyrimidine
2-p-(3-Methylpentanoyloxy)-phenyl-5-heptyloxypyrimidine
2-p-(3-Methylpentanoyloxy)-phenyl-5-octyloxypyrimidine, m.p. 70°, c.p. 73°
2-p-(3-Methylpentanoyloxy)-phenyl-5-nonyloxypyrimidine
2-p-(3-Methylpentanoyloxy)-phenyl-5-decyloxypyrimidine
2-p-(3-Methylpentanoyloxy)-phenyl-5-undecyloxypyrimidine, m.p. 55°, c.p. 78°

2-p-(3-Methylpentanoyloxy)-phenyl-5-dodecyloxypyrimidine
2-p-(3-Methylpentanoyloxy)-phenyl-5-heptoxymethyloxypyrimidine
2-p-(3-Methylpentanoyloxy)-phenyl-5-hexoxyethyloxypyrimidine
2-p-(3-Methylpentanoyloxy)-phenyl-5-pentoxypropyloxypyrimidine
2-p-(4-Methylhexanoyloxy)-phenyl-5-butyloxypyrimidine
2-p-(4-Methylhexanoyloxy)-phenyl-5-pentyloxypyrimidine
2-p-(4-Methylhexanoyloxy)-phenyl-5-hexyloxypyrimidine
2-p-(4-Methylhexanoyloxy)-phenyl-5-heptyloxypyrimidine
2-p-(4-Methylhexanoyloxy)-phenyl-5-octyloxypyrimidine, m.p. 78°
2-p-(4-Methylhexanoyloxy)-phenyl-5-nonyloxypyrimidine
2-p-(4-Methylhexanoyloxy)-phenyl-5-decyloxypyrimidine
2-p-(4-Methylhexanoyloxy)-phenyl-5-undecyloxypyrimidine
2-p-(4-Methylhexanoyloxy)-phenyl-5-dodecyloxypyrimidine
2-p-(4-Methylhexanoyloxy)-phenyl-5-heptoxymethyloxypyrimidine
2-p-(4-Methylhexanoyloxy)-phenyl-5-hexoxyethyloxypyrimidine
2-p-(4-Methylhexanoyloxy)-phenyl-5-pentoxypropyloxypyrimidine
2-p-(6-Methyloctanoyloxy)-phenyl-5-butyloxypyrimidine
2-p-(6-Methyloctanoyloxy)-phenyl-5-pentyloxypyrimidine
2-p-(6-Methyloctanoyloxy)-phenyl-5-hexyloxypyrimidine
2-p-(6-Methyloctanoyloxy)-phenyl-5-heptyloxypyrimidine,
2-p-(6-Methyloctanoyloxy)-phenyl-5-octyloxypyrimidine, m.p. 76°, c.p. 80°
2-p-(6-Methyloctanoyloxy)-phenyl-5-nonyloxypyrimidine
2-p-(6-Methyloctanoyloxy)-phenyl-5-decyloxypyrimidine
2-p-(6-Methyloctanoyloxy)-phenyl-5-undecyloxypyrimidine
2-p-(6-Methyloctanoyloxy)-phenyl-5-dodecyloxypyrimidine
2-p-(6-Methyloctanoyloxy)-phenyl-5-heptoxymethyloxypyrimidine
2-p-(6-Methyloctanoyloxy)-phenyl-5-hexoxyethyloxypyrimidine
2-p-(6-Methyloctanoyloxy)-phenyl-5-pentoxypropyloxypyrimidine
2-p-(6-Methyloctyloxy)-phenyl-5-butyloxycarbonylpyrimidine
2-p-(6-Methyloctyloxy)-phenyl-5-pentyloxycarbonylpyrimidine
2-p-(6-Methyloctyloxy)-phenyl-5-hexyloxycarbonylpyrimidine
2-p-(6-Methyloctyloxy)-phenyl-5-heptyloxycarbonylpyrimidine
2-p-(6-Methyloctyloxy)-phenyl-5-octyloxycarbonylpyrimidine, m.p. 78°, c.p. 80°
2-p-(6-Methyloctyloxy)-phenyl-5-nonyloxycarbonylpyrimidine
2-p-(6-Methyloctyloxy)-phenyl-5-decyloxycarbonylpyrimidine
2-p-(6-Methyloctyloxy)-phenyl-5-undecyloxycarbonylpyrimidine
2-p-(6-Methyloctyloxy)-phenyl-5-dodecyloxycarbonylpyrimidine
2-p-(6-Methyloctyloxy)-phenyl-5-heptoxymethyloxycarbonylpyrimidine
2-p-(6-Methyloctyloxy)-phenyl-5-hexoxyethyloxycarbonylpyrimidine
2-p-(6-Methyloctyloxy)-phenyl-5-pentoxypropyloxycarbonylpyrimidine
2-p-Octyloxyphenyl-5-(2-methyloctyloxycarbonyl)-pyrimidine
2-p-Octyloxyphenyl-5-(3-methyloctyloxycarbonyl)-pyrimidine
2-p-Octyloxyphenyl-5-(4-methyloctyloxycarbonyl)-pyrimidine
2-p-Octyloxyphenyl-5-(5-methyloctyloxycarbonyl)-pyrimidine
2-p-Octyloxyphenyl-5-(6-methyloctyloxycarbonyl)-pyrimidine, m.p. 80°
2-p-Dodecyloxyphenyl-5-(2-methyloctyloxycarbonyl)-pyrimidine
2-p-Undecyloxyphenyl-5-(2-methylbutoxy)-pyrimidine, m.p. 51°
2-p-Decyloxyphenyl-5-(2-methylbutoxy)-pyrimidine
2-p-Nonyloxyphenyl-5-(2-methylbutoxy)-pyrimidine
2-p-Octyloxyphenyl-5-(2-methylbutoxy)-pyrimidine
2-p-Heptyloxyphenyl-5-(2-methylbutoxy)-pyrimidine
2-p-Dodecanoyloxyphenyl-5-(2-methylbutoxy)-pyrimidine
2-p-Undecanoyloxyphenyl-5-(2-methylbutoxy)-pyrimidine, m.p. 58°
2-p-Decanoyloxyphenyl-5-(2-methylbutoxy)-pyrimidine
2-p-Nonanoyloxyphenyl-5-(2-methylbutoxy)-pyrimidine
2-p-Octanoyloxyphenyl-5-(2-methylbutoxy)-pyrimidine
2-p-Heptanoyloxyphenyl-5-(2-methylbutoxy)-pyrimidine
R-4-(5-Dodecylpyrimid-2-yl)-phenyl 2-chloropropionate
R-4-(5-Undecylpyrimid-2-yl)-phenyl 2-chloropropionate
R-4-(5-Decylpyrimid-2-yl)-phenyl-2 chloropropionate
R-4-(5-Octylpyrimid-2-yl)-phenyl-2 chloropropionate
R-4-(5-Heptylpyrimid-2-yl)-phenyl 2-chloropropionate, m.p. 93°
R-4-(5-Hexylpyrimid-2-yl)-phenyl 2-chloropropionate, m.p. 82°
R-4-(5-Pentylpyrimid-2-yl)-phenyl 2-chloropropionate
R-4-(5-Butylpyrimid-2-yl)-phenyl 2-chloropropionate
R-4-(5-Propylpyrimid-2-yl)-phenyl 2-chloropropionate.

Esterification of 5-(p-alkylphenyl)-pyrazin-2-ol (obtainable by $SeO_2$ oxidation of p-alkylacetophenone, followed by reaction with glycinamide hydrochloride by methods known from the literature) gives rise in an analogous manner to:
R-5-(p-Propylphenyl)-pyrazin-2-yl-2-chloropropionate
R-5-(p-Butylphenyl)-pyrazin-2-yl-2-chloropropionate
R-5-(p-Pentylphenyl)-pyrazin-2-yl-2-chloropropionate
R-5-(p-Hexylphenyl)-pyrazin-2-yl-2-chloropropionate
R-5-(p-Heptylphenyl)-pyrazin-2-yl-2-chloropropionate
R-5-(p-Octylphenyl)-pyrazin-2-yl-2-chloropropionate
R-5-(p-Nonylphenyl)-pyrazin-2-yl-2-chloropropionate
R-5-(p-Decylphenyl)-pyrazin-2-yl-2-chloropropionate R-5-(p-Undecylphenyl)-pyrazin-2-yl-2-chloropropionate R-5-(p-Dodecylphenyl)-pyrazin-2-yl-2-chloropropionate The optically active alcohols or carboxylic acids used are either known or they can be obtained, by analogy with known compounds, by methods known from the literature, for example by homologizing.

EXAMPLE 2

A suspension of 7.5 g of 4-(5-n-heptylpyrimidin-2-yl)benzoic acid [obtainable by an alkaline saponification of 2-(4-cyanophenyl)-5-n-heptylpyrimidine] in 80 of dichloromethane is treated with 3.3 g of d-2-octanol and 0.3 g of 4-N,N-(dimethylamino)-pyridine; 5.8 g of dicyclohexylcarbodiimide is added with stirring at 5°–10°, stirring is continued for 30 minutes at 10° and subsequently overnight at room temperature, the mixture is filtered off from the precipitated urea and is worked up in the usual manner. 5-n-Heptyl-2-(4-carbo-d-2-octyloxyphenyl)-pyrimidine, m.p. 19°, is obtained.

The following are prepared in an analogous manner:
5-Dodecyl-2-(4-carbo-d-2-octyloxyphenyl)-pyrimidine
5-Undecyl-2-(4-carbo-d-2-octyloxyphenyl)-pyrimidine
5-Decyl-2-(4-carbo-d-2-octyloxyphenyl)-pyrimidine
5-Nonyl-2-(4-carbo-d-2-octyloxyphenyl)-pyrimidine m.p. 15°
5-Octyl-2-(4-carbo-d-2-octyloxyphenyl)-pyrimidine
5-Hexyl-2-(4-carbo-d-2-octyloxyphenyl)-pyrimidine
5-Pentyl-2-(4-carbo-d-2-octyloxyphenyl)-pyrimidine
5-Butyl-2-(4-carbo-d-2-octyloxyphenyl)-pyrimidine
5-Propyl-2-(4-carbo-d-2-octyloxyphenyl)-pyrimidine
5-Ethyl-2-(4-carbo-d-2-octyloxyphenyl)-pyrimidine
5-Dodecyl-2-[4-carbo-(S-2-methyl-1-butoxy)-phenyl]-pyrimidine
5-Undecyl-2-[4-carbo-(S-2-methyl-1-butoxy)-phenyl]-pyrimidine
5-Decyl-2-[4-carbo-(S-2-methyl-1-butoxy)-phenyl]-pyrimidine
5-Nonyl-2-[4-carbo-(S-2-methyl-1-butoxy)-phenyl]-pyrimidine
5-Octyl-2-[4-carbo-(S-2-methyl-1-butoxy)-phenyl]-pyrimidine
5-Heptyl-2-[4-carbo-(S-2-methyl-1-butoxy)-phenyl]-pyrimidine, m.p. 55.5°
5-Hexyl-2-[4-carbo-(S-2-methyl-1-butoxy)-phenyl]-pyrimidine
5-Pentyl-2-[4-carbo-(S-2-methyl-1-butoxy)-phenyl]-pyrimidine
5-Butyl-2-[4-carbo-(S-2-methyl-1-butoxy)-phenyl]-pyrimidine
5-Propyl-2-[4-carbo-(S-2-methyl-1-butoxy)-phenyl]-pyrimidine
5-Ethyl-2-[4-carbo-(S-2-methyl-1-butoxy)-phenyl]-pyrimidine
R-(2-Chloropropyl)-p-(5-nonylpyrimidin-2-yl)-benzoate
R-(2-Chloropropyl)-p-(5-decylpyrimidin-2-yl)-benzoate
R-(2-Chloropropyl)-p-(5-undecylpyrimidin-2-yl)-benzoate
R-(2-Chloropropyl)-p-(5-dodecylpyrimidin-2-yl)-benzoate
R-(2-Chloropropyl)-p-(5-octylpyrimidin-2-yl)-benzoate
R-(2-Chloropropyl)-p-(5-heptylpyrimidin-2-yl)-benzoate
R-(2-Chloropropyl)-p-(5-hexylpyrimidin-2-yl)-benzoate
R-(2-Chloropropyl)-p-(5-pentylpyrimidin-2-yl)-benzoate
R-(2-Chloropropyl)-p-(5-butylpyrimidin-2-yl)-benzoate.

EXAMPLE 3

Esterification of 27.2 g of p-(5-n-hexylpyrimid-2-yl)phenol with S-4-(2-methylbutyl)-benzoic acid in dichloromethane with the addition of 25.0 g of dicyclohexylcarbodiimide gives rise, after the usual working up, to S-4-(5-n-hexylpyrimid-2-yl)-phenyl 4-(2-methylbutyl)-benzoate.

The following are prepared in an analogous manner:
S-4-(5-Propylpyrimid-2-yl)phenyl 4-(2-methylbutyl)-benzoate
S-4-(5-Butylpyrimid-2-yl)phenyl 4-(2-methylbutyl)-benzoate
S-4-(5-Pentylpyrimid-2-yl)phenyl 4-(2-methylbutyl)-benzoate
S-4-(5-Heptylpyrimid-2-yl)phenyl 4-(2-methylbutyl)-benzoate
S-4-(5-Octylpyrimid-2-yl)phenyl 4-(2-methylbutyl)-benzoate
S-4-(5-Nonylpyrimid-2-yl)phenyl 4-(2-methylbutyl)-benzoate
S-4-(5-decylpyrimid-2-yl)phenyl 4-(2-methylbutyl)-benzoate
S-4-(5-Undecylpyrimid-2-yl)phenyl 4-(2-methylbutyl)-benzoate
S-4-(5-Dodecylpyrimid-2-yl)phenyl 4-(2-methylbutyl)-benzoate
4-(2-Methylbutyl)phenyl S-4-(5-propylpyrimid-2-yl)benzoate
4-(2-Methylbutyl)phenyl S-4-(5-butylpyrimid-2-yl)-benzoate
4-(2-Methylbutyl)phenyl S-4-(5-pentylpyrimid-2-yl)-benzoate
4-(2-Methylbutyl)phenyl S-4-(5-hexylpyrimid-2-yl)-benzoate
4-(2-Methylbutyl)phenyl S-4-(5-heptylpyrimid-2-yl)-benzoate
4-(2-Methylbutyl)phenyl S-4-(5-octylpyrimid-2-yl)-benzoate
4-(2-Methylbutyl)phenyl S-4-(5-nonylpyrimid-2-yl)-benzoate
4-(2-Methylbutyl)phenyl S-4-(5-decylpyrimid-2-yl)-benzoate
4-(2-Methylbutyl)phenyl S-4-(5-undecylpyrimid-2-yl)-benzoate
4-(2-Methylbutyl)phenyl S-4-(5-dodecylpyrimid-2-yl)-benzoate

EXAMPLE 4

Esterification of 17.9 ... (sic) of 5-n-butylpyrimidine-2-carboxylic acid with 16.4 g of S-4-(2-methylbutyl)-phenol in di-chloromethane with the addition of 25.0 g of dicyclohexyl-carbodiimide gives rise, after the usual working up, to S-4-(2-methylbutyl)phenyl 5-butyl-pyrimidine-2-carboxylate.

The following were prepared in an analogous manner:
S-4-(2-Methylbutyl)phenyl 5-propylpyridine-2-carboxylate
S-4-(2-Methylbutyl)phenyl 5-pentylpyridine-2-carboxylate
S-4-(2-Methylbutyl)phenyl 5-hexylpyridine-2-carboxylate
S-4-(2-Methylbutyl)phenyl 5-heptylpyridine-2-carboxylate S-4-(2-Methylbutyl)phenyl 5-octylpyridine-2-carboxylate
S-4-(2-Methylbutyl)phenyl 5-nonylpyridine-2-carboxylate
S-4-(2-Methylbutyl)phenyl 5-decylpyridine-2-carboxylate
S-4-(2-Methylbutyl)phenyl 5-undecylpyridine-2-carboxylate
S-4-(2-Methylbutyl)phenyl 5-dodecylpyridine-2-carboxylate
S-4-(2-Methylbutyl)phenyl 5-propylpyrimidine-2-carboxylate
S-4-(2-Methylbutyl)phenyl 5-pentylpyrimidine-2-carboxylate
S-4-(2-Methylbutyl)phenyl 5-hexylpyrimidine-2-carboxylate
S-4-(2-Methylbutyl)phenyl 5-heptylpyrimidine-2-carboxylate
S-4-(2-Methylbutyl)phenyl 5-octylpyrimidine-2-carboxylate
S-4-(2-Methylbutyl)phenyl 5-nonylpyrimidine-2-carboxylate
S-4-(2-Methylbutyl)phenyl 5-decylpyrimidine-2-carboxylate
S-4-(2-Methylbutyl)phenyl 5-undecylpyrimidine-2-carboxylate
S-4-(2-Methylbutyl)phenyl 5-dodecylpyrimidine-2-carboxylate

EXAMPLE 5

In accordance with the procedure referred to in Example 3, 28.0 g of the carboxylic acid obtainable from the known 4-(5-n-hexylpyrazin-2-yl)-benzonitrile (Japanese Preliminary Published Application 43,961/1983) by saponification with alcoholic potassium hydroxide, followed by neutralization with dilute hydrochloric acid, are treated with 25.0 g of dicyclohexylcarbodiimide and 13.0 g of R-2-octanol. R-2-Octyl 4-(5-n-hexylpyrazin-2-yl)benzoate is obtained after the usual working up.

The following are prepared in a analogous manner:
R-2-Octyl 4-(5-propylpyrazin-2-yl)benzoate
R-2-Octyl 4-(5-butylpyrazin-2-yl)benzoate
R-2-Octyl 4-(5-pentylpyrazin-2-yl)benzoate
R-2-Octyl 4-(5-hepylpyrazin-2-yl)benzoate
R-2-Octyl 4-(5-octylpyrazin-2-yl)benzoate
R-2-Octyl 4-(5-nonylpyrazin-2-yl)benzoate
R-2-Octyl 4-(5-decylpyrazin-2-yl)benzoate
R-2-Octyl 4-(5-undecylpyrazin-2-yl)benzoate
R-2-Octyl 4-(5-dodeylpyrazin-2-yl)benzoate.

EXAMPLE 6

The solution prepared according to Grignard from 2.4 g of magnesium, 15.1 g of S-2-methylbutyl bromide and 200 ml of THF is treated with a solution of 26.1 g of 4-(5-n-hexylpyrazin-2-yl)-benzonitrile. The residue remaining from the organic phase after the solvent has been distilled off, is worked up in the usual manner. The optically active 3-methylvaleryl-4-(5-n-hexylpyrazin-2-yl)benzene is obtained.

The following are prepared in an analogous manner:
3-Methylvaleryl-4-(5-n-propylpyrazin-2-yl)-benzene
3-Methylvaleryl-4-(5-n-butylpyrazin-2-yl)-benzene
3-Methylvaleryl-4-(5-n-pentylpyrazin-2-yl)-benzene
3-Methylvaleryl-4-(5-n-heptylpyrazin-2-yl)-benzene
3-Methylvaleryl-4-(5-n-octylpyrazin-2-yl)-benzene
3-Methylvaleryl-4-(5-n-nonylpyrazin-2-yl)-benzene
3-Methylvaleryl-4-(5-n-decylpyrazin-2-yl)-benzene
3-Methylvaleryl-4-(5-n-undecylpyrazin-2-yl)-benzene
3-Methylvaleryl-4-(5-n-dodecylpyrazin-2-yl)-benzene

EXAMPLE 7

A liquid crystalline phase consisting of
38.3% of 2-p-Nonyloxyphenyl-5-nonylpyrimidine,
2.0% of 2-p-Hexyloxyphenyl-5-nonylpyrimidine,
36.1% of 2-p-Decyloxyphenyl-5-heptylpyrimidine,
5.9% of 2-p-Nonyloxyphenyl-5-heptylpyrimidine,
5.9% of 2-p-Octyloxyphenyl-5-heptylpyrimidine,
5.9% of 2-p-Heptyloxyphenyl-5-heptylpyrimidine, and
5.9% of 2-p-Hexyloxyphenyl-5-heptylpyrimidine
is doped with various amounts of the chiral compound R-4-(5-hexylpyrimid-2-yl)phenyl 2-chloropropionate. The phase transition temperatures as well as the values of the spontaneous polarization of the resultant mixtures are given in the table below:
Addition of X% of the chiral dopant

| x | S$_C^*$ | S$_A^*$ | Ch | I | P |
|---|---|---|---|---|---|
| 3 | 48.1 | | 65 | 68.7 | 1.08 |
| 6 | 41.0 | | 64.1 | 68.1 | 2.14 |
| 10 | 34.5 | | 63 | 68 | 3.12 |

EXAMPLE 8

A mixture of 23.6 g of p-(5-n-heptylpyrimidin-2-yl)cinnamic acid (m.p. 201°, obtainable by boiling for 48 hours a mixture of 22.2 g of 2-p-bromophenyl-5-n-heptylpyrimidine, 18.4 g of triethylamine, 9.2 g of acrylic acid, 0.17 g of Pd(II) acetate, 0.6 g of tritolylphosphine and 75 ml of acetonitrile, followed by cooling to 0°, filtering off with suction, washing of the precipitate with acetonitrile and water and recrystallization from toluene), 13.0 g of R-2-octanol and 25.0 g of dicyclohexylcarbodiimide in the THF is boiled for 24 hours in the presence of dimethylaminopyridine and worked up in the usual manner. 2-Octyl R-p-(5-n-heptylprimidin-2-yl)cinnamate, m.p. 40°, c.p. 58°, is obtained.

The following are prepared in an analogous manner:
2-Octyl R-p-(5-propylpyrimidin-2-yl)cinnamate
2-Octyl R-p-(5-butylpyrimidin-2-yl)cinnamate
2-Octyl R-p-(5-pentylpyrimidin-2-yl)cinnamate
2-Octyl R-p-(5-hexylpyrimidin-2-yl)cinnamate
2-Octyl R-p-(5-octylpyrimidin-2-yl)cinnamate
2-Octyl R-p-(5-nonylpyrimidin-2-yl)cinnamate
2-Octyl R-p-(5-decylpyrimidin-2-yl)cinnamate
2-Octyl R-p-(5-undecylpyrimidin-2-yl)cinnamate
2-Octyl R-p-(5-dodecylpyrimidin-2-yl)cinnamate
2-Methylbutyl R-p-(5-propylpyrimidin-2-yl)cinnamate
2-Methylbutyl R-p-(5-butylpyrimidin-2-yl)cinnamate
2-Methylbutyl R-p-(5-pentylpyrimidin-2-yl)cinnamate
2-Methylbutyl R-p-(5-hexylpyrimidin-2-yl)cinnamate
2-Methylbutyl R-p-(5-heptylpyrimidin-2-yl)cinnamate m.p. 58°, c.p. 96°
2-Methylbutyl R-p-(5-octylpyrimidin-2-yl)cinnamate
2-Methylbutyl R-p-(5-nonylpyrimidin-2-yl)cinnamate
2-Methylbutyl R-p-(5-decylpyrimidin-2-yl)cinnamate
2-Methylbutyl R-p-(5-undecylpyrimidin-2-yl)cinnamate
2-Methylbutyl R-p-(5-dodecylpyrimidin-2-yl)cinnamate

EXAMPLE 9

26.3 g of (S)-3-chlorobutyl-1-tosylate, preparable from p-toluenesulfonyl chloride and (S)-3-chlorobutan-1-ol, and 27.2 g of 4-(5-n-hexylpyrimidin-2-yl)phenol are added to a suspension of 40 g of potassium carbonate in 200 ml of acetone. After 24 hours' boiling under reflux, the reaction mixture is filtered, the filtrate is free from solvent and the residue is twice recrystallized from ethanol. (S)-2-[p-(3-Chlorobutyloxy)phenyl]-5-n-hexylpyrimidine is obtained.

The following are obtained in an analogous manner:
2-[p-(3-Chlorobutyloxy)-phenyl]-5-n-butylpyrimidine
2-[p-(3-Chlorobutyloxy)-phenyl]-5-n-pentylpyrimidine
2-[p-(3-Chlorobutyloxy)-phenyl]-5-n-heptylpyrimidine
2-[p-(3-Chlorobutyloxy)-phenyl]-5-n-octylpyrimidine
2-[p-(3-Chlorobutyloxy)-phenyl]-5-n-nonylpyrimidine
2-[p-(3-Chlorobutyloxy)-phenyl]-5-n-decylpyrimidine
2-[p-(3-Chlorobutyloxy)-phenyl]-5-n-undecylpyrimidine
2-[p-(3-Chlorobutyloxy)-phenyl]-5-n-dodecylpyrimidine 2-[p-(3-Cyanobutyloxy)-phenyl]-5-n-butylpyrimidine
2-[p-(3-Cyanobutyloxy)-phenyl]-5-n-pentylpyrimidine
2-[p-(3-Cyanobutyloxy)-phenyl]-5-n-hexylpyrimidine
2-[p-(3-Cyanobutyloxy)-phenyl]-5-n-heptylpyrimidine
2-[p-(3-Cyanobutyloxy)-phenyl]-5-n-octylpyrimidine
2-[p-(3-Cyanobutyloxy)-phenyl]-5-n-nonylpyrimidine
2-[p-(3-Cyanobutyloxy)-phenyl]-5-n-decylpyrimidine
2-[p-(3-Cyanobutyloxy)-phenyl]-5-n-undecylpyrimidine
2-[p-(3-Cyanobutyloxy)-phenyl]-5-n-dodecylpyrimidine

EXAMPLE 10

A mixture of 40 g of (S)-4,4-dichloro-2-(p-heptyloxyphenyl)-5-(2-methylbutyl)-pyrimidine [obtainable by reacting (S)-2-methylbutyl bromide with diethyl malonate in the presence of sodium methanolate, followed by condensation of the resultant diethyl (S)-2-methylbutyl malonate with p-heptyloxybenzamidine hydrochloride, and reacting the resultant (S)-4,6-dihydroxy-2-(p-heptyloxyphenyl)-5-(2-methylbutyl)-pyrimidine with phosphoroxy trichloride and dimethylaniline], 400 ml of methanol, 40 ml of triethylamine and 20 g of Pd-C (5%) is hydrogenated at room temperature under normal pressure until the theoretical amount of hydrogen has been taken up. After filtering off the catalyst and distilling off the solvent, the residue is recrystallized from ethanol. (S)-2-(p-Heptyloxyphenyl)-5-(2-methylbutyl)-pyrimidine is obtained.

The following are prepared in an analogous manner:
2-(p-Pentyloxyphenyl)-5-(2-methylbutyl)-pyrimidine
2-(p-Hexyloxyphenyl)-5-(2-methylbutyl)-pyrimidine
2-(p-Octyloxyphenyl)-5-(2-methylbutyl)-pyrimidine
2-(p-Nonyloxyphenyl)-5-(2-methylbutyl)-pyrimidine
2-(p-Decyloxyphenyl)-5-(2-methylbutyl)-pyrimidine
2-(p-Undecyloxyphenyl)-5-(2-methylbutyl)-pyrimidine
2-(p-Dodecyloxyphenyl)-5-(2-methylbutyl)-pyrimidine

EXAMPLE 11

A mixture of 8 gr of (S,S)-3-methyl-2-chloropentanoic acid, 16 g of p-(5-n-octylpyrimidin-2-yl)phenol, 11.6 g of N,N-dicyclohexylcarbodiimide, 0.6 g of 4-N,N-dimethylaminopyridine and 300 ml of dichloromethane is stirred overnight at room temperature. After filtering off the precipitated urea derivative, the filtrate is washed with dilute hydrochloric acid and water, and the organic phase is worked up in the usual manner. p-(5-n-Octylpyrimidin-2-yl)-phenyl (S,S)-3-methyl-2-chloropentanoate is obtained.

The following are prepared in an analogous manner:
p-(5-Pentylpyrimidin-2-yl)phenyl 3-methyl-2-chloropentanoate
p-(5-Hexylpyrimidin-2-yl)phenyl 3-methyl-2-chloropentanoate
p-(5-Heptylpyrimidin-2-yl)phenyl 3-methyl-2-chloropentanoate
p-(5-Nonylpyrimidin-2-yl)phenyl 3-methyl-2-chloropentanoate
p-(5-Decylpyrimidin-2-yl)phenyl 3-methyl-2-chloropentanoate
p-(5-Pentylpyrimidin-2-yl)phenyl 3-methyl-2-bromopentanoate
p-(5-Hexylpyrimidin-2-yl)phenyl 3-methyl-2-bromopentanoate
p-(5-Heptylpyrimidin-2-yl)phenyl 3-methyl-2-bromopentanoate
p-(5-Octylpyrimidin-2-yl)phenyl 3-methyl-2-bromopentanoate
p-(5-Nonylpyrimidin-2-yl)phenyl 3-methyl-2-bromopentanoate
p-(5-Decylpyrimidin-2-yl)phenyl 3-methyl-2-bromopentanoate
p-(5-Pentylpyrazin-2-yl)phenyl 3-methyl-2-chloropentanoate
p-(5-Hexylpyrazin-2-yl)phenyl 3-methyl-2-chloropentanoate
p-(5-Heptylpyrazin-2-yl)phenyl 3-methyl-2-chloropentanoate
p-(5-Octylpyrazin-2-yl)phenyl 3-methyl-2-chloropentanoate
p-(5-Nonylpyrazin-2-yl)phenyl 3-methyl-2-chloropentanoate
p-(5-Decylpyrazin-2-yl)phenyl 3-methyl-2-chloropentanoate
p-(5-Pentylpyrazin-2-yl)phenyl 3-methyl-2-cyanopentanoate
p-(5-Hexylpyrazin-2-yl)phenyl 3-methyl-2-cyanopentanoate
p-(5-Heptylpyrazin-2-yl)phenyl 3-methyl-2-cyanopentanoate
p-(5-Octylpyrazin-2-yl)phenyl 3-methyl-2-cyanopentanoate
p-(5-Nonylpyrazin-2-yl)phenyl 3-methyl-2-cyanopentanoate
p-(5-Decylpyrazin-2-yl)phenyl 3-methyl-2-cyanopentanoate
p-(5-Pentylpyrimidin-2-yl)phenyl 3-methyl-2-chlorohexanecarboxylate
p-(5-Hexylpyrimidin-2-yl)phenyl 3-methyl-2-chlorohexanecarboxylate
p-(5-Heptylpyrimidin-2-yl)phenyl 3-methyl-2-chlorohexanecarboxylate
p-(5-Octylpyrimidin-2-yl)phenyl 3-methyl-2-chlorohexanecarboxylate
p-(5-Nonylpyrimidin-2-yl)phenyl 3-methyl-2-chlorohexanecarboxylate
p-(5-Decylpyrimidin-2-yl)phenyl 3-methyl-2-chlorohexanecarboxylate
p-(5-Pentylpyrimidin-2-yl)phenyl 3-methyl-2-cyanohexanecarboxylate
p-(5-Hexylpyrimidin-2-yl)phenyl 3-methyl-2-cyanohexanecarboxylate
p-(5-Heptylpyrimidin-2-yl)phenyl 3-methyl-2-cyanohexanecarboxylate
p-(5-Octylpyrimidin-2-yl)phenyl 3-methyl-2-cyanohexanecarboxylate
p-(5-Nonylpyrimidin-2-yl)phenyl 3-methyl-2-cyanohexanecarboxylate
p-(5-Decylpyrimidin-2-yl)phenyl 3-methyl-2-cyanohexanecarboxylate p-(5-Pentylpyrimidin-2-yl)phenyl 3-chloro-2-methylpentanoate
p-(5-Hexylpyrimidin-2-yl)phenyl 3-chloro-2-methylpentanoate
p-(5-Heptylpyrimidin-2-yl)phenyl 3-chloro-2-methylpentanoate
p-(5-Octylpyrimidin-2-yl)phenyl 3-chloro-2-methylpentanoate
p-(5-Nonylpyrimidin-2-yl)phenyl 3-chloro-2-methylpentanoate
p-(5-Decylpyrimidin-2-yl)phenyl 3-chloro-2-methylpentanoate
p-(5-Pentylpyrazin-2-yl)phenyl 3-bromo-2-methylpentanoate
p-(5-Hexylpyrazin-2-yl)phenyl 3-bromo-2-methylpentanoate
p-(5-Heptylpyrazin-2-yl)phenyl 3-bromo-2-methylpentanoate
p-(5-Octylpyrazin-2-yl)phenyl 3-bromo-2-methylpentanoate
p-(5-nonylpyrazin-2-yl)phenyl 3-bromo-2-methylpentanoate
p-(5-Decylpyrazin-2-yl)phenyl 3-bromo-2-methylpentanoate
p-(5-Pentylpyrimidin-2-yl)phenyl 3-cyano-2-methylhexanoate
p-(5-Hexylpyrimidin-2-yl)phenyl 3-cyano-2-methylhexanoate
p-(5-Heptylpyrimidin-2-yl)phenyl 3-cyano-2-methylhexanoate
p-(5-Octylpyrimidin-2-yl)phenyl 3-cyano-2-methylhexanoate
p-(5-Nonylpyrimidin-2-yl)phenyl 3-cyano-2-methylhexanoate
p-(5-Decylpyrimidin-2-yl)phenyl 3-cyano-2-methylhexanoate.

EXAMPLE 12

0.01 mol of optically active 1-[4-(5-heptylpyrimidin-2-yl)phenyl-1]propan-2-ol (prepared from commercial R-propylene oxide and 4-(5-heptylpyrimidin-2-yl)phenylmagnesium bromide) is stirred together with 0.01 mol of butyric acid, 2.3 g of dicyclohexylcarbodiimide, 0.2 g of 4-N,N-dimethylaminopyridine and 25 ml of dichloromethane at room temperature for 48 hours.

The mixture is then cooled in an icebath, and the precipitate of dicyclohexylurea is filtered off with suction and washed with dichloromethane. The combined filtrates are evaporated and chromatographed over silica gel. After recrystallization, optically active 1-[4-(5-(5-heptylpyrimidin-2-yl)-phenyl]-2-propyl butyrate is obtained.

The following are prepared in an analogous manner:
1-[4-(5-Propylpyrimidin-(2)-yl)phenyl]-2-propyl butyrate
1-[4-(5-Butylpyrimidin-(2)-yl)phenyl]-2-propyl butyrate
1-[4-(5-Pentylpyrimidin-(2)-yl)phenyl]-2-propyl butyrate
1-[4-(5-Hexylpyrimidin-(2)-yl)phenyl]-2-propyl butyrate
1-[4-(5-Octylpyrimidin-(2)-yl)phenyl]-2-propyl butyrate
1-[4-(5-Nonylpyrimidin-(2)-yl)phenyl]-2-propyl butyrate
1-[4-(5-Propyloxypyrimidin-(2)-yl)phenyl]-2-propyl butyrate
1-[4-(5-Butyloxypyrimidin-(2)-yl)phenyl]-2-propyl butyrate
1-[4-(5-Pentyloxypyrimidin-(2)-yl)phenyl]-2-propyl butyrate
1-[4-(5-Hexyloxypyrimidin-(2)-yl)phenyl]-2-propyl butyrate
1-[4-(5-Heptyloxypyrimidin-(2)-yl)phenyl]-2-propyl butyrate
1-[4-(5-Octyloxypyrimidin-(2)-yl)phenyl]-2-propyl butyrate
1-[4-(5-Nonyloxypyrimidin-(2)-yl)phenyl]-2-propyl butyrate
1-[4-(5-Propylpyrimidin-(2)-yl)phenyl]2-propyl propionate
1-[4-(5-Butylpyrimidin-(2)-yl)phenyl]2-propyl propionate
1-[4-(5-Pentylpyrimidin-(2)-yl)phenyl]2-propyl propionate
1-[4-(5-Hexylpyrimidin-(2)-yl)phenyl]2-propyl propionate
1-[4-(5-Heptylpyrimidin-(2)-yl)phenyl]2-propyl propionate
1-[4-(5-Octylpyrimidin-(2)-yl)phenyl]2-propyl propionate
1-[4-(5-Nonylpyrimidin-(2)-yl)phenyl]2-propyl propionate
1-[4-(5-Propyloxypyrimidin-(2)-yl)phenyl]2-propyl propionate
1-[4-(5-Butyloxypyrimidin-(2)-yl)phenyl]2-propyl propionate
1-[4-(5-Pentyloxypyrimidin-(2)-yl)phenyl]2-propyl propionate
1-[4-(5-Hexyloxypyrimidin-(2)-yl)phenyl]2-propyl propionate
1-[4-(5-Heptyloxypyrimidin-(2)-yl)phenyl]2-propyl propionate
1-[4-(5-Octyloxypyrimidin-(2)-yl)phenyl]2-propyl propionate
1-[4-(5-Nonyloxypyrimidin-(2)-yl)phenyl]2-propyl propionate
1-[4-(5-Propylpyrimidin-(2)-yl)phenyl]2-propyl valerate
1-[4-(5-Butylpyrimidin-(2)-yl)phenyl]2-propyl valerate
1-[4-(5-Pentylpyrimidin-(2)-yl)phenyl]2-propyl valerate
1-[4-(5-Hexylpyrimidin-(2)-yl)phenyl]2-propyl valerate
1-[4-(5-Heptylpyrimidin-(2)-yl)phenyl]2-propyl valerate
1-[4-(5-Octylpyrimidin-(2)-yl)phenyl]2-propyl valerate
1-[4-(5-Nonylpyrimidin-(2)-yl)phenyl]2-propyl valerate
1-[4-(5-Propyloxypyrimidin-(2)-yl)phenyl]2-propyl valerate
1-[4-(5-Butyloxypyrimidin-(2)-yl)phenyl]2-propyl valerate
1-[4-(5-Pentyloxypyrimidin-(2)-yl)phenyl]2-propyl valerate
1-[4-(5-Hexyloxypyrimidin-(2)-yl)phenyl]2-propyl valerate
1-[4-(5-Heptyloxypyrimidin-(2)-yl)phenyl]2-propyl valerate
1-[4-(5-Octyloxypyrimidin-(2)-yl)phenyl]2-propyl valerate
1-[4-(5-Nonyloxypyrimidin-(2)-yl)phenyl]2-propyl valerate
1-[4-(5-Propylpyrimidin-(2)-yl)phenyl]2-propyl acetate
1-[4-(5-Butylpyrimidin-(2)-yl)phenyl]2-propyl acetate
1-[4-(5-Pentylpyrimidin-(2)-yl)phenyl]2-propyl acetate
1-[4-(5-Hexylpyrimidin-(2)-yl)phenyl]2-propyl acetate
1-[4-(5-Heptylpyrimidin-(2)-yl)phenyl]2-propyl acetate
1-[4-(5-Octylpyrimidin-(2)-yl)phenyl]2-propyl acetate
1-[4-(5-Nonylpyrimidin-(2)-yl)phenyl]2-propyl acetate 1-[4-(5-Propyloxypyrimidin-(2)-yl)phenyl]2-propyl acetate
1-[4-(5-Butyloxypyrimidin-(2)-yl)phenyl]2-propyl acetate
1-[4-(5-Pentyloxypyrimidin-(2)-yl)phenyl]2-propyl acetate
1-[4-(5-Hexyloxypyrimidin-(2)-yl)phenyl]2-propyl acetate
1-[4-(5-Heptyloxypyrimidin-(2)-yl)phenyl]2-propyl acetate
1-[4-(5-Octyloxypyrimidin-(2)-yl)phenyl]2-propyl acetate
1-[4-(5-Nonyloxypyrimidin-(2)-yl)phenyl]2-propyl acetate
1-[4-(5-Propylphenyl)pyrazin-(2)-yl]-2-propyl acetate
1-[4-(5-Butylphenyl)pyrazin-(2)-yl]-2-propyl acetate
1-[4-(5-Pentylphenyl)pyrazin-(2)-yl]-2-propyl acetate
1-[4-(5-Hexylphenyl)pyrazin-(2)-yl]-2-propyl acetate
1-[4-(5-Heptylphenyl)pyrazin-(2)-yl]-2-propyl acetate
1-[4-(5-Octylphenyl)pyrazin-(2)-yl]-2-propyl acetate
1-[4-(5-Nonylphenyl)pyrazin-(2)-yl]-2-propyl acetate
1-[4-(5-Propyloxyphenyl)pyrazin-(2)-yl]-2-propyl acetate
1-[4-(5-Butyloxyphenyl)pyrazin-(2)-yl]-2-propyl acetate
1-[4-(5-Pentyloxyphenyl)pyrazin-(2)-yl]-2-propyl acetate
1-[4-(5-Hexyloxyphenyl)pyrazin-(2)-yl]-2-propyl acetate
1-[4-(5-Heptyloxyphenyl)pyrazin-(2)-yl]-2-propyl acetate
1-[4-(5-Octyloxyphenyl)pyrazin-(2)-yl]-2-propyl acetate
1-[4-(5-Nonyloxyphenyl)pyrazin-(2)-yl]-2-propyl acetate
1-[4-(5-Propylphenyl)pyrazin-(2)-yl]-2-propyl propionate
1-[4-(5-Butylphenyl)pyrazin-(2)-yl]-2-propyl propionate
1-[4-(5-Pentylphenyl)pyrazin-(2)-yl]-2-propyl propionate
1-[4-(5-Hexylphenyl)pyrazin-(2)-yl]-2-propyl propionate
1-[4-(5-Heptylphenyl)pyrazin-(2)-yl]-2-propyl propionate
1-[4-(5-Octylphenyl)pyrazin-(2)-yl]-2-propyl propionate
1-[4-(5-Nonylphenyl)pyrazin-(2)-yl]-2-propyl propionate
1-[4-(5-Propyloxyphenyl)pyrazin-(2)-yl]-2-propyl propionate
1-[4-(5-Butyloxyphenyl)pyrazin-(2)-yl]-2-propyl propionate
1-[4-(5-Pentyloxyphenyl)pyrazin-(2)-yl]-2-propyl propionate
1-[4-(5-Hexyloxyphenyl)pyrazin-(2)-yl]-2-propyl propionate
1-[4-(5-Heptyloxyphenyl)pyrazin-(2)-yl]-2-propyl propionate
1-[4-(5-Octyloxyphenyl)pyrazin-(2)-yl]-2-propyl propionate
1-[4-(5-Nonyloxyphenyl)pyrazin-(2)-yl]-2-propyl propionate
1-[4-(5-Propylphenyl)pyrazin-(2)-yl]-2-propyl butyrate
1-[4-(5-Butylphenyl)pyrazin-(2)-yl]-2-propyl butyrate
1-[4-(5-Pentylphenyl)pyrazin-(2)-yl]-2-propyl butyrate
1-[4-(5-Hexylphenyl)pyrazin-(2)-yl]-2-propyl butyrate
1-[4-(5-Heptylphenyl)pyrazin-(2)-yl]-2-propyl butyrate
1-[4-(5-Octylphenyl)pyrazin-(2)-yl]-2-propyl butyrate
1-[4-(5-Nonylphenyl)pyrazin-(2)-yl]-2-propyl butyrate
1-[4-(5-Proployoxyphenyl)pyrazin-(2)-yl]-2-propyl butyrate
1-[4-(5-Butyloxyphenyl)pyrazin-(2)-yl]-2-propyl butyrate
1-[4-(5-Pentyloxyphenyl)pyrazin-(2)-yl]-2-propyl butyrate
1-[4-(5-Hexyloxyphenyl)pyrazin-(2)-yl]-2-propyl butyrate
1-[4-(5-Heptyloxyphenyl)pyrazin-(2)-yl]-2-propyl butyrate
1-[4-(5-Octyloxyphenyl)pyrazin-(2)-yl]-2-propyl butyrate
1-[4-(5-Nonyloxyphenyl)pyrazin-(2)-yl]-2-propyl butyrate
1-[4-(5-Propylphenyl)pyrazin-(2)-yl]-2-propyl valerate
1-[4-(5-Butylphenyl)pyrazin-(2)-yl]-2-propyl valerate
1-[4-(5-Pentylphenyl)pyrazin-(2)-yl]-2-propyl valerate
1-[4-(5-Hexylphenyl)pyrazin-(2)-yl]-2-propyl valerate
1-[4-(5-Heptylphenyl)pyrazin-(2)-yl]-2-propyl valerate
1-[4-(5-Octylphenyl)pyrazin-(2)-yl]-2-propyl valerate
1-[4-(5-Nonylphenyl)pyrazin-(2)-yl]-2-propyl valerate
1-[4-(5-Propyloxyphenyl)pyrazin-(2)-yl]-2-propyl valerate
1-[4-(5-Butyloxyphenyl)pyrazin-(2)-yl]-2-propyl valerate
1-[4-(5-Pentyloxyphenyl)pyrazin-(2)-yl]-2-propyl valerate
1-[4-(5-Hexyloxyphenyl)pyrazin-(2)-yl]-2-propyl valerate
1-[4-(5-Heptyloxyphenyl)pyrazin-(2)-yl]-2-propyl valerate
1-[4-(5-Octyloxyphenyl)pyrazin-(2)-yl]-2-propyl valerate
1-[4-(5-Nonyloxyphenyl)pyrazin-(2)-yl]-2-propyl valerate.

EXAMPLE 13

0.01 mol of dextrorotatory 3-[4-(5-heptylpyrimidin-(2)-yl)phenyl]butyric acid, obtained by hydrogenation of the corresponding 2-butenoic acid over 5% Pd/carbon in tetrahydrofuran and racemic splitting with (+)-ephedrine (2-methylamino-1-phenylpropan-1-ol), $\alpha_D^{20} = +3.3°$, is esterified with 0.01 mol of optically active 2-octanol in a manner analogous to that of Example 12. After purification by chromatography and recrystallization, 2-octyl 3-[4-(5-heptylpyrimidin-(2)-yl)phenyl]butyrate is obtained.

The following are prepared in an analogous manner:
2-Octyl 3-[4-(5-propylpyrimidin-(2)-yl)phenyl]butyrate
2-Octyl 3-[4-(5-butylpyrimidin-(2)-yl)phenyl]butyrate
2-Octyl 3-[4-(5-pentylpyrimidin-(2)-yl)phenyl]butyrate
2-Octyl 3-[4-(5-hexylpyrimidin-(2)-yl)phenyl]butyrate
2-Octyl 3-[4-(5-octylpyrimidin-(2)-yl)phenyl]butyrate
2-Octyl 3-[4-(5-nonylpyrimidin-(2)-yl)phenyl]butyrate
2-Octyl 3-[4-(5-propyloxypyrimidin-(2)-yl)phenyl]butyrate
2-Octyl 3-[4-(5-butyloxypyrimidin-(2)-yl)phenyl]butyrate
2-Octyl 3-[4-(5-pentyloxypyrimidin-(2)-yl)phenyl]butyrate
2-Octyl 3-[4-(5-hexyloxypyrimidin-(2)-yl)phenyl]butyrate
2-Octyl 3-[4-(5-heptyloxypyrimidin-(2)-yl)phenyl]butyrate
2-Octyl 3-[4-(5-octyloxypyrimidin-(2)-yl)phenyl]butyrate 2-Octyl 3-[4-(5-nonyloxypyrimidin-(2)-yl)phenyl]butyrate
Hexyl 3-[4-(5-propylpyrimidin-(2)-yl)phenyl]butyrate
Hexyl 3-[4-(5-butylpyrimidin-(2)-yl)phenyl]butyrate
Hexyl 3-[4-(5-pentylpyrimidin-(2)-yl)phenyl]butyrate
Hexyl 3-[4-(5-hexylpyrimidin-(2)-yl)phenyl]butyrate
Hexyl 3-[4-(5-heptylpyrimidin-(2)-yl)phenyl]butyrate
Hexyl 3-[4-(5-octylpyrimidin-(2)-yl)phenyl]butyrate
Hexyl 3-[4-(5-nonylpyrimidin-(2)-yl)phenyl]butyrate
Hexyl 3-[4-(5-proployxpyrimidin-(2)-yl)phenyl]butyrate
Hexyl 3-[4-(5-butyloxypyrimidin-(2)-yl)phenyl]butyrate
Hexyl 3-[4-(5-pentyloxypyrimidin-(2)-yl)phenyl]butyrate
Hexyl 3-[4-(5-hexyloxypyrimidin-(2)-yl)phenyl]butyrate
Hexyl 3-[4-(5-heptyloxypyrimidin-(2)-yl)phenyl]butyrate
Hexyl 3-[4-(5-octyloxypyrimidin-(2)-yl)phenyl]butyrate
Hexyl 3-[4-(5-nonyloxypyrimidin-(2)-yl)phenyl]butyrate
2-Methylbutyl 3-[4-(5-propylpyrimidin-(2)-yl)phenyl]butyrate
2-Methylbutyl 3-[4-(5-butylpyrimidin-(2)-yl)phenyl]butyrate
2-Methylbutyl 3-[4-(5-pentylpyrimidin-(2)-yl)phenyl]butyrate
2-Methylbutyl 3-[4-(5-hexylpyrimidin-(2)-yl)phenyl]butyrate
2-Methylbutyl 3-[4-(5-heptylpyrimidin-(2)-yl)phenyl]butyrate
2-Methylbutyl 3-[4-(5-octylpyrimidin-(2)-yl)phenyl]butyrate
2-Methylbutyl 3-[4-(5-nonylpyrimidin-(2)-yl)phenyl]butyrate
2-Methylbutyl 3-[4-(5-propyloxypyrimidin-(2)-yl)phenyl]butyrate
2-Methylbutyl 3-[4-(5-butyloxypyrimidin-(2)-yl)phenyl]butyrate
2-Methylbutyl 3-[4-(5-pentyloxypyrimidin-(2)-yl)phenyl]butyrate
2-Methylbutyl 3-[4-(5-hexyloxypyrimidin-(2)-yl)phenyl]butyrate
2-Methylbutyl 3-[4-(5-heptyloxypyrimidin-(2)-yl)phenyl]butyrate
2-Methylbutyl 3-[4-(5-octyloxypyrimidin-(2)-yl)phenyl]butyrate
2-Methylbutyl 3-[4-(5-nonyloxypyrimidin-(2)-yl)phenyl]butyrate.

EXAMPLE 14

0.01 mol of 4-(5-hexylpyrimidin-(2)-yl)phenyl α-chloropropionate (Example 1) is heated with 0.001 mol of sodium heptanolate in 20 ml of N-methylpyrrolidone for 2 hours at 80°. The mixture is then poured onto water and is extracted with toluene and the extract evaporated. After purification by chromatography and recrystallization, 4-(5-hexylpyrimidin-(2)-yl)phenyl α-heptyloxypropionate is obtained.

The following are prepared in an analogous manner:
4-(5-Propylpyrimidin-(2)-yl)phenyl α-heptyloxypropionate
4-(5-Butylpyrimidin-(2)-yl)phenyl α-heptyloxypropionate
4-(5-Pentylpyrimidin-(2)-yl)phenyl α-heptyloxypropionate
4-(5-Heptylpyrimidin-(2)-yl)phenyl α-heptyloxypropionate
4-(5-Octylpyrimidin-(2)-yl)phenyl α-heptyloxypropionate
4-(5-Nonylpyrimidin-(2)-yl)phenyl α-heptyloxypropionate
4-(5-Propyloxypyrimidin-(2)-yl)phenyl α-heptyloxypropionate
4-(5-Butyloxypyrimidin-(2)-yl)phenyl α-heptyloxypropionate
4-(5-Pentyloxypyrimidin-(2)-yl)phenyl α-heptyloxypropionate
4-(5-Hexyloxypyrimidin-(2)-yl)phenyl α-heptyloxypropionate
4-(5-Heptyloxypyrimidin-(2)-yl)phenyl α-heptyloxypropionate
4-(5-Octyloxypyrimidin-(2)-yl)phenyl α-heptyloxypropionate
4-(5-Nonyloxypyrimidin-(2)-yl)phenyl α-heptyloxypropionate
4-(5-Propylpyrimidin-(2)-yl)phenyl α-octyloxypropionate
4-(5-Butylpyrimidin-(2)-yl)phenyl α-octyloxypropionate
4-(5-Pentylpyrimidin-(2)-yl)phenyl α-octyloxypropionate
4-(5-Hexylpyrimidin-(2)-yl)phenyl α-octyloxypropionate
4-(5-Heptylpyrimidin-(2)-yl)phenyl α-octyloxypropionate
4-(5-Octylpyrimidin-(2)-yl)phenyl α-octyloxypropionate
4-(5-Nonylpyrimidin-(2)-yl)phenyl α-octyloxypropionate
4-(5-Propyloxypyrimidin-(2)-yl)phenyl α-octyloxypropionate
4-(5-Butyloxypyrimidin-(2)-yl)phenyl α-octyloxypropionate
4-(5-Pentyloxypyrimidin-(2)-yl)phenyl α-octyloxypropionate
4-(5-Hexyloxypyrimidin-(2)-yl)phenyl α-octyloxypropionate
4-(5-Heptyloxypyrimidin-(2)-yl)phenyl α-octyloxypropionate
4-(5-Octyloxypyrimidin-(2)-yl)phenyl α-octyloxypropionate
4-(5-Nonyloxypyrimidin-(2)-yl)phenyl α-octyloxypropionate
4-(5-Propylpyrimidin-(2)-yl)phenyl α-hexyloxypropionate
4-(5-Butylpyrimidin-(2)-yl)phenyl α-hexyloxypropionate
4-(5-Pentylpyrimidin-(2)-yl)phenyl α-hexyloxypropionate
4-(5-Hexylpyrimidin-(2)-yl)phenyl α-hexyloxypropionate
4-(5-Heptylpyrimidin-(2)-yl)phenyl α-hexyloxypropionate
4-(5-Octylpyrimidin-(2)-yl)phenyl α-hexyloxypropionate
4-(5-Nonylpyrimidin-(2)-yl)phenyl α-hexyloxypropionate
4-(5-Propyloxypyrimidin-(2)-yl)phenyl α-hexyloxypropionate
4-(5-Butyloxypyrimidin-(2)-yl)phenyl α-hexyloxypropionate
4-(5-Pentyloxypyrimidin-(2)-yl)phenyl α-hexyloxypropionate
4-(5-Hexyloxypyrimidin-(2)-yl)phenyl α-hexyloxypropionate 4-(5-Heptyloxypyrimidin-(2)-yl)phenyl α-hexyloxypropionate
4-(5-Octyloxypyrimidin-(2)-yl)phenyl α-hexyloxypropionate
4-(5-Nonyloxypyrimidin-(2)-yl)phenyl α-hexyloxypropionate
4-(5-Propylpyrimidin-(2)-yl)phenyl α-pentyloxypropionate
4-(5-Butylpyrimidin-(2)-yl)phenyl α-pentyloxypropionate
4-(5-Pentylpyrimidin-(2)-yl)phenyl α-pentyloxypropionate
4-(5-Hexylpyrimidin-(2)-yl)phenyl α-pentyloxypropionate
4-(5-Heptylpyrimidin-(2)-yl)phenyl α-pentyloxypropionate
4-(5-Octylpyrimidin-(2)-yl)phenyl α-pentyloxypropionate
4-(5-Nonylpyrimidin-(2)-yl)phenyl α-pentyloxypropionate
4-(5-Propyloxypyrimidin-(2)-yl)phenyl α-pentyloxypropionate
4-(5-Butyloxypyrimidin-(2)-yl)phenyl α-pentyloxypropionate
4-(5-Pentyloxypyrimidin-(2)-yl)phenyl α-pentyloxypropionate
4-(5-Hexyloxypyrimidin-(2)-yl)phenyl α-pentyloxypropionate
4-(5-Heptyloxypyrimidin-(2)-yl)phenyl α-pentyloxypropionate
4-(5-Octyloxypyrimidin-(2)-yl)phenyl α-pentyloxypropionate
4-(5-Nonyloxypyrimidin-(2)-yl)phenyl α-pentyloxypropionate
4-(5-Propylpyrimidin-(2)-yl)phenyl α-butyloxypropionate
4-(5-Butylpyrimidin-(2)-yl)phenyl α-butyloxypropionate
4-(5-Pentylpyrimidin-(2)-yl)phenyl α-butyloxypropionate
4-(5-Hexylpyrimidin-(2)-yl)phenyl α-butyloxypropionate
4-(5-Heptylpyrimidin-(2)-yl)phenyl α-butyloxypropionate
4-(5-Octylpyrimidin-(2)-yl)phenyl α-butyloxypropionate
4-(5-Nonylpyrimidin-(2)-yl)phenyl α-butyloxypropionate
4-(5-Propyloxypyrimidin-(2)-yl)phenyl α-butyloxypropionate
4-(5-Butyloxypyrimidin-(2)-yl)phenyl α-butyloxypropionate
4-(5-Pentyloxypyrimidin-(2)-yl)phenyl α-butyloxypropionate
4-(5-Hexyloxypyrimidin-(2)-yl)phenyl α-butyloxypropionate
4-(5-Heptyloxypyrimidin-(2)-yl)phenyl α-butyloxypropionate
4-(5-Octyloxypyrimidin-(2)-yl)phenyl α-butyloxypropionate
4-(5-Nonyloxypyrimidin-(2)-yl)phenyl α-butyloxypropionate
4-(5-Propylpyrimidin-(2)-yl)phenyl α-propyloxypropionate
4-(5-Butylpyrimidin-(2)-yl)phenyl α-propyloxypropionate
4-(5-Pentylpyrimidin-(2)-yl)phenyl α-propyloxypropionate
4-(5-Hexylpyrimidin-(2)-yl)phenyl α-propyloxypropionate
4-(5-Heptylpyrimidin-(2)-yl)phenyl α-propyloxypropionate
4-(5-Octylpyrimidin-(2)-yl)phenyl α-propyloxypropionate
4-(5-Nonylpyrimidin-(2)-yl)phenyl α-propyloxypropionate
4-(5-Propyloxypyrimidin-(2)-yl)phenyl α-propyloxypropionate
4-(5-Butyloxypyrimidin-(2)-yl)phenyl α-propyloxypropionate
4-(5-Pentyloxypyrimidin-(2)-yl)phenyl α-propyloxypropionate
4-(5-Hexyloxypyrimidin-(2)-yl)phenyl α-propyloxypropionate
4-(5-Heptyloxypyrimidin-(2)-yl)phenyl α-propyloxypropionate
4-(5-Octyloxypyrimidin-(2)-yl)phenyl α-propyloxypropionate
4-(5-Nonyloxypyrimidin-(2)-yl)phenyl α-propyloxypropionate
4-(5-Propylpyrimidin-(2)-yl)phenyl α-ethyloxypropionate
4-(5-Butylpyrimidin-(2)-yl)phenyl α-ethyloxypropionate
4-(5-Pentylpyrimidin-(2)-yl)phenyl α-ethyloxypropionate
4-(5-Hexylpyrimidin-(2)-yl)phenyl α-ethyloxypropionate
4-(5-Heptylpyrimidin-(2)-yl)phenyl α-ethyloxypropionate
4-(5-Octylpyrimidin-(2)-yl)phenyl α-ethyloxypropionate
4-(5-Nonylpyrimidin-(2)-yl)phenyl α-ethyloxypropionate
4-(5-Propyloxypyrimidin-(2)-yl)phenyl α-ethyloxypropionate
4-(5-Butyloxypyrimidin-(2)-yl)phenyl α-ethyloxypropionate
4-(5-Pentyloxypyrimidin-(2)-yl)phenyl α-ethyloxypropionate
4-(5-Hexyloxypyrimidin-(2)-yl)phenyl α-ethyloxypropionate
4-(5-Heptyloxypyrimidin-(2)-yl)phenyl α-ethyloxypropionate
4-(5-Octyloxypyrimidin-(2)-yl)phenyl α-ethyloxypropionate
4-(5-Nonyloxypyrimidin-(2)-yl)phenyl α-ethyloxypropionate
4-(5-Propylpyrimidin-(2)-yl)phenyl α-methyloxypropionate
4-(5-Butylpyrimidin-(2)-yl)phenyl α-methyloxypropionate
4-(5-Pentylpyrimidin-(2)-yl)phenyl α-methyloxypropionate
4-(5-Hexylpyrimidin-(2)-yl)phenyl α-methyloxypropionate
4-(5-Heptylpyrimidin-(2)-yl)phenyl α-methyloxypropionate
4-(5-Octylpyrimidin-(2)-yl)phenyl α-methyloxypropionate
4-(5-Nonylpyrimidin-(2)-yl)phenyl α-methyloxypropionate
4-(5-Propyloxypyrimidin-(2)-yl)phenyl α-methyloxypropionate
4-(5-Butyloxypyrimidin-(2)-yl)phenyl α-methyloxypropionate 4-(5-Pentyloxypyrimidin-(2)-yl)phenyl α-methyloxypropionate 4-(5-Hexyloxypyrimidin-(2)-yl)phenyl α-methyloxypropionate 4-(5-Heptyloxypyrimidin-(2)-yl)phenyl α-methyloxypropionate 4-(5-Octyloxypyrimidin-(2)-yl)phenyl α-methyloxypropionate 4-(5-Nonyloxypyrimidin-(2)-yl)phenyl α-methyloxypropionate.

EXAMPLE 15

0.01 mol of 1-{[4-(5-heptylpyrimidin-(2)-yl)phenyl-(1)]-ethylenyl-(2)} 4-octyl-(2)-benzoate ($\alpha_D^{20}$: +39.0°, c=2 in $CH_2Cl_2$) is hydrogenated in 50 ml of tetrahydrofuran with 2 g of 5% Pd on carbon at room temperature under normal pressure until the calculated amount of hydrogen is taken up. After filtration, evaporation and recrystallization, 1-{[4-(5-heptylpyrimidin-(2)-yl)phenyl-(1)]ethyl-(2)} 4-octyl-(2)-benzoate is obtained, m.p. 44.5°, $\alpha_D^{20}$=18.9°, $S_A$/I 71°.

The following are prepared in an analogous manner:

1-{[4-(5-Propylpyrimidin-(2)-yl)phenyl-(1)]ethyl-(2)} 4-octyl-(2)-benzoate
1-{[4-(5-Butylpyrimidin-(2)-yl)phenyl-(1)]ethyl-(2)} 4-octyl-(2)-benzoate
1-{[4-(5-Pentylpyrimidin-(2)-yl)phenyl-(1)]ethyl-(2)} 4-octyl-(2)-benzoate
1-{[4-(5-Hexylpyrimidin-(2)-yl)phenyl-(1)]ethyl-(2)} 4-octyl-(2)-benzoate
1-{[4-(5-Octylpyrimidin-(2)-yl)phenyl-(1)]ethyl-(2)} 4-octyl-(2)-benzoate
1-{[4-(5-Nonylpyrimidin-(2)-yl)phenyl-(1)]ethyl-(2)} 4-octyl-(2)-benzoate
1-{[4-(5-Propyloxypyrimidin-(2)-yl)phenyl-(1)]ethyl-(2)} 4-octyl-(2)-benzoate
1-{[4-(5-Butyloxypyrimidin-(2)-yl)phenyl-(1)]ethyl-(2)} 4-octyl-(2)-benzoate
1-{[4-(5-Pentyloxypyrimidin-(2)-yl)phenyl-(1)]ethyl-(2)} 4-octyl-(2)-benzoate
1-{[4-(5-Hexyloxypyrimidin-(2)-yl)phenyl-(1)]ethyl-(2)} 4-octyl-(2)-benzoate
1-{[4-(5-Heptyloxypyrimidin-(2)-yl)phenyl-(1)]ethyl-(2)} 4-octyl-(2)-benzoate
1-{[4-(5-Octyloxypyrimidin-(2)-yl)phenyl-(1)]ethyl-(2)} 4-octyl-(2)-benzoate
1-{[4-(5-Nonyloxypyrimidin-(2)-yl)phenyl-(1)]ethyl-(2)} 4-octyl-(2)-benzoate

EXAMPLE 16

0.01 mol of laevorotatory 3-[4-(5-heptylpyrimidin-(2)-yl)phenyl-(1)]-2-methylpropionic acid ($\alpha_D^{20}$=−2.3°), obtained by racemic splitting with (+)-ephedrine and synthesis of the racemic acid by hydrogenation of the corresponding α-methylcinnamic acid over 5% Pd/carbon in tetrahydrofuran, is esterified with 0.01 mol of 1-hexanol by a method analysis to Example 12. After working up and purification, n-hexyl 3-[4-(5-heptylpyrimidin-(2)-yl)phenyl-(1)]-2-methylpropionate is obtained.

The following are prepared in an analogous manner:
Hexyl 3-[4-(5-propylpyrimidin-(2)-yl)phenyl-(1)]-2-methylpropionate
Hexyl 3-[4-(5-butylpyrimidin-(2)-yl)phenyl-(1)]-2-methylpropionate
Hexyl 3-[4-(5-pentylpyrimidin-(2)-yl)phenyl-(1)]-2-methylpropionate
Hexyl 3-[4-(5-hexylpyrimidin-(2)-yl)phenyl-(1)]-2-methylpropionate
Hexyl 3-[4-(5-octylpyrimidin-(2)-yl)phenyl-(1)]-2-methylpropionate
Hexyl 3-[4-(5-nonylpyrimidin-(2)-yl)phenyl-(1)]-2-methylpropionate
Hexyl 3-[4-(5-propyloxypyrimidin-(2)-yl)phenyl-(1)]-2-methylpropionate
Hexyl 3-[4-(5-butyloxypyrimidin-(2)-yl)phenyl-(1)]-2-methylpropionate
Hexyl 3-[4-(5-pentyloxypyrimidin-(2)-yl)phenyl-(1)]-2-methylpropionate
Hexyl 3-[4-(5-hexyloxypyrimidin-(2)-yl)phenyl-(1)]-2-methylpropionate
Hexyl 3-[4-(5-heptyloxypyrimidin-(2)-yl)phenyl-(1)]-2-methylpropionate
Hexyl 3-[4-(5-octyloxypyrimidin-(2)-yl)phenyl-(1)]-2-methylpropionate
Hexyl 3-[4-(5-nonyloxypyrimidin-(2)-yl)phenyl-(1)]-2-methylpropionate
2-Methylbutyl 3-[4-(5-nonylpyrimidin-(2)-phenyl-(1)-2-methylpropionate
2-Methylbutyl 3-[4-(5-propyloxypyrimidin-(2)-phenyl-(1)-2-methylpropionate
2-Methylbutyl 3-[4-(5-butyloxypyrimidin-(2)-phenyl-(1)-2-methylpropionate
2-Methylbutyl 3-[4-(5-pentyloxypyrimidin-(2)-phenyl-(1)-2-methylpropionate
2-Methylbutyl 3-[4-(5-hexyloxypyrimidin-(2)-phenyl-(1)-2-methylpropionate
2-Methylbutyl 3-[4-(5-heptyloxypyrimidin-(2)-phenyl-(1)-2-methylpropionate
2-Methylbutyl 3-[4-(5-octyloxypyrimidin-(2)-phenyl-(1)-2-methylpropionate
2-Methylbutyl 3-[4-(5-nonyloxypyrimidin-(2)-phenyl-(1)-2-methylpropionate

EXAMPLE 17

0.01 mol of 2-methylbutyl R-p-(5-heptylpyrimidin-2-yl)cinnamate (compare Example 8) are hydrogenated in 50 ml of tetrahydrofuran with 2 g of 5% Pd on carbon at room temperature under normal pressure, until the calculated amount of hydrogen is taken up. The mixture is then filtered, the filtrate evaporated and the residue recrystallized; 2-methylbutyl R-p-(5-heptylpyrimidin-2-yl)-phenylpropionate is obtained, m.p. 16°.

The following are prepared in an analogous manner:
2-Methylbutyl R-p-(5-propylpyrimidin-2-yl)phenylpropionate
2-Methylbutyl R-p-(5-butylpyrimidin-2-yl)phenylpropionate
2-Methylbutyl R-p-(5-pentylpyrimidin-2-yl)phenylpropionate
2-Methylbutyl R-p-(5-hexylpyrimidin-2-yl)phenylpropionate
2-Methylbutyl R-p-(5-octylpyrimidin-2-yl)phenylpropionate
2-Methylbutyl R-p-(5-decylpyrimidin-2-yl)phenylpropionate
2-Octyl R-p-(5-propylpyrimidin-2-yl)phenylpropionate
2-Octyl R-p-(5-butylpyrimidin-2-yl)phenylpropionate
2-Octyl R-p-(5-pentylpyrimidin-2-yl)phenylpropionate
2-Octyl R-p-(5-hexylpyrimidin-2-yl)phenylpropionate
2-Octyl R-p-(5-heptylpyrimidin-2-yl)phenylpropionate
2-Octyl R-p-(5-octylpyrimidin-2-yl)phenylpropionate
2-Octyl R-p-(5-decylpyrimidin-2-yl)phenylpropionate

EXAMPLE 18

7.9 ml of diethyl azodicarboxylate are added at room temperature to a solution of 0.05 mol of 2-(4-hydroxyphenyl)-5-nonylpyrimidine, 5.8 ml of ethyl (s)-lactate and 3.1 g of triphenylphosphine in 150 ml of tetrahydrofuran. The mixture is stirred overnight and evaporated. The residue is taken up in 30 ml of 90% methanol and 50 ml of methylene chloride, and 5 ml of $H_2O_2$ are added. After 15 minutes, hydrated $Na_2S_2O_5$ is added, followed by 100 ml of water. The organic phase is washed and dried.

After evaporation and chromatography on silica gel, optically active ethyl 2-[p-(5-nonylpyrimidin-2-yl)phenoxypropanoate is obtained.

The following are prepared in an analogous manner:
Ethyl 2-[p-(5-propylpyrimidin-2-yl)phenoxy]-propanoate
Ethyl 2-[p-(5-butylpyrimidin-2-yl)phenoxy]-propanoate
Ethyl 2-[p-(5-pentylpyrimidin-2-yl)phenoxy]-propanoate
Ethyl 2-[p-(5-hexylpyrimidin-2-yl)phenoxy]-propanoate
Ethyl 2-[p-(5-heptylpyrimidin-2-yl)phenoxy]-propanoate
Ethyl 2-[p-(5-octylpyrimidin-2-yl)phenoxy]-propanoate
Ethyl 2-[p-(5-propyloxypyrimidin-2-yl)phenoxy]-propanoate
Ethyl 2-[p-(5-butyloxypyrimidin-2-yl)phenoxy]-propanoate
Ethyl 2-[p-(5-pentyloxypyrimidin-2-yl)phenoxy]-propanoate
Ethyl 2-[p-(5-hexyloxypyrimidin-2-yl)phenoxy]-propanoate
Ethyl 2-[p-(5-heptyloxypyrimidin-2-yl)phenoxy]-propanoate
Ethyl 2-[p-(5-octyloxypyrimidin-2-yl)phenoxy]-propanoate
Ethyl 2-[p-(5-nonyloxypyrimidin-2-yl)phenoxy]-propanoate

EXAMPLE 19

Etherification of 2-(4-hydroxyphenyl)-5-nonylpyrimidine with 2-octyl bromide in dimethylformamide in the presence of potassium carbonate gives 2-[4-(2-octyloxy)phenyl]-5-nonylpyrimidin.

The following are prepared in an analogous manner:
2-[4-(2-Octyloxy)phenyl]-5-propylpyrimidine
2-[4-(2-Octyloxy)phenyl]-5-butylpyrimidine
2-[4-(2-Octyloxy)phenyl]-5-pentylpyrimidine
2-[4-(2-Octyloxy)phenyl]-5-hexylpyrimidine
2-[4-(2-Octyloxy)phenyl]-5-heptylpyrimidine
2-[4-(2-Octyloxy)phenyl]-5-octylpyrimidine
2-[4-(2-Octyloxy)phenyl]-5-propyloxypyrimidine
2-[4-(2-Octyloxy)phenyl]-5-butyloxypyrimidine
2-[4-(2-Octyloxy)phenyl]-5-pentyloxypyrimidine
2-[4-(2-Octyloxy)phenyl]-5-hexyloxypyrimidine
2-[4-(2-Octyloxy)phenyl]-5-heptyloxypyrimidine
2-[4-(2-Octyloxy)phenyl]-5-octyloxypyrimidine
2-[4-(2-Octyloxy)phenyl]-5-nonyloxypyrimidine
2-[4-(2-Methylbutyloxy)phenyl]-5-propylpyrimidine
2-[4-(2-Methylbutyloxy)phenyl]-5-butylpyrimidine
2-[4-(2-Methylbutyloxy)phenyl]-5-pentylpyrimidine
2-[4-(2-Methylbutyloxy)phenyl]-5-hexylpyrimidine
2-[4-(2-Methylbutyloxy)phenyl]-5-heptylpyrimidine
2-[4-(2-Methylbutyloxy)phenyl]-5-octylpyrimidine
2-[4-(2-Methylbutyloxy)phenyl]-5-nonylpyrimidine
2-[4-(2-Methylbutyloxy)phenyl]-5-propyloxypyrimidine
2-[4-(2-Methylbutyloxy)phenyl]-5-butyloxypyrimidine
2-[4-(2-Methylbutyloxy)phenyl]-5-pentyloxypyrimidine
2-[4-(2-Methylbutyloxy)phenyl]-5-hexyloxypyrimidine
2-[4-(2-Methylbutyloxy)phenyl]-5-heptyloxypyrimidine
2-[4-(2-Methylbutyloxy)phenyl]-5-octyloxypyrimidine
2-[4-(2-Methylbutyloxy)phenyl]-5-nonyloxypyrimidine

EXAMPLE 20

A mixture of 11.9 g of 2-p-hydroxyphenyl-5-n-nonylpyrimidine, 10.2 g of p-(2-methylbutoxy)benzyl bromide (preparable from 4-hydroxybenzaldehyde and 2-methylbutylmesylate in the presence of potassium carbonate in DMF, followed by reduction of the benzaldehyde to benzyl alcohol and reacting it with $PBr_3$ to give the corresponding benzyl bromide), 8.6 g of potassium carbonate and 50 ml of dimethylformamide is heated for 10 hours at 90°. The usual working up gives optically active 4-(5-n-nonylpyrimidin-2-yl)phenyl p-(2-methylbutoxy)benzyl ether, S-Ch 103°, CH-I 105°.

The following are prepared in an analogous manner:
4-(5-Hexylpyrimidin-2-yl)phenyl p-(2-methylbutoxy)benzyl ether
4-(5-Heptylpyrimidin-2-yl)phenyl p-(2-methylbutoxy)benzyl ether
4-(5-Octylpyrimidin-2-yl)phenyl p-(2-methylbutoxy)benzyl ether
4-(5-Decylpyrimidin-2-yl)phenyl p-(2-methylbutoxy)benzyl ether
4-(5-Pentylpyrimidin-2-yl)phenyl p-(2-methylbutoxy)benzyl ether
4-(5-Butylpyrimidin-2-yl)phenyl p-(2-methylbutoxy)benzyl ether
4-(5-Propylpyrimidin-2-yl)phenyl p-(2-methylbutoxy)benzyl ether

EXAMPLE 21

In an analogous manner to Example 20, 4-(5-n-nonylpyrimidin-2-yl)phenyl p-(2-methylbutoxycarbonyl)benzyl ether, m.p., 29°, is obtained from 2-p-hydroxyphenyl-5-n-nonylpyrimidine and 2-methylbutyl p-bromomethylbenzoate (preparable by azeotropic esterification of p-bromomethylbenzoic acid with 2-methyl-1-butanol).

The following are prepared in an analogous manner:
4-(5-Hexylpyrimidin-2-yl)phenyl p-(2-methylbutoxycarbonyl)benzyl ether
4-(5-Heptylpyrimidin-2-yl)phenyl p-(2-methylbutoxycarbonyl)benzyl ether
4-(5-Octylpyrimidin-2-yl)phenyl p-(2-methylbutoxycarbonyl)benzyl ether
4-(5-Decylpyrimidin-2-yl)phenyl p-(2-methylbutoxycarbonyl)benzyl ether
4-(5-Pentylpyrimidin-2-yl)phenyl p-(2-methylbutoxycarbonyl)benzyl ether
4-(5-Butylpyrimidin-2-yl)phenyl p-(2-methylbutoxycarbonyl)benzyl ether
4-(5-Propylpyrimidin-2-yl)phenyl p-(2-methylbutoxycarbonyl)benzyl ether
4-(5-Propylpyrimidin-2-yl)phenyl p-(2-octyloxycarbonyl)benzyl ether
4-(5-Butylpyrimidin-2-yl)phenyl p-(2-octyloxycarbonyl)benzyl ether
4-(5-Pentylpyrimidin-2-yl)phenyl p-(2-octyloxycarbonyl)benzyl ether
4-(5-Hexylpyrimidin-2-yl)phenyl p-(2-octyloxycarbonyl)benzyl ether 4-(5-Heptylpyrimidin-2-yl)phenyl p-(2-octyloxycarbonyl)benzyl ether
4-(5-Octylpyrimidin-2-yl)phenyl p-(2-octyloxycarbonyl)benzyl ether
4-(5-Nonylpyrimidin-2-yl)phenyl p-(2-octyloxycarbonyl)benzyl ether
4-(5-Decylpyrimidin-2-yl)phenyl p-(2-octyloxycarbonyl)benzyl ether

EXAMPLE 22

0.04 mol of 5-heptyl-2-(4-styryl)pyrimidine, prepared by methods known per se, and 0.04 mol of 2-octyl 4-bromobenzoate, prepared from 4-bromobenzoic acid and d-2-octanol, are heated under reflux with 0.08 mol of triethylamine, 0.1 g of palladium(II) acetate and 0.24 g of o-tolyphosphine in 50 ml of acetonitrile for 24 hours. After evaporation, chromatography on silica gel and recrystallization, oct-2-yl 4-{1-[4-(5-heptylpyrimidin-2-yl)phenyl]ethylenyl-(2)} benzoate is obtained, $\alpha_D^{20} = 39.0°$.

The following are prepared in an analogous manner:
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propyloxypyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate
Oct-2-yl 4-{1-[4-(5-propylpyrimidin-2-yl)-phenyl]ethylen-2-yl}-benzoate

EXAMPLE 23

A mixture of 0.7 g of optically active 5-[p-(2-methylbutoxy)phenyl]pyrazin-2-ol, 0.6 g of p-octylbenzoic acid chloride and 5 ml of pyridine is stirred overnight. After the usual working up, optically active 2-p-octylbenzoyloxy-5-(2-methylbutoxy)phenylpyrazine is obtained, m.p. 53°, c.p. 134°.

The following are prepared in an analogous manner:
2-p-Propylbenzoyloxy-5-(2-methylbutoxy)phenylpyrazine
2-p-Butylbenzoyloxy-5-(2-methylbutoxy)phenylpyrazine, m.p. 78°, c.p. 142°
2-p-Pentylbenzoyloxy-5-(2-methylbutoxy)phenylpyrazine, m.p. 66°, c.p. 148°
2-p-Hexylbenzoyloxy-5-(2-methylbutoxy)phenylpyrazine
2-p-Heptylbenzoyloxy-5-(2-methylbutoxy)phenylpyrazine, m.p. 63°, c.p. 140°
2-p-Nonylbenzoyloxy-5-(2-methylbutoxy)phenylpyrazine
2-p-Decylbenzoyloxy-5-(2-methylbutoxy)phenylpyrazine, m.p. 68°, c.p. 130°
2-p-Undecylbenzoyloxy-5-(2-methylbutoxy)phenylpyrazine
2-p-Dodecylbenzoyloxy-5-(2-methylbutoxy)phenylpyrazine
2-p-Propoxybenzoyloxy-5-(2-methylbutoxy)phenylpyrazine
2-p-Butoxybenzoyloxy-5-(2-methylbutoxy)phenylpyrazine
2-p-Pentoxybenzoyloxy-5-(2-methylbutoxy)phenylpyrazine
2-p-Hexoxybenzoyloxy-5-(2-methylbutoxy)phenylpyrazine
2-p-Heptoxybenzoyloxy-5-(2-methylbutoxy)phenylpyrazine
2-p-Octoxybenzoyloxy-5-(2-methylbutoxy)phenylpyrazine, m.p. 116°, c.p. 162°
2-p-Nonoxybenzoyloxy-5-(2-methylbutoxy)phenylpyrazine
2-p-Decoxybenzoyloxy-5-(2-methylbutoxy)phenylpyrazine
2-p-Undecoxybenzoyloxy-5-(2-methylbutoxy)phenylpyrazine, m.p. 104°, c.p. 151°
2-p-Dodecoxybenzoyloxy-5-(2-methylbutoxy)phenylpyrazine
2-p-Propionyloxybenzoyloxy-5-(2-methylbutoxy)phenylpyrazine
2-p-Butyryloxybenzoyloxy-5-(2-methylbutoxy)phenylpyrazine
2-p-Hexanoyloxybenzoyloxy-5-(2-methylbutoxy)phenylpyrazine
2-p-Octanoyloxybenzoyloxy-5-(2-methylbutoxy)phenylpyrazine
2-p-Nonanoyloxybenzoyloxy-5-(2-methylbutoxy)phenylpyrazine
2-p-Decanoyloxybenzoyloxy-5-(2-methylbutoxy)phenylpyrazine
2-p-Butoxycarbonyloxybenzoyloxy-5-(2-methylbutoxy)phenylpyrazine
2-p-Pentoxycarbonyloxybenzoyloxy-5-(2-methylbutoxy)phenylpyrazine
2-p-Hexoxycarbonyloxybenzoyloxy-5-(2-methylbutoxy)phenylpyrazine
2-p-Octoxycarbonyloxybenzoyloxy-5-(2-methylbutoxy)phenylpyrazine
2-p-Nonoxycarbonyloxybenzoyloxy-5-(2-methylbutoxy)phenylpyrazine, m.p. 84°, c.p. 148°
2-p-Decoxycarbonyloxybenzoyloxy-5-(2-methylbutoxy)phenylpyrazine
2-p-Propoxy-5-(2-methylbutoxy)phenylpyrazine
2-p-Butoxy-5-(2-methylbutoxy)phenylpyrazine
2-p-Pentoxy-5-(2-methylbutoxy)phenylpyrazine
2-p-Hexoxy-5-(2-methylbutoxy)phenylpyrazine
2-p-Heptoxy-5-(2-methylbutoxy)phenylpyrazine
2-p-Nonoxy-5-(2-methylbutoxy)phenylpyrazine
2-p-Decoxy-5-(2-methylbutoxy)phenylpyrazine
2-p-Propionyloxy-5-(2-methylbutoxy)phenylpyrazine
2-p-Butyryloxy-5-(2-methylbutoxy)phenylpyrazine
2-p-Pentanoyloxy-5-(2-methylbutoxy)phenylpyrazine
2-p-Hexanoyloxy-5-(2-methylbutoxy)phenylpyrazine
2-p-Heptanoyloxy-5-(2-methylbutoxy)phenylpyrazine
2-p-Octanoyloxy-5-(2-methylbutoxy)phenylpyrazine
2-p-Nonanoyloxy-5-(2-methylbutoxy)phenylpyrazine
2-p-Decanoyloxy-5-(2-methylbutoxy)phenylpyrazine
2-p-Butoxycarbonyloxy-5-(2-methylbutoxy)phenylpyrazine 2-p-Pentoxycarbonyloxy-5-(2-methylbutoxy)phenylpyrazine
2-p-Hexoxycarbonyloxy-5-(2-methylbutoxy)phenylpyrazine
2-p-Heptoxycarbonyloxy-5-(2-methylbutoxy)phenylpyrazine
2-p-Octoxycarbonyloxy-5-(2-methylbutoxy)phenylpyrazine, c.p. 42°
2-p-Nonoxycarbonyloxy-5-(2-methylbutoxy)phenylpyrazine
2-p-Decoxycarbonyloxy-5-(2-methylbutoxy)phenylpyrazine

EXAMPLE 24

A mixture of 6.3 g of S-2-methylbutanol and 50 ml of benzene is treated with 0.65 g of sodium. 8.1 g of 3-chloro-6-(p-nonylphenyl)pyridazine are added to the resultant alcoholate solution. After four hours' boiling under reflux the mixture is worked up as usual. Optically active 3-(2-methylbutoxy)-6-(p-nonylphenyl)pyridazine is obtained, m.p. 78°.

The following are prepared in an analogous manner:
3-(2-Methylbutoxy)-6-(p-butylphenyl)pyridazine
3-(2-Methylbutoxy)-6-(p-pentylphenyl)pyridazine, m.p. 94°
3-(2-Methylbutoxy)-6-(p-hexylphenyl)pyridazine
3-(2-Methylbutoxy)-6-(p-heptylphenyl)pyridazine
3-(2-Methylbutoxy)-6-(p-octylphenyl)pyridazine
3-(2-Methylbutoxy)-6-(p-decylphenyl)pyridazine
3-(2-Methylbutoxy)-6-(p-undecylphenyl)pyridazine
3-(2-Methylbutoxy)-6-(p-dodecylphenyl)pyridazine, m.p. 78°
3-(2-Methylbutoxy)-6-(p-butoxyphenyl)pyridazine
3-(2-Methylbutoxy)-6-(p-pentoxyphenyl)pyridazine
3-(2-Methylbutoxy)-6-(p-hexoxyphenyl)pyridazine
3-(2-Methylbutoxy)-6-(p-heptoxyphenyl)pyridazine
3-(2-Methylbutoxy)-6-(p-octoxyphenyl)pyridazine, m.p. 91°
3-(2-Methylbutoxy)-6-(p-nonoxyphenyl)pyridazine
3-(2-Methylbutoxy)-6-(p-decoxyphenyl)pyridazine, m.p. 87°
3-(2-Methylbutoxy)-6-(p-undecoxyphenyl)pyridazine
3-(2-Methylbutoxy)-6-(p-dodecoxyphenyl)pyridazine
3-(2-Octyl)-6-(p-butylphenyl)pyridazine
3-(2-Octyl)-6-(p-pentylphenyl)pyridazine, m.p. 55°
3-(2-Octyl)-6-(p-hexylphenyl)pyridazine
3-(2-Octyl)-6-(p-heptylphenyl)pyridazine
3-(2-Octyl)-6-(p-octylphenyl)pyridazine
3-(2-Octyl)-6-(p-decylphenyl)pyridazine
3-(2-Octyl)-6-(p-undecylphenyl)pyridazine
3-(2-Octyl)-6-(p-dodecylphenyl)pyridazine, m.p. 56°
3-(2-Octyl)-6-(p-butoxyphenyl)pyridazine
3-(2-Octyl)-6-(p-pentoxyphenyl)pyridazine
3-(2-Octyl)-6-(p-hexoxyphenyl)pyridazine
3-(2-Octyl)-6-(p-heptoxyphenyl)pyridazine
3-(2-Octyl)-6-(p-octoxyphenyl)pyridazine, m.p. 85°
3-(2-Octyl)-6-(p-nonoxyphenyl)pyridazine
3-(2-Octyl)-6-(p-decoxyphenyl)pyridazine, m.p. 87°
3-(2-Octyl)-6-(p-undecoxyphenyl)pyridazine
3-(2-Octyl)-6-(p-dodecoxyphenyl)pyridazine
3-(2-Methylbutoxyphenyl)-6-butylpyridazine
3-(2-Methylbutoxyphenyl)-6-pentylpyridazine
3-(2-Methylbutoxyphenyl)-6-hexylpyridazine
3-(2-Methylbutoxyphenyl)-6-heptylpyridazine
3-(2-Methylbutoxyphenyl)-6-octylpyridazine
3-(2-Methylbutoxyphenyl)-6-decylpyridazine
3-(2-Methylbutoxyphenyl)-6-undecylpyridazine
3-(2-Methylbutoxyphenyl)-6-dodecylpyridazine
3-(2-Methylbutoxyphenyl)-6-butoxypyridazine
3-(2-Methylbutoxyphenyl)-6-pentoxypyridazine
3-(2-Methylbutoxyphenyl)-6-hexoxypyridazine
3-(2-Methylbutoxyphenyl)-6-heptoxypyridazine
3-(2-Methylbutoxyphenyl)-6-octoxypyridazine
3-(2-Methylbutoxyphenyl)-6-nonoxypyridazine
3-(2-Methylbutoxyphenyl)-6-decoxypyridazine
3-(2-Methylbutoxyphenyl)-6-undecoxypyridazine
3-(2-Methylbutoxyphenyl)-6-dodecoxypyridazine
3-(2-Octyloxyphenyl)-6-butylpyridazine
3-(2-Octyloxyphenyl)-6-pentylpyridazine
3-(2-Octyloxyphenyl)-6-hexylpyridazine
3-(2-Octyloxyphenyl)-6-heptylpyridazine
3-(2-Octyloxyphenyl)-6-octylpyridazine
3-(2-Octyloxyphenyl)-6-decylpyridazine
3-(2-Octyloxyphenyl)-6-undecylpyridazine
3-(2-Octyloxyphenyl)-6-dodecylpyridazine
3-(2-Octyloxyphenyl)-6-butoxypyridazine
3-(2-Octyloxyphenyl)-6-pentoxypyridazine
3-(2-Octyloxyphenyl)-6-hexoxypyridazine
3-(2-Octyloxyphenyl)-6-heptoxypyridazine
3-(2-Octyloxyphenyl)-6-octoxypyridazine
3-(2-Octyloxyphenyl)-6-monoxypyridazine
3-(2-Octyloxyphenyl)-6-decoxypyridazine
3-(2-Octyloxyphenyl)-6-undecoxypyridazine
3-(2-Octyloxyphenyl)-6-dodecoxypyridazine

EXAMPLE 25

6.5 g of heptylmalonodialdehydetetraethylacetal, 5.1 g of optically active 4-(2-methylbutyl)mercaptobenzamidine hydrochloride and 10 ml of dimethylformamide are heated to 150° for 12 hours. The reaction mixture is then taken up in dichloromethane, washed with sodium hydrogen carbonate solution and water until neutral, dried and the solvent is distilled off. Optically active 2-[4-(2-methylbutyl)mercaptophenyl]-5-n-heptylpyrimidine is obtained.

The following are prepared in an analogous manner:
2-[4-(2-Methylbutyl)mercaptophenyl]-5-octylpyrimidine
2-[4-(2-Methylbutyl)mercaptophenyl]-5-nonylpyrimidine
2-[4-(2-Methylbutyl)mercaptophenyl]-5-decylpyrimidine
2-[4-(2-Methylbutyl)mercaptophenyl]-5-undecylpyrimidine
2-[4-(2-Methylbutyl)mercaptophenyl]-5-dodecylpyrimidine
2-[4-(2-Octyl)mercaptophenyl]-5-heptylpyrimidine
2-[4-(2-Octyl)mercaptophenyl]-5-octylpyrimidine
2-[4-(2-Octyl)mercaptophenyl]-5-nonylpyrimidine
2-[4-(2-Octyl)mercaptophenyl]-5-decylpyrimidine
2-[4-(2-Octyl)mercaptophenyl]-5-undecylpyrimidine
2-[4-(2-Octyl)mercaptophenyl]-5-dodecylpyrimidine
2-[4-Dihydrocitronellylmercaptophenyl]-5-heptylpyrimidine
2-[4-Dihydrocitronellylmercaptophenyl]-5-octylpyrimidine
2-[4-Dihydrocitronellylmercaptophenyl]-5-nonylpyrimidine
2-[4-Dihydrocitronellylmercaptophenyl]-5-decylpyrimidine
2-[4-Dihydrocitronellylmercaptophenyl]-5-undecylpyrimidine
2-[4-Dihydrocitronellylmercaptophenyl]-5-dodecylpyrimidine

EXAMPLE 26

A solution of 0.01 mol of optically active 4-(2-methylbutoxy)phenyllithium (prepared from 4-bromo-2-methylbutoxy)benzene and lithium) in 30 ml of toluene is added dropwise, at −20° under nitrogen, to a solution of 0.01 mol of 3-pentylpyridine (which is obtainable by coupling pentylmagnesium bromide and 3-bromopyridine) in 30 ml of toluene. The reaction mixture is heated to boiling for 4 hours, then cooled and carefully hydrolyzed with 10 ml of water. The organic phase is washed with water and saturated NaCl solution, dried over magnesium sulfate and evaporated. The residue is purified chromatographically on a silica gel column with diisopropyl ether as the mobile phase. Optically active 2-p-(2-methylbutoxy)phenyl-5-pentylpyridine is obtained.

The following are prepared in an analogous manner:
2-p-(2-Methylbutoxyphenyl)-5-butylpyridine
2-p-(2-Methylbutoxyphenyl)-5-pentylpyridine
2-p-(2-Methylbutoxyphenyl)-5-hexylpyridine
2-p-(2-Methylbutoxyphenyl)-5-heptylpyridine
2-p-(2-Methylbutoxyphenyl)-5-octylpyridine
2-p-(2-Methylbutoxyphenyl)-5-nonylpyridine
2-p-(2-Methylbutoxyphenyl)-5-decylpyridine
2-p-(2-Methylbutoxyphenyl)-5-undecylpyridine
2-p-(2-Methylbutoxyphenyl)-5-dodecylpyridine
2-p-(2-Methylbutoxyphenyl)-5-heptoxymethylpyridine
2-p-(2-Methylbutoxyphenyl)-5-hexoxyethylpyridine
2-p-(2-Methylbutoxyphenyl)-5-pentoxypropylpyridine
2-p-(3-Methylpentoxyphenyl)-5-butylpyridine
2-p-(3-Methylpentoxyphenyl)-5-pentylpyridine
2-p-(3-Methylpentoxyphenyl)-5-hexylpyridine
2-p-(3-Methylpentoxyphenyl)-5-heptylpyridine
2-p-(3-Methylpentoxyphenyl)-5-octylpyridine
2-p-(3-Methylpentoxyphenyl)-5-nonylpyridine
2-p-(3-Methylpentoxyphenyl)-5-decylpyridine
2-p-(3-Methylpentoxyphenyl)-5-undecylpyridine
2-p-(3-Methylpentoxyphenyl)-5-dodecylpyridine
2-p-(3-Methylpentoxyphenyl)-5-heptoxymethylpyridine
2-p-(3-Methylpentoxyphenyl)-5-hexoxyethylpyridine
2-p-(3-Methylpentoxyphenyl)-5-pentoxypropylpyridine
2-p-(4-Methylhexoxyphenyl)-5-butylpyridine
2-p-(4-Methylhexoxyphenyl)-5-pentylpyridine
2-p-(4-Methylhexoxyphenyl)-5-hexylpyridine
2-p-(4-Methylhexoxyphenyl)-5-heptylpyridine
2-p-(4-Methylhexoxyphenyl)-5-octylpyridine
2-p-(4-Methylhexoxyphenyl)-5-nonylpyridine
2-p-(4-Methylhexoxyphenyl)-5-decylpyridine
2-p-(4-Methylhexoxyphenyl)-5-undecylpyridine
2-p-(4-Methylhexoxyphenyl)-5-dodecylpyridine
2-p-(4-Methylhexoxyphenyl)-5-heptoxymethylpyridine
2-p-(4-Methylhexoxyphenyl)-5-hexoxyethylpyridine
2-p-(4-Methylhexoxyphenyl)-5-pentoxypropylpyridine
2-p-(5-Methylheptoxyphenyl)-5-butylpyridine
2-p-(5-Methylheptoxyphenyl)-5-pentylpyridine
2-p-(5-Methylheptoxyphenyl)-5-hexylpyridine
2-p-(5-Methylheptoxyphenyl)-5-heptylpyridine
2-p-(5-Methylheptoxyphenyl)-5-octylpyridine
2-p-(5-Methylheptoxyphenyl)-5-nonylpyridine
2-p-(5-Methylheptoxyphenyl)-5-decylpyridine
2-p-(5-Methylheptoxyphenyl)-5-undecylpyridine
2-p-(5-Methylheptoxyphenyl)-5-dodecylpyridine
2-p-(5-Methylheptoxyphenyl)-5-heptoxymethylpyridine
2-p-(5-Methylheptoxyphenyl)-5-hexoxymethylpyridine
2-p-(5-Methylheptoxyphenyl)-5-pentoxypropylpyridine
2-p-(6-Methyloctoxyphenyl)-5-butylpyridine
2-p-(6-Methyloctoxyphenyl)-5-pentylpyridine
2-p-(6-Methyloctoxyphenyl)-5-hexylpyridine
2-p-(6-Methyloctoxyphenyl)-5-heptylpyridine
2-p-(6-Methyloctoxyphenyl)-5-octylpyridine
2-p-(6-Methyloctoxyphenyl)-5-nonylpyridine
2-p-(6-Methyloctoxyphenyl)-5-decylpyridine
2-p-(6-Methyloctoxyphenyl)-5-undecylpyridine
2-p-(6-Methyloctoxyphenyl)-5-dodecylpyridine
2-p-(6-Methyloctoxyphenyl)-5-heptoxymethylpyridine
2-p-(6-Methyloctoxyphenyl)-5-hexoxymethylpyridine
2-p-(6-Methyloctoxyphenyl)-5-pentoxypropylpyridine
2-p-(2-Methylbutyryloxyphenyl)-5-butylpyridine
2-p-(2-Methylbutyryloxyphenyl)-5-pentylpyridine
2-p-(2-Methylbutyryloxyphenyl)-5-hexylpyridine
2-p-(2-Methylbutyryloxyphenyl)-5-heptylpyridine
2-p-(2-Methylbutyryloxyphenyl)-5-octylpyridine
2-p-(2-Methylbutyryloxyphenyl)-5-nonylpyridine
2-p-(2-Methylbutyryloxyphenyl)-5-decylpyridine
2-p-(2-Methylbutyryloxyphenyl)-5-undecylpyridine
2-p-(2-Methylbutyryloxyphenyl)-5-dodecylpyridine
2-p-(2-Methylbutyryloxyphenyl)-5-heptoxymethylpyridine
2-p-(2-Methylbutyryloxyphenyl)-5-hexoxyethylpyridine
2-p-(2-Methylbutyryloxyphenyl)-5-pentoxypropylpyridine
2-p-(4-Methylhexanoyloxyphenyl)-5-butylpyridine
2-p-(4-Methylhexanoyloxyphenyl)-5-pentylpyridine
2-p-(4-Methylhexanoyloxyphenyl)-5-hexylpyridine
2-p-(4-Methylhexanoyloxyphenyl)-5-heptylpyridine
2-p-(4-Methylhexanoyloxyphenyl)-5-octylpyridine
2-p-(4-Methylhexanoyloxyphenyl)-5-nonylpyridine
2-p-(4-Methylhexanoyloxyphenyl)-5-decylpyridine
2-p-(4-Methylhexanoyloxyphenyl)-5-undecylpyridine
2-p-(4-Methylhexanoyloxyphenyl)-5-dodecylpyridine
2-p-(4-Methylhexanoyloxyphenyl)-5-heptoxymethylpyridine
2-p-(4-Methylhexanoyloxyphenyl)-5-hexoxyethylpyridine
2-p-(4-Methylhexanoyloxyphenyl)-5-pentoxypropylpyridine
2-p-(6-Methyloctanoyloxyphenyl)-5-butylpyridine
2-p-(6-Methyloctanoyloxyphenyl)-5-pentylpyridine
2-p-(6-Methyloctanoyloxyphenyl)-5-hexylpyridine
2-p-(6-Methyloctanoyloxyphenyl)-5-heptylpyridine
2-p-(6-Methyloctanoyloxyphenyl)-5-octylpyridine
2-p-(6-Methyloctanoyloxyphenyl)-5-nonylpyridine
2-p-(6-Methyloctanoyloxyphenyl)-5-decylpyridine
2-p-(6-Methyloctanoyloxyphenyl)-5-undecylpyridine
2-p-(6-Methyloctanoyloxyphenyl)-5-dodecylpyridine
2-p-(6-Methyloctanoyloxyphenyl)-5-heptoxymethylpyridine
2-p-(6-Methyloctanoyloxyphenyl)-5-hexoxyethylpyridine
2-p-(6-Methyloctanoyloxyphenyl)-5-pentoxypropylpyridine
2-p-(6-Methyloctanoylphenyl)-5-butylpyridine
2-p-(6-Methyloctanoylphenyl)-5-pentylpyridine
2-p-(6-Methyloctanoylphenyl)-5-hexylpyridine
2-p-(6-Methyloctanoylphenyl)-5-heptylpyridine
2-p-(6-Methyloctanoylphenyl)-5-octylpyridine
2-p-(6-Methyloctanoylphenyl)-5-nonylpyridine
2-p-(6-Methyloctanoylphenyl)-5-decylpyridine
2-p-(6-Methyloctanoylphenyl)-5-undecylpyridine
2-p-(6-Methyloctanoylphenyl)-5-dodecylpyridine
2-p-(6-Methyloctanoylphenyl)-5-heptoxymethylpyridine 2-p-(6-Methyloctanoylphenyl)-5-hexoxyethylpyridine
2-p-(6-Methyloctanoylphenyl)-5-pentoxypropylpyridine
2-p-(3-Chloropentoxyphenyl)-5-butylpyridine
2-p-(3-Chloropentoxyphenyl)-5-pentylpyridine
2-p-(3-Chloropentoxyphenyl)-5-hexylpyridine
2-p-(3-Chloropentoxyphenyl)-5-heptylpyridine
2-p-(3-Chloropentoxyphenyl)-5-octylpyridine
2-p-(3-Chloropentoxyphenyl)-5-nonylpyridine
2-p-(3-Chloropentoxyphenyl)-5-decylpyridine
2-p-(3-Chloropentoxyphenyl)-5-undecylpyridine
2-p-(3-Chloropentoxyphenyl)-5-dodecylpyridine
2-p-(3-Chloropentoxyphenyl)-5-heptoxymethylpyridine
2-p-(3-Chloropentoxyphenyl)-5-hexoxyethylpyridine
2-p-(3-Chloropentoxyphenyl)-5-pentoxypropylpyridine
2-p-(3-Cyanopentoxyphenyl)-5-butylpyridine
2-p-(3-Cyanopentoxyphenyl)-5-pentylpyridine
2-p-(3-Cyanopentoxyphenyl)-5-hexylpyridine
2-p-(3-Cyanopentoxyphenyl)-5-heptylpyridine
2-p-(3-Cyanopentoxyphenyl)-5-octylpyridine
2-p-(3-Cyanopentoxyphenyl)-5-nonylpyridine
2-p-(3-Cyanopentoxyphenyl)-5-decylpyridine
2-p-(3-Cyanopentoxyphenyl)-5-undecylpyridine
2-p-(3-Cyanopentoxyphenyl)-5-dodecylpyridine
2-p-(3-Cyanopentoxyphenyl)-5-heptoxymethylpyridine
2-p-(3-Cyanopentoxyphenyl)-5-hexoxyethylpyridine
2-p-(3-Cyanopentoxyphenyl)-5-pentoxypropylpyridine
2-p-(1,6-Dioxa-8-methyldecylphenyl)-5-butylpyridine
2-p-(1,6-Dioxa-8-methyldecylphenyl)-5-pentylpyridine
2-p-(1,6-Dioxa-8-methyldecylphenyl)-5-hexylpyridine
2-p-(1,6-Dioxa-8-methyldecylphenyl)-5-heptylpyridine
2-p-(1,6-Dioxa-8-methyldecylphenyl)-5-octylpyridine
2-p-(1,6-Dioxa-8-methyldecylphenyl)-5-nonylpyridine
2-p-(1,6-Dioxa-8-methyldecylphenyl)-5-decylpyridine
2-p-(1,6-Dioxa-8-methyldecylphenyl)-5-undecylpyridine
2-p-(1,6-Dioxa-8-methyldecylphenyl)-5-dodecylpyridine
2-p-(1,6-Dioxa-8-methyldecylphenyl)-5-heptoxymethylpyridine
2-p-(1,6-Dioxa-8-methyldecylphenyl)-5-hexoxyethylpyridine
2-p-(1,6-Dioxa-8-methyldecylphenyl)-5-pentoxypropylpyridine
2-p-Octyloxyphenyl-5-(2-methyloctyl)pyridine
2-p-Octyloxyphenyl-5-(3-methyloctyl)pyridine
2-p-Octyloxyphenyl-5-(4-methyloctyl)pyridine
2-p-Octyloxyphenyl-5-(5-methyloctyl)pyridine
2-p-Octyloxyphenyl-5-(6-methyloctyl)pyridine
2-p-Octylphenyl-5-(2-methyloctyl)pyridine
2-p-Octylphenyl-5-(3-methyloctyl)pyridine
2-p-Octylphenyl-5-(4-methyloctyl)pyridine
2-p-Octylphenyl-5-(5-methyloctyl)pyridine
2-p-Octylphenyl-5-(6-methyloctyl)pyridine
2-p-(2-Methylbutoxy)phenyl-5-butyloxypyridine
2-p-(2-Methylbutoxy)phenyl-5-pentyloxypyridine
2-p-(2-Methylbutoxy)phenyl-5-hexyloxypyridine
2-p-(2-Methylbutoxy)phenyl-5-heptyloxypyridine
2-p-(2-Methylbutoxy)phenyl-5-octyloxypyridine
2-p-(2-Methylbutoxy)phenyl-5-nonyloxypyridine
2-p-(2-Methylbutoxy)phenyl-5-decyloxypyridine
2-p-(2-Methylbutoxy)phenyl-5-undecyloxypyridine
2-p-(2-Methylbutoxy)phenyl-5-dodecyloxypyridine
2-p-(2-Methylbutoxy)phenyl-5-heptoxymethyloxypyridine
2-p-(2-Methylbutoxy)phenyl-5-hexoxyethyloxypyridine
2-p-(2-Methylbutoxy)phenyl-5-pentoxypropyloxypyridine
2-p-(3-Methylpentoxy)phenyl-5-butyloxypyridine
2-p-(3-Methylpentoxy)phenyl-5-pentyloxypyridine
2-p-(3-Methylpentoxy)phenyl-5-hexyloxypyridine
2-p-(3-Methylpentoxy)phenyl-5-heptyloxypyridine
2-p-(3-Methylpentoxy)phenyl-5-octyloxypyridine
2-p-(3-Methylpentoxy)phenyl-5-nonyloxypyridine
2-p-(3-Methylpentoxy)phenyl-5-decyloxypyridine
2-p-(3-Methylpentoxy)phenyl-5-undecyloxypyridine
2-p-(3-Methylpentoxy)phenyl-5-dodecyloxypyridine
2-p-(3-Methylpentoxy)phenyl-5-heptoxymethyloxypyridine
2-p-(3-Methylpentoxy)phenyl-5-hexoxyethyloxypyridine
2-p-(3-Methylpentoxy)phenyl-5-pentoxypropyloxypyridine
2-p-(6-Methyloctoxy)phenyl-5-butyloxypyridine
2-p-(6-Methyloctoxy)phenyl-5-pentyloxypyridine
2-p-(6-Methyloctoxy)phenyl-5-hexyloxypyridine
2-p-(6-Methyloctoxy)phenyl-5-heptyloxypyridine
2-p-(6-Methyloctoxy)phenyl-5-octyloxypyridine
2-p-(6-Methyloctoxy)phenyl-5-nonyloxypyridine
2-p-(6-Methyloctoxy)phenyl-5-decyloxypyridine
2-p-(6-Methyloctoxy)phenyl-5-undecyloxypyridine
2-p-(6-Methyloctoxy)phenyl-5-dodecyloxypyridine
2-p-(6-Methyloctoxy)phenyl-5-heptoxymethyloxypyridine
2-p-(6-Methyloctoxy)phenyl-5-hexoxyethyloxypyridine
2-p-(6-Methyloctoxy)phenyl-5-pentoxypropyloxypyridine
2-p-(2-Methyloctoxy)phenyl-5-butyloxypyridine
2-p-(2-Methyloctoxy)phenyl-5-pentyloxypyridine
2-p-(2-Methyloctoxy)phenyl-5-hexyloxypyridine
2-p-(2-Methyloctoxy)phenyl-5-heptyloxypyridine
2-p-(2-Methyloctoxy)phenyl-5-octyloxypyridine
2-p-(2-Methyloctoxy)phenyl-5-nonyloxypyridine
2-p-(2-Methyloctoxy)phenyl-5-decyloxypyridine
2-p-(2-Methyloctoxy)phenyl-5-undecyloxypyridine
2-p-(2-Methyloctoxy)phenyl-5-dodecyloxypyridine
2-p-(2-Methyloctoxy)phenyl-5-heptoxymethyloxypyridine
2-p-(2-Methyloctoxy)phenyl-5-hexoxyethyloxypyridine
2-p-(2-Methyloctoxy)phenyl-5-pentoxypropyloxypyridine
2-p-(2-Methylbutyryloxy)phenyl-5-butyloxypyridine
2-p-(2-Methylbutyryloxy)phenyl-5-pentyloxypyridine
2-p-(2-Methylbutyryloxy)phenyl-5-hexyloxypyridine
2-p-(2-Methylbutyryloxy)phenyl-5-heptyloxypyridine
2-p-(2-Methylbutyryloxy)phenyl-5-octyloxypyridine
2-p-(2-Methylbutyryloxy)phenyl-5-nonyloxypyridine
2-p-(2-Methylbutyryloxy)phenyl-5-decyloxypyridine
2-p-(2-Methylbutyryloxy)phenyl-5-undecyloxypyridine
2-p-(2-Methylbutyryloxy)phenyl-5-dodecyloxypyridine
2-p-(2-Methylbutyryloxy)phenyl-5-heptoxymethyloxypyridine
2-p-(2-Methylbutyryloxy)phenyl-5-hexoxyethyloxypyridine
2-p-(2-Methylbutyryloxy)phenyl-5-pentoxypropyloxypyridine
2-p-(3-Methylpentanoyloxy)phenyl-5-butyloxypyridine
2-p-(3-Methylpentanoyloxy)phenyl-5-pentyloxypyridine
2-p-(3-Methylpentanoyloxy)phenyl-5-hexyloxypyridine
2-p-(3-Methylpentanoyloxy)phenyl-5-heptyloxypyridine 2-p-(3-Methylpentanoyloxy)phenyl-5-octyloxypyridine
2-p-(3-Methylpentanoyloxy)phenyl-5-nonyloxypyridine
2-p-(3-Methylpentanoyloxy)phenyl-5-decyloxypyridine
2-p-(3-Methylpentanoyloxy)phenyl-5-undecyloxypyridine
2-p-(3-Methylpentanoyloxy)phenyl-5-dodecyloxypyridine
2-p-(3-Methylpentanoyloxy)phenyl-5-heptoxymethyloxypyridine
2-p-(3-Methylpentanoyloxy)phenyl-5-hexoxyethyloxypyridine
2-p-(3-Methylpentanoyloxy)phenyl-5-pentoxypropyloxypyridine
2-p-(4-Methylhexanoyloxy)phenyl-5-butyloxypyridine
2-p-(4-Methylhexanoyloxy)phenyl-5-pentyloxypyridine
2-p-(4-Methylhexanoyloxy)phenyl-5-hexyloxypyridine
2-p-(4-Methylhexanoyloxy)phenyl-5-heptyloxypyridine
2-p-(4-Methylhexanoyloxy)phenyl-5-octyloxypyridine
2-p-(4-Methylhexanoyloxy)phenyl-5-nonyloxypyridine
2-p-(4-Methylhexanoyloxy)phenyl-5-decyloxypyridine
2-p-(4-Methylhexanoyloxy)phenyl-5-undecyloxypyridine
2-p-(4-Methylhexanoyloxy)phenyl-5-dodecyloxypyridine
2-p-(4-Methylhexanoyloxy)phenyl-5-heptoxymethyloxypyridine
2-p-(4-Methylhexanoyloxy)phenyl-5-hexoxyethyloxypyridine
2-p-(4-Methylhexanoyloxy)phenyl-5-pentoxypropyloxypyridine
2-p-(6-Methyloctanoyloxy)phenyl-5-butyloxypyridine
2-p-(6-Methyloctanoyloxy)phenyl-5-pentyloxypyridine
2-p-(6-Methyloctanoyloxy)phenyl-5-hexyloxypyridine
2-p-(6-Methyloctanoyloxy)phenyl-5-heptyloxypyridine
2-p-(6-Methyloctanoyloxy)phenyl-5-octyloxypyridine
2-p-(6-Methyloctanoyloxy)phenyl-5-nonyloxypyridine
2-p-(6-Methyloctanoyloxy)phenyl-5-decyloxypyridine
2-p-(6-Methyloctanoyloxy)phenyl-5-undecyloxypyridine
2-p-(6-Methyloctanoyloxy)phenyl-5-dodecyloxypyridine
2-p-(6-Methyloctanoyloxy)phenyl-5-heptoxymethyloxypyridine
2-p-(6-Methyloctanoyloxy)phenyl-5-hexoxyethyloxypyridine
2-p-(6-Methyloctanoyloxy)phenyl-5-pentoxypropyloxypyridine
2-p-(6-Methyloctyloxy)phenyl-5-butyloxypyridine
2-p-(6-Methyloctyloxy)phenyl-5-pentyloxypyridine
2-p-(6-Methyloctyloxy)phenyl-5-hexyloxypyridine
2-p-(6-Methyloctyloxy)phenyl-5-heptyloxypyridine
2-p-(6-Methyloctyloxy)phenyl-5-octyloxypyridine
2-p-(6-Methyloctyloxy)phenyl-5-nonyloxypyridine
2-p-(6-Methyloctyloxy)phenyl-5-decyloxypyridine
2-p-(6-Methyloctyloxy)phenyl-5-undecyloxypyridine
2-p-(6-Methyloctyloxy)phenyl-5-dodecyloxypyridine
2-p-(6-Methyloctyloxy)phenyl-5-heptoxymethyloxypyridine
2-p-(6-Methyloctyloxy)phenyl-5-hexoxyethyloxypyridine
2-p-(6-Methyloctyloxy)phenyl-5-pentoxypropyloxypyridine
2-p-Octyloxyphenyl-5-(2-methyloctyloxycarbonyl)-pyridine
2-p-Octyloxyphenyl-5-(3-methyloctyloxycarbonyl)-pyridine
2-p-Octyloxyphenyl-5-(4-methyloctyloxycarbonyl)-pyridine
2-p-Octyloxyphenyl-5-(5-methyloctyloxycarbonyl)-pyridine
2-p-Octyloxyphenyl-5-(6-methyloctyloxycarbonyl)-pyridine
2-p-Dodecyloxyphenyl-5-(2-methyloctyloxycarbonyl)-pyridine
2-p-Undecyloxyphenyl-5-(2-methylbutoxy)pyridine
2-p-Decyloxyphenyl-5-(2-methylbutoxy)pyridine
2-p-Nonyloxyphenyl-5-(2-methylbutoxy)pyridine
2-p-Octyloxyphenyl-5-(2-methylbutoxy)pyridine
2-p-Heptyloxyphenyl-5-(2-methylbutoxy)pyridine
2-p-Dodecanoyloxyphenyl-5-(2-methylbutoxy)pyridine
2-p-Undecanoyloxyphenyl-5-(2-methylbutoxy)pyridine
2-p-Decanoyloxyphenyl-5-(2-methylbutoxy)pyridine
2-p-Nonanoyloxyphenyl-5-(2-methylbutoxy)pyridine
2-p-Octanoyloxyphenyl-5-(2-methylbutoxy)pyridine
2-p-Heptanoyloxyphenyl-5-(2-methylbutoxy)pyridine

EXAMPLE 27

A solution ob 0.01 mol n-butyllithium (5% in n-pentane) is added dropwise at 10°-15° C. to a solution of 0.01 mol of 3-[4-(R-2-octyloxy)phenyl]pyridine (obtainable by coupling 4-(R-2-octyloxy)phenylmagnesium bromide and 3-bromopyridine) in 30 ml of toluene and mixture is subsequently heated for 4 hours under reflux. After working up and purification by chromatography, 2-n-butyl-5-[4-(R-2-octyloxy)phenyl]pyridine is obtained.

The following are obtained in an analogous manner:
2-Pentyl-5-[4-(R-2-octyloxy)phenyl]pyridine
2-Hexyl-5-[4-(R-2-octyloxy)phenyl]pyridine
2-Heptyl-5-[4-(R-2-octyloxy)phenyl]pyridine
2-Octyl-5-[4-(R-2-octyloxy)phenyl]pyridine
2-Nonyl-5-[4-(R-2-octyloxy)phenyl]pyridine
2-Decyl-5-[4-(R-2-octyloxy)phenyl]pyridine
2-Undecyl-5-[4-(R-2-octyloxy)phenyl]pyridine
2-Dodecyl-5-[4-(R-2-octyloxy)phenyl]pyridine

EXAMPLE 28

A liquid crystalline phase consisting of
10% of 2-p-(4-Methylhexyloxy)phenyl-5-heptylpyrimidine,
4% of 2-p-(4-Methylhexyloxy)phenyl-5-decylpyrimidine,
3% of 2-p-(4-Methylhexyloxy)phenyl-5-dodecylpyrimidine,
8% of 2-p-(5-Methylhexyloxy)phenyl-5-nonylpyrimidine,
8% of 2-p-(5-Methylhexyloxy)phenyl-5-undecylpyrimidine,
6% of 2-p-(5-Methylhexyloxy)phenyl-5-dodecylpyrimidine,
6% of 2-p-(6-Methylhexyloxy)phenyl-5-octylpyrimidine
30% of r-1-Cyano-cis-4-(4'-octyloxybiphenyl-4-yl)-1-octylcyclohexane
15% of r-1-Cyano-cis-4-(4'-octyloxybiphenyl-4-yl)-1-butylcyclohexane
10% of 4-(5-Hexylpyrimidin-2-yl)phenyl-2-chloropropionate has c.p. $-18°$ $S_C^*$ $66°$ $S_A^*$ $70°$ Ch $82°$ I.

EXAMPLE 29

A liquid crystalline phase consisting of
10% of 2-p-(4-Methylhexyloxy)phenyl-5-heptylpyrimidine, 4% of 2-p-(4-Methylhexyloxy)phenyl-5-decylpyrimidine, 3% of 2-p-(4-Methylhexyloxy)phenyl-5-dodecylpyrimidine, 8% of 2-p-(5-Methylheptyloxy)phenyl-5-nonylpyrimidine, 8% of 2-p-(5-Methylheptyloxy)phenyl-5-undecylpyrimidine, 6% of 2-p-(5-Methylheptyloxy)phenyl-5-dodecylpyrimidine, 6% of 2-p-(6-Methylheptyloxy)phenyl-5-octylpyrimidine, 30% of r-1-Cyano-cis-4-(4'-octyloxybiphenyl-4-yl)-1-octylcylohexane, 15% of r-1-Cyano-cis-4-(4'-octylbiphenyl-4-yl)-1-butylcyclohexane and 6% of 1-(4'-Pentylbiphenyl-4-yl)-2-(1-cyano-3-methylcyclohexyl)ethane and 4% of 4-(5-Nonylpyrimidin-2-yl)phenyl-p-(2-octyloxycarbonyl)benzyl ether has c.p. $-15°$ $S_C^*$ $60°$ $S_A^*$ $66°$ Ch $80°$ I.

EXAMPLE 30

A liquid crystalline material consisting of an achiral base mixture comprising 3.3% of 2-p-Hexyloxyphenyl-5-heptylpyrimidine,
7.7% of 2-p-Hexyloxyphenyl-5-nonylpyrimidine,
3.3% of 2-p-Heptyloxyphenyl-5-heptylpyrimidine,
3.3% of 2-p-Octyloxyphenyl-5-heptylpyrimidine,
3.3% of 2-p-Nonyloxyphenyl-5-heptylpyrimidine,
25.6% of 2-p-Nonylphenyl-5-nonylpyrimidine,
31.2r-1-Cyano-cis-4-(4'-octyloxybiphenyl-4-yl)-1-butylcyclohexane,
15.6% of r-1-Cyano-cis-4-(4'-heptylbiphenyl-4-yl)-1-hexylcyclohexane and
10% of optically active ethyl 2-[p-Nonylpyrimidin-2-yl)phenoxy)propanoate has c.p. $-5°$ $S_C^*$ $63°$ $S_A^*$ $64°$ Ch $89°$ I and a spontaneous polarization of 10.4 nC/cm² at 20°.

EXAMPLE 31

A liquid crystalline phase consisting of the achiral base mixture from Example 30 and 10% of optically active 2-p-(2-octyloxy)-phenyl-5-nonylpyrimidine has c.p. $-12°$ $S_C^*$ $61°$ $S_A^*$ $67°$ $S_A^*$ $67°$ Ch $82°$ I. This material exhibits a particularly favourable low temperature behaviour.

EXAMPLE 32

A liquid crystalline phase consisting of the achiral base mixture from Example 30 and 10% of optically active 2,5-dimethylhex-4-enyloxyphenyl-5-hexylpyrimidine has c.p. $0°$, $S_C^*$ $S_C^*$ $68°$ $S_A^*$ $72°$ Ch $91°$ I.

EXAMPLE 33

A liquid crystalline phase consisting of the achiral base mixture from Example 30 and 10% of optically active 2-methylbutyl p-(5-heptylpyrimidin-2-yl)cinnamate has c.p. $5°$, $S_C^*$ $70°$ $S_A^*$ $86°$ Ch $89°$ I.

EXAMPLE 34

A liquid crystalline phase consisting of the achiral base mixture from Example 30 and 10% of optically active 2-octyl p-(5-heptylpyrimidin-2-yl)cinnamate has c.p. $3°$, $S_C^*$ $64°$ $S_A^*$ $83°$ Ch $91°$ I and a spontaneous polarization of 3.3 nC/cm² at 20°.

EXAMPLE 35

A liquid crystalline phase consisting of the achiral base mixture from Example 30 and 10% of optically active 2-methylbutyl p-(5-heptylpyrimidin-2-yl)phenylpropionate has c.p. $-2°$, $S_C^*$ $70°$ $S_A^*$ $79°$ Ch $93°$ I.

EXAMPLE 36

A liquid crystalline phase consisting of the achiral base mixture from Example 30 and 10% of optically active 2-p-(3,7-dimethyloctyloxy)phenyl-5-hexylpyrimidine has c.p. $3°$, $S_C^*$ $64°$ $S_A^*$ $67°$ Ch $88°$ I and a spontaneous polarization of 1.2 nC/cm² at 20°.

EXAMPLE 37

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
25% of 2-p-nonyloxyphenyl-5-nonylpyrimidine,
28% of r-1-cyano-cis-4-(4'-octyloxybiphenyl-4-yl)-1-butylcyclohexane,
4% of r-1-cyano-cis-4-(4'-octylbiphenyl-4-yl)-1-butylcyclohexane,
6% of r-1-cyano-cis-4-(trans-4-pentylcyclohexyl)-1-(trans-4-pentylcyclohexyl) cyclohexane
10% of optically active 1-(4'-pentylbiphenyl-4-yl)-2-(1-cyano-3-methylcyclohexyl) ethane and
8% of optically active 2-p-dodecylphenyl-5-(2-octyloxy) pyridazine
has c.p. $-15°$ $S_C^*$ $58°$ $S_A^*$ $64°$ Ch $82°$ I and a spontaneous polarization of 19 nC/cm².

EXAMPLE 38

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl) cyclohexane and
10% of optically active 2-p-(2-octyloxycarbonylphenyl)-5-nonylpyrimidine
has $S_C^*$ $68°$ $S_A$ $81°$ Ch $96$ I.

EXAMPLE 39

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-hexyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)-cyclohexane and 10% of optically active 2-octyl p-[p-(5-nonylpyrimidin-2-yl)-phenoxymethyl]-benzoate has $S_C^*$ 72° $S_A^*$ 83° Ch 93° I and a spontaneous polarization of 5 nC/cm².

EXAMPLE 40

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)-cyclohexane and
10% of optically active p-(5-nonylpyrimidin-2-yl)-phenyl 3-chloro-4-(2-octyloxy)-benzoate has $S_C^*$ 70° Ch 93° I.

EXAMPLE 41

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)-cyclohexane and
10% of optically active 2-p-(2-methylbutoxycarbonyl)-phenyl-5-heptylpyrimidine has $S_C^*$ 55° $S_A^*$ 77° Ch 91° I.

EXAMPLE 42

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)-cyclohexane and
10% of optically active 2-methylbutyl p-[p-(5nonylpyrimidin-2-yl)-phenoxymethyl]-benzoate has $S_C$ 78° $S_A^*$ 84° Ch 90° I and a spontaneous polarization of 4 nC/cm².

EXAMPLE 43

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)-cyclohexane and
10% of optically active 2-p-(2-octyloxycarbonyl)-phenyl-5-heptylpyrimidine has $S_C^*$ 50° $S_A$ 78° Ch 86° I.

EXAMPLE 44

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)-cyclohexane and
10% of optically active p-[p-(5-nonylpyrimidin-2-yl) phenoxymethyl]-(2-methylbutoxy)-benzene has $S_C^*$ 80° Ch 100° I.

EXAMPLE 45

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)-cyclohexane and
10% of optically active 1-[p-(5-heptylpyrimidin-2-yl) phenyl]-2-p-(2-octyloxycarbonylphenyl)-ethane has $S_C$ 77° $S_A$ 80° Ch 89° I.

EXAMPLE 46

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)-cyclohexane and
10% of optically active 1-[p-(5-heptylpyrimidin-2-yl) phenyl]-2-p-(2-octyloxycarbonylphenyl)-ethane has $S_C^*$ 73° $S_A^*$ 78° Ch 91° I.

EXAMPLE 47

A liquid crystalline phase consisting of
3% of 2-p-hexyloxyphenyl-5-heptylpyrimidine,
3% of 2-p-heptyloxyphenyl-5-heptylpyrimidine, 3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)-cyclohexane and
10% of optically active 2-p-(2-methylbutylmercaptophenyl)-5-heptylpyrimidine
has $S_C^*$ 63° $S_A^*$ 65° Ch 88° I.

All the phases listed in the examples 38 to 47 exhibit $K/S_C^*$ phase transitions below room temperature.

EXAMPLE 48

A liquid crystalline phase consisting of
3% of 2-p-hexyloxyphenyl-5-octylpyrimidine,
3% of 2-p-heptyloxyphenyl-5-octylpyrimidine,
3% of 2-p-octyloxyphenyl-5-octylpyrimidine,
3% of 2-p-nonyloxyphenyl-5-octylpyrimidine,
3% of 2-p-hexyloxyphenyl-5-nonylpyrimidine,
23% of 2-p-nonyloxyphenyl-5-nonylpyrimidine,
25% of r-1-cyano-cis-4-(4'-octyloxybiphenyl-4-yl)-1-octylcyclohexane,
13% of r-1-cyano-cis-4-(4'-heptylbiphenyl-4-yl)-1-hexylcyclohexane,
4% of r-1-cyano-cis-4-(trans-4-pentylcyclohexyl)-1-(trans-4-pentylcyclohexyl)-cyclohexane
10% of optically active 1-(4'-pentylbiphenyl-4-yl)-2-(1-cyano-3-methylcyclohexyl)-ethane and
10% of optically active 2-p-(2-methylbutoxy)-phenyl-5-octyloxycarbonyloxypyrazine
has K −18° $S_C^*$ 61° $S_A^*$ 67° Ch 84° I and a spontaneous polarization of 22 nC/cm².

EXAMPLE 49

A liquid crystalline phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5nonylpyrimidine,
32% of r-1-cyano-cis-4-(4'-octyloxybiphenyl-4-yl)-1-octylcyclohexane,
13% of r-1-cyano-cis-4-(4'-heptylbiphenyl-4-yl)-1-hexylcyclohexane,
3% of r-1-cyano-cis-4-(trans-4-pentylcyclohexyl)-1-(trans-4-pentylcyclohexyl)-cyclohexane and
10% of optically active ethyl 2-[p-(5-nonylpyrimidin-2-yl) phenoxy]-propanoate
has K < −30° $S_C^*$ 61° $S_A^*$ 66° Ch 85° I and a spontaneous polarization of 9.7 nC/cm².

EXAMPLE 50

A liquid crystalline phase is prepared which consists of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
32% of r-1-cyano-cis-4-(4'-octyloxybiphenyl-4-yl)-1-octylcyclohexane,
13% of r-1-cyano-cis-4-(4'-heptylbiphenyl-4-yl)-1-hexylcyclohexane,
3% of r-1-cyano-cis-4-(trans-4-pentylcyclohexyl)-1-(trans-4-pentylcyclohexyl)-cyclohexane and
10% of optically active 2-p-(5-methylheptyl)-phenyl-5-nonylpyrazine.

EXAMPLE 51

3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
32% of r-1-cyano-cis-4-(4'-octyloxybiphenyl-4-yl)-1-octylcyclohexane,
13% of r-1-cyano-cis-4-(4'-heptylbiphenyl-4-yl)-1-hexylcyclohexane,
3% of r-1-cyano-cis-4-(trans-4-pentylcyclohexyl)-1-(trans-4-pentylcyclohexyl)-cyclohexane and
10% of optically active 2-p-(5-methylheptyl) phenyl-5-(1,4-dioxanonyl)-pyrazine.

EXAMPLE 52

A liquid crystalline phase is prepared which consists of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
32% of r-1-cyano-cis-4-(4'-octyloxybiphenyl-4-yl)-1-octylcyclohexane,
13% of r-1-cyano-cis-4-(4'-heptylbiphenyl-4-yl)-1-hexylcyclohexane,
3% of r-1-cyano-cis-4-(trans-4-pentylcyclohexyl)-1-(trans-4-pentylcyclohexyl)-cyclohexane and
10% of optically active ethyl 2-[p-(5-heptyloxypyrazin-2-yl) phenoxy]-propanoate.

EXAMPLE 53

A liquid crystalline phase is prepared which consists of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
32% of r-1-cyano-cis-4-(4'-octyloxybiphenyl-4-yl)-1-octylcyclohexane,
13% of r-1-cyano-cis-4-(4'-heptylbiphenyl-4-yl)-1-hexylcyclohexane,
3% of r-1-cyano-cis-4-(trans-4-pentylcyclohexyl)-1-(trans-4-pentylcyclohexyl)-cyclohexane and
10% of optically active ethyl 2-[p-(5-heptylpyridin-2-yl) phenoxy]-propanoate.

EXAMPLE 54

A liquid crystalline phase was prepared which consisted of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine, 32% of r-1-cyano-cis-4-(4'-octyloxybiphenyl-4-yl)-1-octylcyclohexane, 13% of r-1-cyano-cis-4-(4'-heptylbiphenyl-4-yl)-1-hexylcyclohexane, 3% of r-1-cyano-cis-4-(trans-4-pentylcyclohexyl)-1-(trans-4-pentylcyclohexyl)-cyclohexane and 10% of optically active butyl 2-[p-(5-nonylpyridin-2-yl) phenoxy]-propanoate.

EXAMPLE 55

A liquid crystalline phase is prepared which consists of

3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
32% of r-1-cyano-cis-4-(4'-octyloxybiphenyl-4-yl)-1-octylcyclohexane,
13% of r-1-cyano-cis-4-(4'-heptylbiphenyl-4-yl)-1-hexylcyclohexane,
3% of r-1-cyano-cis-4-(trans-4-pentylcyclohexyl)-1-(trans-4-pentylcyclohexyl)-cyclohexane and
10% of optically active ethyl 2-[p-(5-nonylpyridazin-2-yl) phenoxy]-propanoate.

EXAMPLE 56

A liquid crystalline phase is prepared which consists of

3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
32% of r-1-cyano-cis-4-(4'-octyloxybiphenyl-4-yl)-1-octylcyclohexane,
13% of r-1-cyano-cis-4-(4'-heptylbiphenyl-4-yl)-1-hexylcyclohexane,
3% of r-1-cyano-cis-4-(trans-4-pentylcyclohexyl)-1-(trans-4-pentylcyclohexyl)-cyclohexane and
10% of optically active ethyl 2-[p-(4-nonylpyridin-2-yl) benzoyloxy]-propanoate.

In the mixtures of optically active materials used in examples 37 and 48, in each case one additive is intended to produce a right-handed twist, while the other additive is intended to produce a left-handed twist.

We claim:

1. A nitrogen-containing heterocycle of the formula I $$R^1\text{---}A^1\text{---}Z^1\text{---}A^2\text{---}R^2 \qquad \text{I}$$

in which
one of the radicals $R^1$ and $R^2$ is an alkyl group of 1–15 carbon atoms, in which one or two non-adjacent $CH_2$ groups can be replaced by —O—;
the other radical $R^1$ or $R^2$ is an optically active organic radical with an asymmetric carbon atom of the formula

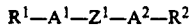

wherein
X is —O—, —CO—O, or —O—CO—,
Q is —CH$_2$— or a single bond,
Y is CH$_3$,
R is straight-chain alkyl of 1 to 7 C atoms, in which the CH$_2$ group linked to the asymmetric C atom is replaced by —O—, —CO—O—, or —O—CO—, $A^1$ is

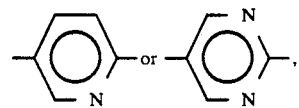

$A^2$ is 1,4-phenylene which is unsubstituted or substituted by one or two F atoms, and
$Z^1$ is a single bond; with the proviso that when $A^1$ is pyrimidine-2,5-diyl then X is —O—.

2. In a ferroelectric liquid crystalline phase comprising at least two liquid crystalline components, the improvement wherein at least one component is a compound of claim 1.

3. In an electro-optical display element comprising a liquid crystal cell having a liquid crystalline phase, the improvement wherein the phase is according to claim 2.

4. A nitrogen-containing heterocycle according to claim 1, wherein $A^1$ is pyrimidine-2,5-diyl.

5. A nitrogen-containing heterocycle according to claim 1, wherein $A^1$—$Z^1$—$A^2$ is a structural element selected from the group of the formulae 1 and 2:

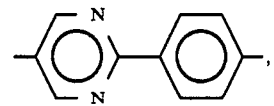    1

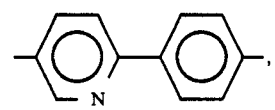    2

6. A nitrogen-containing heterocycle according to claim 1, of the formula

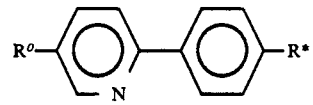

or

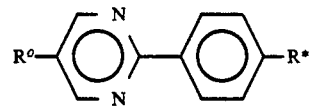

in which R° is straight-chain alkyl or alkoxy of, in each case, 2 to 12 carbon atoms, and R* has one of the meanings given for the optically active organic radical

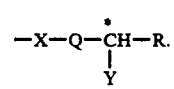

7. In a ferroelectric liquid crystalline phase comprising at least two liquid crystalline components, the improvement wherein at least one component is a compound of claim 5.

8. A compound of claim 1, wherein X is O, Q is a single bond, and R is straight-chain alkanoyloxy with up to 7 C atoms.

9. A compound of claim 1, wherein $A^1$ is pyridine-2,5-diyl.

* * * * *